(12) United States Patent
Zhou et al.

(10) Patent No.: US 10,391,467 B2
(45) Date of Patent: Aug. 27, 2019

(54) FABRICATION OF PATTERNED ARRAYS

(71) Applicant: CENTRILLION TECHNOLOGY HOLDINGS CORPORATION, Grand Cayman (KY)

(72) Inventors: Wei Zhou, Saratoga, CA (US); Filip Crnogorac, Palo Alto, CA (US); Glenn McGall, Palo Alto, CA (US); Jian Cao, Sunnyvale, CA (US)

(73) Assignee: CENTRILLION TECHNOLOGY HOLDINGS CORPORATION, Grand Cayman (KY)

( * ) Notice: Subject to any disclaimer, the term of this patent is extended or adjusted under 35 U.S.C. 154(b) by 372 days.

(21) Appl. No.: 15/101,671

(22) PCT Filed: Dec. 5, 2014

(86) PCT No.: PCT/US2014/068955
§ 371 (c)(1),
(2) Date: Jun. 3, 2016

(87) PCT Pub. No.: WO2015/085275
PCT Pub. Date: Jun. 11, 2015

(65) Prior Publication Data
US 2016/0303534 A1    Oct. 20, 2016

Related U.S. Application Data

(60) Provisional application No. 61/912,027, filed on Dec. 5, 2013, provisional application No. 61/912,559, filed
(Continued)

(51) Int. Cl.
*C12Q 1/68* (2018.01)
*B01J 19/00* (2006.01)
*C12Q 1/6837* (2018.01)

(52) U.S. Cl.
CPC ........ *B01J 19/0046* (2013.01); *C12Q 1/6837* (2013.01); *B01J 2219/00709* (2013.01); *B01J 2219/00722* (2013.01)

(58) Field of Classification Search
None
See application file for complete search history.

(56) References Cited

U.S. PATENT DOCUMENTS

| 4,469,863 A | 9/1984 | Ts'o et al. |
| 4,988,617 A | 1/1991 | Landegren et al. |

(Continued)

FOREIGN PATENT DOCUMENTS

| CN | 102224257 A | 10/2011 |
| EP | 1291354 A2 | 3/2003 |

(Continued)

OTHER PUBLICATIONS

Gunderson et al. (Nature Genetics, 2005, 37(5):549-554) (Year: 2005).*

(Continued)

*Primary Examiner* — Stephanie K Mummert
(74) *Attorney, Agent, or Firm* — Wilson Sonsini Goodrich & Rosati

(57) ABSTRACT

Provided herein are methods and compositions for the fabrication of patterned arrays, such as nucleotide arrays. The methods and compositions are suited for the transfer and reorientation of array components.

20 Claims, 36 Drawing Sheets

Related U.S. Application Data on Dec. 6, 2013, provisional application No. 61/971,542, filed on Mar. 28, 2014, provisional application No. 61/979,448, filed on Apr. 14, 2014, provisional application No. 62/012,238, filed on Jun. 13, 2014.

(56) References Cited

U.S. PATENT DOCUMENTS

| | | |
|---|---|---|
| 5,034,506 A | 7/1991 | Summerton et al. |
| 5,216,141 A | 6/1993 | Benner |
| 5,235,033 A | 8/1993 | Summerton et al. |
| 5,242,794 A | 9/1993 | Whiteley et al. |
| 5,386,023 A | 1/1995 | Sanghvi et al. |
| 5,476,930 A | 12/1995 | Letsinger et al. |
| 5,478,893 A | 12/1995 | Ghosh et al. |
| 5,494,810 A | 2/1996 | Barany et al. |
| 5,602,240 A | 2/1997 | De et al. |
| 5,637,684 A | 6/1997 | Cook et al. |
| 5,644,048 A | 7/1997 | Yau |
| 5,712,124 A | 1/1998 | Walker |
| 5,750,341 A | 5/1998 | Macevicz |
| 5,780,613 A | 7/1998 | Letsinger et al. |
| 5,795,714 A | 8/1998 | Cantor et al. |
| 5,969,119 A | 10/1999 | Macevicz |
| 6,262,216 B1 | 7/2001 | McGall |
| 6,306,597 B1 | 10/2001 | Macevicz |
| 6,410,278 B1 | 6/2002 | Notomi et al. |
| 6,511,803 B1 * | 1/2003 | Church .............. C07K 1/047 435/287.2 |
| 6,582,938 B1 | 6/2003 | Su et al. |
| 6,692,914 B1 | 2/2004 | Klaerner et al. |
| 6,994,964 B1 | 2/2006 | Chang et al. |
| 7,048,481 B2 | 5/2006 | Sugata et al. |
| 7,170,050 B2 | 1/2007 | Turner et al. |
| 7,211,390 B2 | 5/2007 | Rothberg et al. |
| 7,244,559 B2 | 7/2007 | Rothberg et al. |
| 7,244,567 B2 | 7/2007 | Chen et al. |
| 7,250,253 B1 | 7/2007 | Klapproth et al. |
| 7,264,929 B2 | 9/2007 | Rothberg et al. |
| 7,302,146 B2 | 11/2007 | Turner et al. |
| 7,313,308 B2 | 12/2007 | Turner et al. |
| 7,315,019 B2 | 1/2008 | Turner et al. |
| 7,323,305 B2 | 1/2008 | Leamon et al. |
| 7,335,762 B2 | 2/2008 | Rothberg et al. |
| 7,405,281 B2 | 7/2008 | Xu et al. |
| 7,462,452 B2 | 12/2008 | Williams et al. |
| 7,462,468 B1 | 12/2008 | Williams et al. |
| 7,476,503 B2 | 1/2009 | Turner et al. |
| 7,476,504 B2 | 1/2009 | Turner |
| 7,670,770 B2 | 3/2010 | Chou et al. |
| 7,713,689 B2 | 5/2010 | Chilkoti |
| RE42,315 E | 5/2011 | Lopez et al. |
| 8,198,028 B2 * | 6/2012 | Rigatti .............. C12Q 1/6837 435/6.12 |
| 8,367,314 B2 | 2/2013 | Chilkoti |
| 9,328,382 B2 | 5/2016 | Drmanac et al. |
| 9,834,814 B2 * | 12/2017 | Peter .............. C12Q 1/6841 |
| 10,030,261 B2 * | 7/2018 | Frisen .............. C12Q 1/6841 |
| 2002/0068290 A1 | 6/2002 | Yarovinsky |
| 2002/0132245 A1 | 9/2002 | Boles et al. |
| 2003/0082576 A1 | 5/2003 | Jones et al. |
| 2004/0171053 A1 | 9/2004 | Hu |
| 2004/0185260 A1 | 9/2004 | Luzinov et al. |
| 2005/0084912 A1 | 4/2005 | Poponin |
| 2005/0158879 A1 | 7/2005 | Klaerner et al. |
| 2005/0244863 A1 | 11/2005 | Mir |
| 2006/0205089 A1 | 9/2006 | Dratz et al. |
| 2008/0206764 A1 | 8/2008 | Williams et al. |
| 2009/0002935 A1 | 1/2009 | Cheng |
| 2009/0024331 A1 | 1/2009 | Tomaney et al. |
| 2009/0026082 A1 | 1/2009 | Rothberg et al. |
| 2009/0029385 A1 | 1/2009 | Christians et al. |
| 2009/0068655 A1 | 3/2009 | Williams et al. |
| 2009/0121133 A1 | 5/2009 | Amirparviz |
| 2009/0181861 A1 | 7/2009 | Li et al. |
| 2009/0326208 A1 | 12/2009 | Carrino et al. |
| 2010/0022412 A1 | 1/2010 | Rigatti et al. |
| 2010/0173394 A1 | 7/2010 | Colston, Jr. et al. |
| 2010/0203597 A1 | 8/2010 | Chen et al. |
| 2010/0208724 A1 | 8/2010 | Booth et al. |
| 2010/0240827 A1 | 9/2010 | Barwick et al. |
| 2010/0268478 A1 | 10/2010 | Andregg et al. |
| 2011/0046324 A1 | 2/2011 | Matyjaszewski et al. |
| 2011/0143966 A1 | 6/2011 | McGall et al. |
| 2011/0143967 A1 | 6/2011 | McGall et al. |
| 2011/0172119 A1 | 7/2011 | Boutell |
| 2012/0004132 A1 | 1/2012 | Zhang et al. |
| 2012/0021200 A1 | 1/2012 | Koberstein et al. |
| 2012/0208724 A1 | 8/2012 | Steemers et al. |
| 2012/0258313 A1 | 10/2012 | Wen et al. |
| 2012/0270964 A1 | 10/2012 | Piletsky et al. |
| 2013/0143771 A1 | 6/2013 | Chilkoti |
| 2013/0157870 A1 | 6/2013 | Pushkarev et al. |
| 2013/0165350 A1 | 6/2013 | Kuimelis et al. |
| 2013/0171461 A1 | 7/2013 | Dach et al. |
| 2013/0172214 A1 | 7/2013 | Ye et al. |
| 2013/0211006 A1 | 8/2013 | Menchen et al. |
| 2013/0244249 A1 | 9/2013 | Jiang et al. |
| 2014/0186940 A1 | 7/2014 | Goel |
| 2014/0357523 A1 | 12/2014 | Zeiner et al. |
| 2015/0141269 A1 | 5/2015 | Soldatov et al. |
| 2016/0046985 A1 | 2/2016 | Drmanac et al. |
| 2016/0168632 A1 | 6/2016 | Edwards |
| 2016/0244548 A1 | 8/2016 | Boniface et al. |
| 2016/0298110 A1 | 10/2016 | McGall |
| 2016/0303534 A1 | 10/2016 | Zhou et al. |
| 2016/0369334 A1 | 12/2016 | Zhou et al. |
| 2017/0016063 A1 | 1/2017 | McGall et al. |
| 2017/0022554 A1 | 1/2017 | Drmanac et al. |

FOREIGN PATENT DOCUMENTS

| | | |
|---|---|---|
| EP | 1655069 A1 | 5/2006 |
| WO | WO-9844151 A1 | 10/1998 |
| WO | WO-0102452 A1 | 1/2001 |
| WO | WO-0227026 A2 | 4/2002 |
| WO | WO-03010203 A1 | 2/2003 |
| WO | WO-2004067759 A2 | 8/2004 |
| WO | WO-2004081183 A2 | 9/2004 |
| WO | WO-2007060456 A1 | 5/2007 |
| WO | WO-2007133831 A2 | 11/2007 |
| WO | WO-2008022332 A2 | 2/2008 |
| WO | WO-2010003132 A1 | 1/2010 |
| WO | WO-2010058342 A1 | 5/2010 |
| WO | WO-2010100265 A1 | 9/2010 |
| WO | WO-2012106546 A2 | 8/2012 |
| WO | WO-2012134602 A2 | 10/2012 |
| WO | WO-2012140224 A1 | 10/2012 |
| WO | WO-2013056090 A1 | 4/2013 |
| WO | WO-2013063382 A2 | 5/2013 |
| WO | WO-2012106546 A3 | 11/2013 |
| WO | WO-2013184754 A2 | 12/2013 |
| WO | WO-2015017759 A1 | 2/2015 |
| WO | WO-2015085268 A1 | 6/2015 |
| WO | WO-2015085274 A1 | 6/2015 |
| WO | WO-2015085275 A2 | 6/2015 |
| WO | WO-2015085275 A3 | 9/2015 |
| WO | WO-2016201111 A1 | 12/2016 |

OTHER PUBLICATIONS

Epicentre, DNA topoisomerase I, 2012. Vaccinia, Cat. Nos. VT710500, VT7101K and VT7105K.

European search report and search opinion dated Aug. 24, 2017 for EP Application No. 14867494.8.

European search report and search opinion dated Aug. 25, 2017 for EP Application No. EP14867116.7.

Office action dated Sep. 21, 2017 for U.S. Appl. No. 15/178,411.

Akeroyd, et al. The combination of living radical polymerization and click chemistry for the synthesis of advanced macromolecular architectures. European Polymer Journal. 2011; 47.6: 1207-1231.

Anonymous. Topomize DNA library prep kit. Nov. 10, 2015.

(56) References Cited

OTHER PUBLICATIONS

"Sawai, H., Synthesis and properties of oligoadenylic acids containing 2-5- phosphoramide linkage. The chemical society of Japan. 1984.805-808.".
Ayres, et al. Polymer brushes: Applications in biomaterials and nanotechnology. Polym. Chem. 2010; 1: 769-777.
Barbey, et al. Polymer brushes via surface-initiated controlled radical polymerization: synthesis, characterization, properties, and applications. Chem Rev. Nov. 2009;109(11):5437-5527. doi: 10.1021/cr900045a.
Beaucage, et al. Tetrahedron Letters. 1981; 22:1859-1862.
Bensimon, A. et al. Alignment and sensitive detection of DNA by a moving interface. Science 265, 2096-2098, (1994).
Bentley et al. Accurate whole human genome sequencing using reversible terminator chemistry. Nature 456(7218):53-59 (2008).
Braunecker et al. Controlled/living radical polymerization: Features, developments, and perspectives. Progress in Polymer Science 32(1):93-146 (2007).
Brill, et al., Synthesis of Oligodeoxynucleoside phosphorodithioates via thioamidites. Journal American Chemical society. 111; 1989.
Brown, et al., Chemical synthesis and cloning of a tyrosine tRNA gene. Methods of enzymology. Academic press. 1979.
Carlsson, et al., Screening for genetic mutations. Scientific correspondence. Nature. 1996; 380:207.
U.S. Appl. No. 62/012,238, filed Jun. 13, 2014.
U.S. Appl. No. 62/173,140, filed Jun. 9, 2015.
U.S. Appl. No. 61/979,448, filed Apr. 14, 2014.
Cullen, et al. Polymeric brushes as functional templates for immobilizing ribonuclease A: study of binding kinetics and activity. Langmuir. Feb. 5, 2008;24(3):913-20. Epub Dec. 13, 2007.
Ding, et al., Single-molecule mechanical identification and sequencing. Nature Methods. Apr. 2012; 9(4): 367-372.
Eckstein, F., Oligonucleotides and Analogues: A Practical Approach, Oxford University Press. 1991.
Edmondson, et al. Polymer brushes via surface-initiated polymerizations. Chem Soc Rev. Jan. 10, 2004;33(1):14-22. Epub Dec. 2, 2003.
Egholm, et al., Peptide nucleic acids (PNA). Oligonucleotide analogs with an achiral. Journal American Chemical Society. 1992: 114 (5); pp. 1895-1897.
Egholm, et al., PNA hybridizes to complementary oligonucleotides obeying the Watson-Crick hydrogen-bonding rules. Nature. Oct. 7, 1993;365(6446):566-8.
European Search Report and search opinion dated Sep. 29, 2016 for International Application EP 16173782.0.
European search report with written opinion dated Jul. 17, 2017 for EP14868406.
Ferree, et al., Electrokinetic Stretching of Tethered DNA. Biophys J. Oct. 2003; 85(4): 2539-2546.
Fodor, S. P. et al. Light-directed, spatially addressable parallel chemical synthesis. Science 251, 767-773, (1991).
Galvin, et al. Applications of surface-grafted macromolecules derived from post-polymerization modification reactions. Progress in Polymer Science. 2012; 37.7: 871-906.
Gao, et al., In Situ synthesis of oligonucleotide microarrays. Biopolymers. 2004. 73; 579-596.
Gueroui, et al., Observation by fluorescence microscopy of transcription on single combed DNA. Proceedings of the National Academy of Sciences of the United States of America 99, 6005-6010, (2002).
Haber, et al., Magnetic tweezers for DNA micromanipulation. Review of scientific instruments. 2000. 71:4561.
Henry, et al. Three-dimensional arrangement of short DNA oligonucleotides at surfaces via the synthesis of DNA-branched polyacrylamide brushes by SI-ATRP. Macromol Rapid Commun. Sep. 15, 2011;32(18):1405-10. doi: 10.1002/marc.201100317. Epub Jul. 28, 2011.
Horn, et al., Oligonucleotides with Alternating Anionic and Cationic Phosphoramidate Linkages: Synthesis and Hybridization of Stereo-uniform Isomers. Tetrhedron letters. 1996. 37:6; 743-746.

International search report and written opinion dated Feb. 24, 2015 for PCT/US2014/068947.
International search report and written opinion dated Apr. 28, 2015 for PCT Application No. PCT/US14/68954.
International search report and written opinion dated Jun. 25, 2015 for PCT Application No. PCT/US14/68955.
International Search Report and Written Opinion dated Sep. 23, 2016 for International Application PCT/US2016/036709.
Jeffs, et al., Unusual conformation of a 3'-thioformacetal linkage in a DNA duplex*. Journal of Biomolecular NMR. 1994. 17-34.
Jenkins, et al., The Biosynthesis of Carbocyclic Nucleosides. Chemical society reviews. 1995; 169-176.
Kiedrowski, et al. Parabolic growth of a self-replicating hexadeoxynucleotide bearing a 3-5-phosphoamidate linkage. Agnew. Chem. 1991; 4:30.
Kim et al., Multiplexed single-molecule assay for enzymatic activity on flow-stretched DNA. Nat Methods. May 2007;4(5):397-9. Epub Apr. 15, 2007.
Kizhakkedathu, et al. Poly(oligo(ethylene glycol)acrylamide) Brushes by Surface Initiated Polymerization: Effect of Macromonomer Chain Length on Brush Growth and Protein Adsorption from Blood Plasma. Langmuir. 2009; 25: 3794-3801.
Koshkin, et al. LNA (Locked Nucleic Acid): An RNA Mimic Forming Exceedingly Stable LNA: LNA Duplexes. Journal American Chemical Society 1998: 120;13252-3.
Lee, et al. Immobilization of Amine-modified Oligonucleotides on Bifunctional Polymer Brushes Synthesized by Surface-initiated Polymerization. Bull. Korean Chem. Soc. 2012; 33(6): 2043-6.
Letsinger et al., Cationic oligonucleotides. J. Am. Chem. Soc.1988; 110(3):4470-4471.
Letsinger et al., Effects of pendant groups at phosphorus on binding properties of d-ApA analogues. Nucleic Acids Res. Apr. 25, 1986;14(8):3487-99.
Letsinger et al., Hybridization of Alternating Cationic/Anionic Oligonucleotide to RNA Segments. Nucleosides & Nucleotides. 13:1597 (1994).
Letsinger, et al., Nucleotide chemistry. XVI. Phosporamidate analogs of oligonucleotides. J. Org. Chem.,1970,35(11),pp. 3800-3803.
Mag et al., Synthesis and selective cleavage of an oligodeoxynucleotide containing a bridged internucleotide 5'-phosphorothioate linkage. Nucleic Acids Res. 19:1437 (1991).
Mansfeld, et al. Clickable initiators, monomers and polymers in controlled radical polymerizations-a prospective combination in polymer science. Polymer Chemistry. 2010; 1.10: 1560-1598.
Marguiles, et al. Genome sequencing in microfabricated high-density picolitre reactors. Nature. Sep. 15, 2005;437(7057):376-80. Epub Jul. 31, 2005.
McGall, G. H. & Christians, F. C. High-density genechip oligonucleotide probe arrays. Adv Biochem Eng Biotechnol 77, 21-42, (2002).
Meier, et al., Peptide nucleic acids (PNas)-Unusual properties nonionic oligonucleotide analogues. Angew. Chemical. Int. Ed. Engl. 1992; 31:8.
Mesmaeker, et al. Comparison of rigid and flexible backbones in antisense oligonucleotides. Bioorganic and medical chemistry. 1994. 4;3;395-398.
Michalet, X. et al. Dynamic molecular combing: stretching the whole human genome for high-resolution studies. Science 277, 1518-1523, (1997).
Mitra, et al. In situ localized amplification and contact replication of many individual DNA molecules. Nucleic Acids Res. Dec. 15, 1999;27(24):e34.
Narang, et al., Improved Phosphotriester Method for the Synthesis of Gene Fragments. Methods in enzymology. 1979. 68:90-98.
Nuwaysir, et al., Gene expression analysis using oligonucleotide arrays produced by maskless photolithography. Genome Res. 2002. 12, 1749-1755.
Office action dated Mar. 28, 2017 for CN Application No. 201480074638.8.
Olivier, et al. Surface-initiated controlled polymerization as a convenient method for designing functional polymer brushes: From self-assembled monolayers to patterned surfaces. Progress in polymer science. 2012; 37.1: 157-181.

(56) References Cited

OTHER PUBLICATIONS

Orski, et al. High Density Scaffolding of Functional Polymer Brushes: Surface Initiated Atom Transfer Radical Polymerization of Active Esters. Langmuir. 2010; 26(3): 2136-2143.
Pauwels et al., Biological activity of new 2-5A analogues. Chemica scripta. 1986. 26: 141-145.
Payne, et al., MolecularThreading:M echanicalExtraction,Stretching and Placem entofD N A Moleculesfrom a Liquid-AirInterface. PLoS ONE 8(7): e69058.
Premier Biosoft. Accelerating research in life sciences. 1994. Available at http://www.premierbiosoft.com/netprimer/index.html. Accessed on Oct. 18, 2016.
Proudnikov, et al. Immobilization of DNA in polyacrylamide gel for the manufacture of DNA and DNA-oligonucleotide microchips. Anal Biochem. May 15, 1998;259(1):34-41.
Prucker, et al. Polymer Layers through Self-Assembled Monolayers of Initiators. Langmuir. 1998; 14(24): 6893-6898.
Rawls, et al. Optimistic about antisense: promising clinical results and chemical strategies for further improvements delight antisense drug researchers. C&EN.1997. 35-39.
Rehman, et al. Immobilization of acrylamide-modified oligonucleotides by co-polymerization. Nucleic Acids Res. Jan. 15, 1999;27(2):649-55.
Reisner, et al. DNA confinement in nanochannels: physics and biological applications. Rep. Prog. Phys. 2012.75:10.
Rodriguez-Emmenegger, et al. Substrate-independent approach for the generation of functional protein resistant surfaces. Biomacromolecules. Apr. 11, 2011;12(4):1058-66. doi: 10.1021/bm101406m. Epub Mar. 25, 2011.
Ruhe, et al. Functional Polymer Brushes. Journal of Macromolecular Science, Part C: Polymer Reviews. 2002; 42.1: 91-138.
Seiffert, S. & Oppermann, W. Amine-Functionalized Polyacrylamide for Labeling and Crosslinking Purposes. Macromolecular Chemistry and Physics 208, 1744-1752, (2007).
Senaratne, et al. Self-assembled monolayers and polymer brushes in biotechnology: current applications and future perspectives. Biomacromolecules. 2005; 6.5: 2427-2448.
Shapero, et al. SNP genotyping by multiplexed solid-phase amplification and fluorescent minisequencing. Genome Res. Nov. 2001;11(11):1926-34.
Soni, et al., Progress toward ultrafast DNA sequencing using solid-state nanopores. Clin Chem. Nov. 2007; 53(11):1996-2001. Epub Sep. 21, 2007.
Sprinzl, et al., Enzymatic Incorporation of ATP and CTP Analogues into the 3' End of tRNA. Eur. J. Biochem. 81, 579-589 (1977).
Thomson, et al. Oligonucleotide and polymer functionalized nanoparticles for amplification-free detection of DNA. Biomacromolecules. Jun. 11, 2012;13(6):1981-9. doi: 10.1021/bm300717f. Epub May 30, 2012.
Timofeev, et al. Regioselective immobilization of short oligonucleotides to acrylic copolymer gels. Nucleic Acids Res. Aug. 15, 1996;24(16):3142-8.

United Kingdom combined search and examination report dated Jul. 3, 2017 for GB1613408.
Walker et al., Strand displacement amplification—an isothermal,in vitroDNA amplification technique. Nucl. Acids Res. (1992) 20 (7): 1691-1696. doi: 10.1093/nar/20.7.1691.
Wang et al., Stretching DNA with optical tweezers. Biophys J. Mar. 1997; 72(3): 1335-1346.
Westin et al., Anchored multiplex amplification on a microelectronic chip array. Nature Biotechnology 18,199-204(2000).
Yuan, et al. Polymer-functionalized silica nanosphere labels for ultrasensitive detection of tumor necrosis factor-alpha. Anal Chem. Sep. 1, 2011;83(17):6800-9. doi: 10.1021/ac201558w. Epub Aug. 15, 2011.
Zhang, et al., Assembly of Highly Aligned DNA Strands onto Si Chips Langmuir,2005,21(9),pp. 4180-4184.
Zhang, et al., Preparation of megabase-sized DNA from a variety of organisms using the nuclei method for advanced genomics research. Nature Protocols 7, 467-478 (2012).
Mardis. Next-generation DNA sequencing methods. Annu Rev Genomics Hum Genet. 2008;9:387-402. doi: 10.1146/annurev.genom. 9.081307.164359.
Allemand, J. F., Bensimon, D., Jullien, L., Bensimon, A. & Croquette, V. pH-dependent specific binding and combing of DNA. Biophys J 73, 2064-2070, (1997).
Bolli, et al. α-Bicyclo-DNA: Synthesis, Characterization, and Pairing Properties of α-DNA-Analogues with Restricted Conformational Flexibility in the Sugar—Phosphate Backbone. Carbohydrate Modifications in Antisense Research. ACS Symposium Series, vol. 580. Chapter 7, pp. 100-117.
Compton. Nucleic acid sequence-based amplification. Nature. Mar. 7, 1991;350(6313):91-2.
Dempcy et al. Synthesis of a thymidyl pentamer of deoxyribonucleic guanidine and binding studies with DNA homopolynucleotides PNAS US 92:6097-6101 (1995).
Herdewijn, et al. Hexopyranosyl-Like Oligonucleotides. Carbohydrate Modifications in Antisense Research. ACS Symposium Series, vol. 580. Chapter 6, pp. 80-99.
Maddry, et al. Synthesis of Nonionic Oligonucleotide Analogues. Carbohydrate Modifications in Antisense Research. ACS Symposium Series, vol. 580. Chapter 3, pp. 40-51.
Mesmaeker, et al. Novel Backbone Replacements for Oligonucleotides. Carbohydrate Modifications in Antisense Research. ACS Symposium Series, vol. 580. Chapter 2, pp. 24-39.
EP14867116.7 Office Action dated Aug. 31, 2018.
EP14867494.8 Office Action dated Aug. 30, 2018.
CN201480074638.8 Office Action dated Jul. 12, 2018 (w/ English translation).
Office action dated Jul. 17, 2018 for U.S. Appl. No. 15/101,168.
Office Action dated Nov. 3, 2017 for CN Patent Application No. 201480074638.8 (w/ English translation).
U.S. Appl. No. 15/178,411 Office Action dated Apr. 19, 2018.

\* cited by examiner

FIG. 21
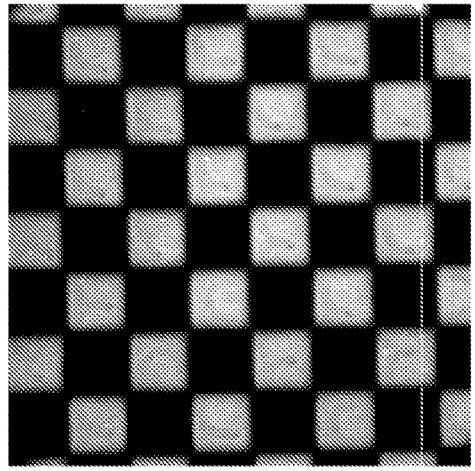
10x 0.5s 10 bin
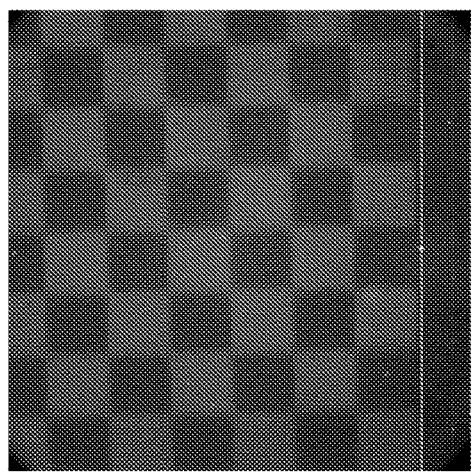
10x 2S 2 bin 100 ms, 2bin
Cluster Number Ratio:
Approximately 1:50

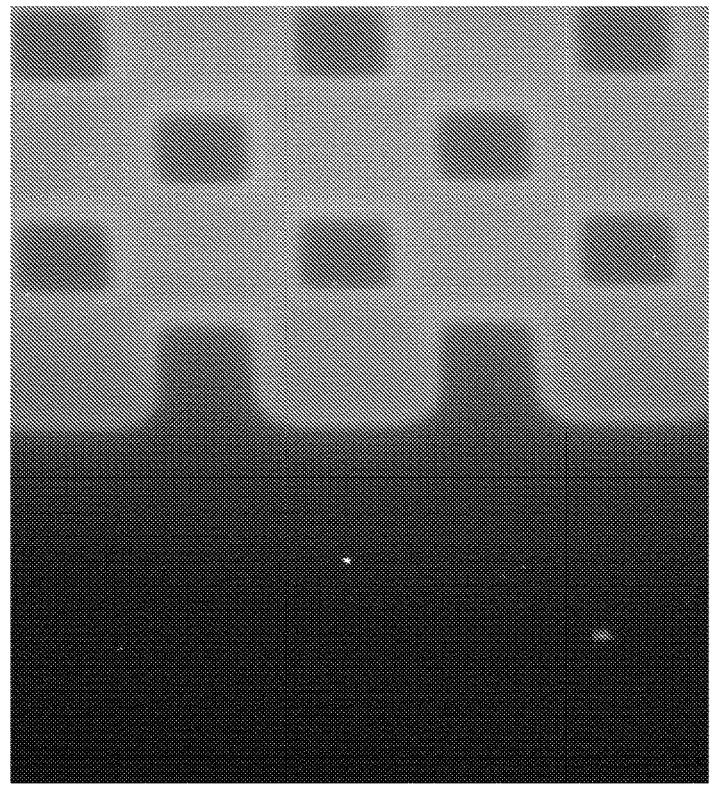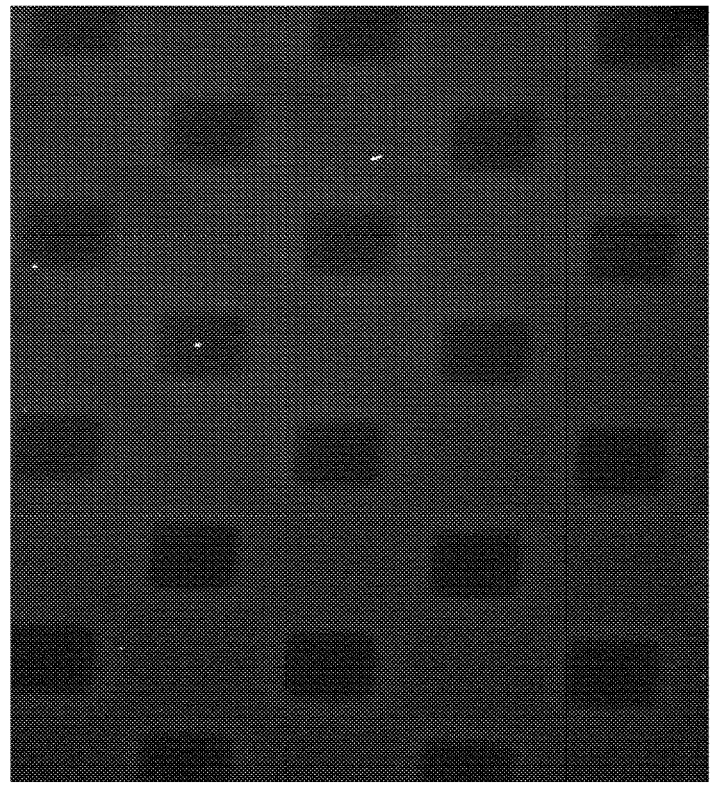
FIG. 30

FABRICATION OF PATTERNED ARRAYS

CROSS-REFERENCE

This application claims the benefit of U.S. Provisional Application Nos. 61/912,027, filed on Dec. 5, 2013, 61/971,542, filed on Mar. 28, 2014, 61/979,448, filed on Apr. 14, 2014, and 62/012,238 filed Jun. 13, 2014, each of which is herein incorporated by reference in its entirety.

BACKGROUND OF THE INVENTION

Patterned arrays have many applications in genomics and molecular diagnostics. Many array manufacturing methods, however, create poor quality probes, partial probes, probes in wrong orientation for extension reactions or on a surface that is not very efficient for enzymatic reactions. This disclosure provides methods and compositions with enzymatically-compatible surfaces, higher-quality probes, and probes in various orientations.

SUMMARY OF THE INVENTION

Methods, compositions and systems are provided for fabricating patterned oligonucleotide arrays that result in high quality full length probes in desired orientations and at a low cost. In some embodiments, patterned oligonucleotide arrays are fabricated using enzymatic transfer wherein primers from a recipient surface is hybridized to a template on a template surface and polymerase drive extension reaction using the template produces a second strand. After separation of the two surfaces, the recipient surface contains a copied oligonucleotide pattern, complementary to the first surface pattern. Alternatively, the template can be hybridized with primers that contain a linker that can be used to immobilize them to the recipient surface. The primer can then be extended and immobilized on to the recipient surface, such as by forming a thin layer of polymer gel on the recipient surface. The resulting copied features can be enhanced by amplification such as bridge amplification. Amplified probes containing adaptor at the 3' end can be enzymatically processed to remove the adaptor sequence.

In one aspect, provided herein is a method for generating an array comprising: providing a template array comprising at least 1,000 different oligonucleotides coupled thereto, coupling said template array to a recipient array having a plurality of oligonucleotides complementary to portions of the at least 1,000 different oligonucleotides, and performing an enzymatic reaction while the template array and the enzymatic array are coupled to one another, thereby generating a recipient array comprising recipient oligonucleotides, wherein at least 40% of the recipient oligonucleotides are complementary or identical to a full-length oligonucleotide from the at least 1,000 different oligonucleotides. In some cases, the template array comprises at least 100 spots. In some cases, the template array comprises spots at most about 500 µm in size. In some cases, the directionality of the recipient oligonucleotides relative to the recipient array is the same as the directionality of the template oligonucleotides relative to the template array. In some cases, the directionality of the recipient oligonucleotides relative to the recipient array is the opposite of the directionality of the template oligonucleotides relative to the template array. In some cases, a plurality of recipient arrays are generated. In some cases, the plurality of recipient oligonucleotides are on average at least 99% identical between one recipient array and another. In some cases, the recipient oligonucleotides are at least 99% identical between one recipient array and another.

In one aspect, provided herein is a method for generating an array comprising: using a template array comprising template oligonucleotides to synthesize a recipient array comprising recipient oligonucleotides wherein the recipient array is coupled to the template array during the synthesis. In some cases, at least 40% of the recipient oligonucleotides comprise full-length products. In some cases, at least 50% of the recipient oligonucleotides comprise full-length products. In some cases, at least 60% of the recipient oligonucleotides comprise full-length products. In some cases, the directionality of the recipient oligonucleotides relative to the recipient array is the same as the directionality of the template oligonucleotides relative to the template array. In some cases, the directionality of the recipient oligonucleotides relative to the recipient array is the opposite of the directionality of the template oligonucleotides relative to the template array. In some cases, a plurality of recipient arrays are generated. In some cases, the plurality of recipient oligonucleotides are on average at least 99% identical between one recipient array and another. In some cases, the recipient oligonucleotides are at least 99% identical between one recipient array and another. In some cases, the template array is physically separated from each of the recipient arrays after synthesis of each of the recipient arrays. In some cases, the template array is separated from each of the recipient arrays after synthesis of each of the recipient arrays by increased temperature. In some cases, the template array comprises at least 100 spots. In some cases, the template array comprises spots at most about 500 µm in size. In one aspect, provided herein is a method for generating a complementary array comprising: (a) providing a plurality of template oligonucleotides coupled to a first substrate, each of said plurality of template oligonucleotides comprising an adaptor sequence, wherein said adaptor sequence is the same for each of said plurality of template oligonucleotides; (b) providing a plurality of recipient oligonucleotides coupled to a second substrate, each of said plurality of recipient oligonucleotides comprising sequence complementary to said adaptor sequence; (c) hybridizing said adaptor sequence of said template oligonucleotides and said sequence complementary to said adaptor sequence of said recipient oligonucleotides; and (d) conducting extension reactions on said plurality of recipient oligonucleotides using said plurality of template oligonucleotides as templates. In some cases, each of said adaptor sequences is located at or near the 3' end of said template oligonucleotides. In some cases, each of said adaptor sequences is located at or near the 5' end of said template oligonucleotides. In some cases, either of said substrates comprises polymer. In some cases, either of said substrates comprises acrylamide or polyacrylamide. In some cases, the conducting step results in generation of recipient oligonucleotides at least 40% of which are full-length products. In some cases, the conducting step results in generation of recipient oligonucleotides at least 50% of which are full-length products. In some cases, the conducting step results in generation of recipient oligonucleotides at least 60% of which are full-length products. In some cases, the directionality of the recipient oligonucleotides relative to the second substrate is the same as the directionality of the template oligonucleotides relative to the first substrate. In some cases, the directionality of the recipient oligonucleotides relative to the second substrate is the opposite of the directionality of the template oligonucleotides relative to the first substrate. In some cases, the method is repeated to produce at least 2 recipient arrays. In some cases, the template array comprises at least 100 spots. In some cases, the template array comprises spots at most about 500 µm in size.

In one aspect, provided herein is a method for transferring an array, comprising: (a) providing a substrate comprising a plurality of linker sites; (b) providing an array comprising a plurality of template oligonucleotides; (c) applying reaction mix to said array, said reaction mix comprising enzyme, dNTPs, and a plurality of linker oligonucleotides comprising sequence complementary to an adaptor sequence appended to each of said plurality of template oligonucleotides and further comprising linker molecules capable of binding to said plurality of linker sites; (d) conducting extension reactions of said plurality of said linker oligonucleotides using said plurality of template oligonucleotides as templates, thereby generating a plurality of extension products comprising said linker molecules; (e) contacting said array with said substrate; and (f) linking said linker molecules of said plurality of extension products to said linker sites. In some cases, said adaptor sequence is located at or near the 3' end of said template oligonucleotides. In some cases, said adaptor sequence is located at or near the 5' end of said template oligonucleotides. In some cases, said substrate comprises polymer. In some cases, said substrate comprises acrylamide or polyacrylamide. In some cases, the template array comprises at least 100 spots. In some cases, the template array comprises spots at most about 500 µm in size.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 21 illustrates gel images with 10× 2 S 2 bin (left) and 10× 0.5 s 10 bin (right).

FIG. 30 illustrates images of Bst-based printing from $1^{st} \rightarrow 2^{nd}$ surface (synthesized 5'→3') synthesized for 1 hr at 55 C. All images were taken with 10 s exposure, 200-2000.

DETAILED DESCRIPTION OF THE INVENTION

I. Overview

Figure 1:
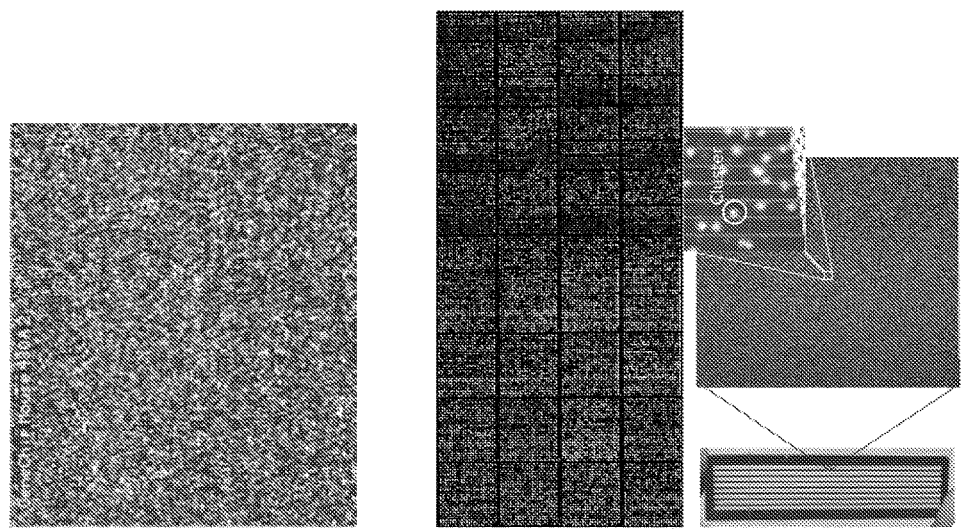
FIG. 1 illustrates examples of different shapes for the template surface.

This disclosure provides methods and compositions for the fabrication and transfer of patterned arrays from a template array to a transfer array. A template array, as used herein refers to a substrate having coupled to it a plurality of polymer molecules such as, e.g., nucleic acids, oligonucleotides or aptamers. A nucleic acid can be an oligonucleotide. Polymers on a template array can be referred to as template polymers, template nucleic acids, template oligomers, template oligonucleotides or template aptamers, as relevant. The template polymer can be double-stranded or can be melted to be single-stranded.

To generate copies of an array with a desired orientation (e.g., 5' end attached to array substrate) a face-to-face gel transfer process may be employed. The face-to-face gel transfer process can significantly reduce the unit cost of fabrication while simultaneously flipping the oligo orientation such that the 5' end is immobilized, which can have assay advantages as described herein. Moreover, the selective transfer of full length oligos and subsequent amplification of the full length oligo can allow the oligo arrays to contain very long oligos (50+ or more bases) without suffering from low yield or partial length products as described herein. The transfer can comprise generation of nucleic acid sequences complementary to the template oligo sequences. The transfer process can occur by enzymatic replication or by non-enzymatic physical transfer of array components between the surfaces. Transfer can comprise fabrication of complementary sequences which are already attached to a recipient/transfer array. For example, primers bound to a recipient/transfer array are complementary to adaptors on the template array and can be extended using the template array sequences as templates to thereby generate a full length or partial length transfer array. Transfer can comprise fabrication of complementary sequences from a template array followed by attachment of the complementary sequences to a transfer array.

Transfer can preserve the orientation of a nucleic acid relative to its coupled array surface (e.g., the 3' end of the template nucleic acid is bound to the template array and the 3' end of the transferred nucleic acid complement is bound to the transfer array). Transfer can reverse the orientation of a nucleic acid relative to its coupled array surface (e.g., the 3' end of the template nucleic acid is bound to the template array and the 5' end of the transferred nucleic acid complement is bound to the transfer array).

In some cases, the array transfer methods described herein are useful in generating transfer or recipient arrays having an increased or enriched amount or percentage of oligonucleotides coupled to the transfer or recipient array surface that are 100% of the length (i.e., a same or identical length) of the respective oligonucleotides on the array used as a template (i.e., template array) for the transfer procedure. The transfer procedure can be a face-to-face enzymatic transfer as provided herein. The face-to-face enzymatic transfer method can also be referred to as enzymatic transfer by synthesis or ETS. Array transfer can result in a transfer or recipient array comprising at least, at most, more than, less than, or about 30%, 40%, 50%, 55%, 60%, 65%, 70%, 75%, 80%, 85%, 90%, 95%, 96%, 97%, 98%, 99%, or 99.9% transferred oligonucleotides that are the same or identical or 100% of the length of the respective oligonucleotide on a template array used to generate the transfer or recipient array. A transferred oligonucleotide that is 100% of the length (i.e., the same or identical length) of a template oligonucleotide can be referred to as full-length product (e.g., full-length product oligo). A template array fabricated by methods known in that art (e.g. spotting or in situ synthesis) can comprise about 20% oligonucleotides that are a desired length (i.e., full-length oligonucleotides) and about 80% oligonucleotides that are not a desired length (i.e., partial-length oligonucleotides). Transfer of the array generated by methods known in the art comprising about 20% full-length oligonucleotides and about 80% partial-length oligonucleotides using array transfer methods as provided herein (e.g., ETS) can result in the generation of transfer or recipient arrays comprising at most about 20% full-length product oligos. A transfer array comprising primers complementary to a sequence at the unbound end of the full-length oligonucleotide on the template array can be used to conduct transfer; Many or all of the partial-length products on the template array comprising about 20% full-length oligonucleotides and about 80% partial-length oligonucleotides lack the unbound end portion of sequence used in array transfer (e.g., ETS) as provided herein and so cannot be transferred. In some cases, an array fabricated according to the methods herein has a greater percentage of oligonucleotides of a desired length (i.e., full length oligos) such that transfer of an array fabricated according to the methods herein using array transfer methods provided herein (i.e., ETS) results in the generation of transfer or recipient arrays with a higher percentage of full-length product oligos as compared to fabrication and transfer methods known in the art. A full-length oligo on an array (e.g., template array) fabricated using the methods provided herein can be about, at most, or at least 10, 15, 20, 25, 30, 35, 40, 45, 50, 55, 60, 65, 70, 75, 80, 85, 90, 95, or 100 bases long. A full length product oligo on a transfer or recipient array transferred using array transfer methods provided herein (i.e., ETS) can be about, at most, or at least 10, 15, 20, 25, 30, 35, 40, 45, 50, 55, 60, 65, 70, 75, 80, 85, 90, 95, or 100 bases long.

Array transfer as provided herein can be performed multiple times. In some cases, a template array (e.g., oligo array) is subjected to an array transfer process a plurality of times. A template array can be subjected to an array transfer process at least, at most, more than, less than or about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, 400, 450, 500, 600, 700, 800, 900, or 1000 times. The array transfer process can be a face-to-face enzymatic transfer method as provided herein. A plurality of transfer or recipient arrays can be generated from multiple array transfers using the same template array. Each transfer or recipient array generated from a single template array using an array transfer method as provided herein can be at least, at most, more than, less than, or about 30%, 40%, 50%, 55%, 60%, 65%, 70%, 75%, 80%, 85%, 90%, 95%, 96%, 97%, 98%, 99%, or 99.9% identical to the template array and/or each other transfer or recipient array generated from the template array. Array transfer can be performed multiple times in a series of transfers, using the transfer array from one array transfer as the template array for a subsequent transfer. For example, a first transfer can be performed from a template array with oligos bound to the array at their 3' ends to a first transfer array with complementary oligos bound to the array at their 5' ends, and a second transfer can be performed from the first transfer array (now serving as a template array) to a second transfer array. In some cases, each progressive transfer or recipient array in a series of array transfer reactions as provided herein generate recipient or transfer arrays with an enriched percentage of full-length product oligos (i.e., a transferred oligonucleotide that is 100% of the length of a template oligonucleotide) and sequences matching the original template array.

In some cases, array transfer can be aided by the use of adaptor sequences on the oligos on the template oligo array. Oligos can comprise a desired final sequence with the addition of one or more adaptor sequences. The one or more adaptor sequences can be on the 5' or 3' end of the oligos on the template array. In some cases, the one or more adaptor sequences are on the 3' end of the oligos on the template array. In some cases, the one or more adaptor sequences are on the 5' end of the oligos on the template array. Primers on a recipient/transfer array can be complementary to adaptor sequences, allowing hybridization between the primers and the oligos (via hybridization to all or a portion of the adaptor sequences) on the template array. Such hybridization can aid in the transfer from one array to another. Some or all adaptor sequences can be removed from transfer array oligos after transfer, for example by enzymatic cleavage, digestion, or restriction.

In some cases, array transfer can be aided by the flexibility or deformability of the array or of a surface coating on the array. For example, an array comprising a polyacrylamide gel coating with coupled oligonucleotides can be used in array transfer. The deformability of the gel coating can allow for array components to contact each other despite surface roughness. The deformability can permit enzymes required in enzymatic array transfer methods (e.g., ETS as provided herein) more effective contact with reaction components as compared to arrays that do not comprise a polyacrylamide gel The more effective contact can permit a higher number of enzymatic transfers as compared to arrays that do not comprise a polyacrylamide gel. The more effective contact can permit the generation of a higher percentage of transfer or recipient arrays comprising oligos that are 100% of the length of the oligos on a template array used in the array transfer method.

Array components can be amplified or regenerated by enzymatic reactions. For example, bridge amplification can be conducted on array component oligonucleotides via hybridization between adaptor sequences on the array components and surface-bound oligonucleotide primers, followed by enzymatic extension or amplification. Amplification can be used to recover lost array component density or to increase density of array components beyond their original density.

II. Nucleic Acids and Sources Thereof

A "nucleic acid molecule" or "nucleic acid" as referred to herein can be deoxyribonucleic acid (DNA) or ribonucleic acid (RNA) including known analogs or a combination thereof unless otherwise indicated. Nucleic acid molecules to be sequenced herein can be obtained from any source of nucleic acid. The nucleic acid molecule can be single-stranded or double-stranded. In some cases, the nucleic acid molecule is DNA. The DNA can be obtained and purified using standard techniques in the art and include DNA in purified or unpurified form. The DNA can be mitochondrial DNA, cell-free DNA, complementary DNA (cDNA), or genomic DNA. In some cases, the nucleic acid molecule is genomic DNA (gDNA). The DNA can be plasmid DNA, cosmid DNA, bacterial artificial chromosome (BAC), or yeast artificial chromosome (YAC). The DNA can be derived from one or more chromosomes. For example, if the DNA is from a human, the DNA can derived from one or more of chromosome 1, 2, 3, 4, 5, 6, 7, 8, 9, 10, 11, 12, 13, 14, 15, 16, 17, 18, 19, 20, 21, 22, X, or Y. The RNA can be obtained and purified using standard techniques in the art and include RNAs in purified or unpurified form, which include, but are not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoRNAs, microRNAs, siRNAs, piRNAs and long nc RNAs.

The source of nucleic acid for use in the methods and compositions described herein can be a sample comprising the nucleic acid. The nucleic acid can be isolated from the sample and purified by any of the methods known in the art for purifying the nucleic acid from the sample. The sample can be derived from a non-cellular entity comprising polynucleotides (e.g., a virus) or from a cell-based organism (e.g., member of archaea, bacteria, or eukarya domains). In some cases, the sample is obtained from a swab of a surface, such as a door or bench top.

The sample can be from a subject, e.g., a plant, fungi, eubacteria, archeabacteria, protest, or animal. The subject can be an organism, either a single-celled or multi-cellular organism. The subject can be cultured cells, which can be primary cells or cells from an established cell line, among others. The sample can be isolated initially from a multi-cellular organism in any suitable form. The animal can be a fish, e.g., a zebrafish. The animal can be a mammal. The mammal can be, e.g., a dog, cat, horse, cow, mouse, rat, or pig. The mammal can be a primate, e.g., a human, chimpanzee, orangutan, or gorilla. The human can be a male or female. The sample can be from a human embryo or human fetus. The human can be an infant, child, teenager, adult, or elderly person. The female can be pregnant, suspected of being pregnant, or planning to become pregnant. In some cases, the sample is a single or individual cell from a subject and the polynucleotides are derived from the single or individual cell. In some cases, the sample is an individual micro-organism, or a population of micro-organisms, or a mixture of micro-organisms and host cellular or cell free nucleic acids.

The sample can be from a subject (e.g., human subject) who is healthy. In some cases, the sample is taken from a subject (e.g., an expectant mother) at at least 4, 5, 6, 7, 8, 9, 10, 11, 12, 13, 14, 15, 16, 17, 18, 19, 20, 21, 22, 23, 24, 25, or 26 weeks of gestation. In some cases, the subject is affected by a genetic disease, a carrier for a genetic disease or at risk for developing or passing down a genetic disease, where a genetic disease is any disease that can be linked to a genetic variation such as mutations, insertions, additions, deletions, translocation, point mutation, trinucleotide repeat disorders and/or single nucleotide polymorphisms (SNPs).

The sample can be from a subject who has a specific disease, disorder, or condition, or is suspected of having (or at risk of having) a specific disease, disorder or condition. For example, the sample can be from a cancer patient, a patient suspected of having cancer, or a patient at risk of having cancer. The cancer can be, e.g., acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloepithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chromic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, nonmelanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom Macroglobulinemia, or Wilms Tumor. The sample can be from the cancer and/or normal tissue from the cancer patient.

The sample can be aqueous humour, vitreous humour, bile, whole blood, blood serum, blood plasma, breast milk, cerebrospinal fluid, cerumen, enolymph, perilymph, gastric juice, mucus, peritoneal fluid, saliva, sebum, semen, sweat, tears, vaginal secretion, vomit, feces, or urine. The sample can be obtained from a hospital, laboratory, clinical or medical laboratory. The sample can be taken from a subject.

The sample can be an environmental sample comprising medium such as water, soil, air, and the like. The sample can be a forensic sample (e.g., hair, blood, semen, saliva, etc.). The sample can comprise an agent used in a bioterrorist attack (e.g., influenza, anthrax, smallpox).

The sample can comprise nucleic acid. The sample can comprise cell-free nucleic acid. The sample can be a cell line, genomic DNA, cell-free plasma, formalin fixed paraffin embedded (FFPE) sample, or flash frozen sample. A formalin fixed paraffin embedded sample can be deparaffinized before nucleic acid is extracted. The sample can be from an organ, e.g., heart, skin, liver, lung, breast, stomach, pancreas, bladder, colon, gall bladder, brain, etc. Nucleic acids can be extracted from a sample by means available to one of ordinary skill in the art.

The sample can be processed to render it competent for fragmentation, ligation, denaturation, amplification, stretching, and/or sequencing or any of the methods provided herein. Exemplary sample processing can include lysing cells of the sample to release nucleic acid, purifying the sample (e.g., to isolate nucleic acid from other sample components, which can inhibit enzymatic reactions), diluting/concentrating the sample, and/or combining the sample with reagents for further nucleic acid processing. In some examples, the sample can be combined with a restriction enzyme, reverse transcriptase, or any other enzyme of nucleic acid processing.

The methods described herein can be used for sequencing one or more target nucleic acids or polynucleotides. A polynucleotide described herein can contain phosphodiester bonds, although in some cases, as outlined below (for example in the construction of primers and probes such as label probes), nucleic acid analogs are included that can have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 120.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469, 863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-O atom with the 4'-C atom. All of these references are hereby expressly incorporated by reference. These modifications of the ribose-phosphate backbone can be done to increase the stability and half-life of such molecules in physiological environments. For example, PNA:DNA and LNA-DNA hybrids can exhibit higher stability and thus can be used in some cases. The nucleic acids can be single stranded or double stranded, as specified, or contain portions of both double stranded or single stranded sequence. Depending on the application, the nucleic acids can be DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

A "nucleic acid molecule" or "nucleic acid" as referred to herein can be an "oligonucleotide" "aptamer" or a "polynucleotide". The term "oligonucleotide" can refer to a nucleotide chain, typically less than 200 residues long, e.g., between 15 and 100 nucleotides long. The oligonucleotide can comprise at least or about 1, 2, 3, 4, 5, 6, 7, 8, 9, 10, 15, 20, 25, 30, 35, 40, 45, or 50 bases. The oligonucleotides can be from about 3 to about 5 bases, from about 1 to about 50 bases, from about 8 to about 12 bases, from about 15 to about 25 bases, from about 25 to about 35 bases, from about 35 to about 45 bases, or from about 45 to about 55 bases. The oligonucleotide (also referred to as "oligo") can be any type of oligo (e.g., primer). In some cases, the oligos are 5'-acrydite-modified oligos. The oligos can be coupled to the polymer coatings as provided herein on surfaces as provided herein. The oligonucleotides can comprise cleavable linkages. Cleavable linkages can be enzymatically cleavable. Oligonucleotides can be single- or double-stranded. The terms "primer" and "oligonucleotide primer" can refer to an oligonucleotide capable of hybridizing to a complementary nucleotide sequence. The term "oligonucleotide" can be used interchangeably with the terms "primer," "adapter," and "probe." The term "polynucleotide" can refer to a nucleotide chain typically greater than 200 residues long. Polynucleotides can be single- or double-stranded.

The term "hybridization"/"hybridizing" and "annealing" can be used interchangeably and can refer to the pairing of complementary nucleic acids.

The term "primer" can refer to an oligonucleotide, generally with a free 3' hydroxyl group, that is capable of hybridizing with a template nucleic acid or nucleic acid molecule (such as a target polynucleotide, target DNA, target RNA or a primer extension product) and is also capable of promoting polymerization of a polynucleotide complementary to the template. A primer can contain a non-hybridizing sequence that constitutes a tail of the primer. A primer can still be hybridizing to a target even though its sequences may not be fully complementary to the target.

Primers can be oligonucleotides that can be employed in an extension reaction by a polymerase along a polynucleotide template, such as in PCR or cDNA synthesis, for example. The oligonucleotide primer can be a synthetic polynucleotide that is single stranded, containing a sequence at its 3'-end that is capable of hybridizing with a sequence of the target polynucleotide. Normally, the 3' region of the primer that hybridizes with the target nucleic acid has at least 80%, 90%, 95%, or 100%, complementarity to a sequence or primer binding site.

Primers can be designed according to known parameters for avoiding secondary structures and self-hybridization. Different primer pairs can anneal and melt at about the same temperatures, for example, within about 1, 2, 3, 4, 5, 6, 7, 8, 9 or 10° C. of another primer pair. In some cases, greater than about 1, 2, 3, 4, 5, 6, 7, 8, 9, 10, 15, 20, 25, 30, 35, 40, 45, 50, 100, 200, 500, 1000, 5000, 10,000 or more primers are initially used. Such primers may be able to hybridize to the genetic targets described herein. In some cases, about 2 to about 10,000, about 2 to about 5,000, about 2 to about 2,500, about 2 to about 1,000, about 2 to about 500, about 2 to about 100, about 2 to about 50, about 2 to about 20, about 2 to about 10, or about 2 to about 6 primers are used.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Integrated DNA Technologies, Operon Technologies, Amersham Pharmacia Biotech, Sigma, and Life Technologies. The primers can have an identical melting temperature. The melting temperature of a primer can be about, more than, less than, or at least 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 81, 82, 83, 84, or 85° C. In some cases, the melting temperature of the primer is about 30 to about 85° C., about 30 to about 80° C., about 30 to about 75° C., about 30 to about 70° C., about 30 to about 65° C., about 30 to about 60° C., about 30 to about 55° C., about 30 to about 50° C., about 40 to about 85° C., about 40 to about 80° C., about 40 to about 75° C., about 40 to about 70° C., about 40 to about 65° C., about 40 to about 60° C., about 40 to about 55° C., about 40 to about 50° C., about 40 to about 85° C., about 50 to about 80° C., about 50 to about 75° C., about 50 to about 70° C., about 50 to about 65° C., about 50 to about 60° C., about 50 to about 55° C., about 52 to about 60° C., about 52 to about 58° C., about 52 to about 56° C., or about 52 to about 54° C.

The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The $T_M$ (melting or annealing temperature) of each primer can be calculated using software programs such as Net Primer (free web based program at http://www.premierbiosoft.com/netprimer/index.html). The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5' half of the primers can be incorporated into the products from each loci of interest; thus the $T_M$ can be recalculated based on both the sequences of the 5' half and the 3' half of each primer.

The annealing temperature of the primers can be recalculated and increased after any cycle of amplification, including but not limited to about cycle 1, 2, 3, 4, 5, about cycle 6 to about cycle 10, about cycle 10 to about cycle 15, about cycle 15 to about cycle 20, about cycle 20 to about cycle 25, about cycle 25 to about cycle 30, about cycle 30 to about cycle 35, or about cycle 35 to about cycle 40. After the initial cycles of amplification, the 5' half of the primers can be incorporated into the products from each loci of interest, thus the TM can be recalculated based on both the sequences of the 5' half and the 3' half of each primer.

"Complementary" can refer to complementarity to all or only to a portion of a sequence (e.g., template nucleic acid). The number of nucleotides in the hybridizable sequence of a specific oligonucleotide primer should be such that stringency conditions used to hybridize the oligonucleotide primer will prevent excessive random non-specific hybridization. Usually, the number of nucleotides in the hybridizing portion of the oligonucleotide primer will be at least as great as the defined sequence on the target polynucleotide (e.g., template nucleic acid) that the oligonucleotide primer hybridizes to, namely, at least 5, at least 6, at least 7, at least 8, at least 9, at least 10, at least 11, at least 12, at least 13, at least 14, at least 15, at least about 20, and generally from about 6 to about 10 or 6 to about 12 of 12 to about 200 nucleotides, usually about 10 to about 50 nucleotides. A target polynucleotide can be larger than an oligonucleotide primer or primers as described previously.

The term "about" or "nearly" as used herein refers to within +/−10%, 9%, 8%, 7%, 6%, 5%, 4%, 3%, 2%, or 1% of the designated amount. For example, "nearly identical" can mean at least a 90%, 91%, 92%, 93%, 94%, 95%, 96%, 97%, 98%, or 99% identity.

In some cases, a set of barcodes is provided. The term "barcode" can refer to a known nucleic acid sequence that allows some feature of a nucleic acid (e.g., oligo) with which the barcode is associated to be identified. In some cases, the feature of the nucleic acid to be identified is the spatial position of each nucleic acid (e.g., oligo) on an array or chip. The barcodes can be designed for precision sequence performance, e.g., GC content between 40% and 60%, no homo-polymer runs longer than two, no self-complementary stretches longer than 3, and be comprised of sequences not present in a human genome reference. A barcode sequence can be at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. A barcode sequence can be at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. A barcode sequence can be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 bases. An oligonucleotide (e.g., primer or adapter) can comprise about, more than, less than, or at least 1, 2, 3, 4, 5, 6, 7, 8, 9, or 10 different barcodes. Barcodes can be of sufficient length and comprise sequences that can be sufficiently different to allow the identification of the spatial position of each nucleic acid (e.g., oligo) based on barcode(s) with which each nucleic acid is associated. In some cases, each barcode is, for example, four deletions or insertions or substitutions away from any other barcode in an array. The oligos in each array spot on the barcoded oligo array can comprise the same barcode sequence and oligos in different array spots can comprise different barcode sequences. The barcode sequence used in one array spot can be different from the barcode sequence in any other array spot. Alternatively, the barcode sequence used in one array spot can be the same as the barcode sequence used in another array spot, as long as the two array spots are not adjacent. Barcode sequences corresponding to particular array spots can be known from the controlled synthesis of the array. Alternatively, barcode sequences corresponding to particular array spots can be known by retrieving and sequencing material from particular array spots. A candidate set of barcodes containing 1.5 million 18 base barcodes was designed as an example.

III. Enzymes

RNA-dependent DNA polymerases for use in the methods and compositions provided herein can be capable of effecting extension of a primer according to the methods provided herein. Accordingly, an RNA-dependent DNA polymerase can be one that is capable of extending a nucleic acid primer along a nucleic acid template that is comprised at least predominantly of ribonucleotides. Suitable RNA-dependent DNA polymerases for use in the methods, compositions, and kits provided herein include reverse transcriptases (RTs). RTs are well known in the art. Examples of RTs include, but are not limited to, Moloney murine leukemia virus (M-MLV) reverse transcriptase, human immunodeficiency virus (HIV) reverse transcriptase, rous sarcoma virus (RSV) reverse transcriptase, avian myeloblastosis virus (AMV) reverse transcriptase, rous associated virus (RAV) reverse transcriptase, and myeloblastosis associated virus (MAV) reverse transcriptase or other avian sarcoma-leukosis virus (ASLV) reverse transcriptases, and modified RTs derived therefrom. See e.g. U.S. Pat. No. 7,056,716. Many reverse transcriptases, such as those from avian myeoloblastosis virus (AMV-RT), and Moloney murine leukemia virus (MMLV-RT) comprise more than one activity (for example, polymerase activity and ribonuclease activity) and can function in the formation of the double stranded cDNA molecules. However, in some instances, it is preferable to employ a RT which lacks or has substantially reduced RNase H activity. RTs devoid of RNase H activity are known in the art, including those comprising a mutation of the wild type reverse transcriptase where the mutation eliminates the RNase H activity. Examples of RTs having reduced RNase H activity are described in US20100203597. In these cases, the addition of an RNase H from other sources, such as that isolated from E. coli, can be employed for the degradation of the starting RNA sample and the formation of the double stranded cDNA. Combinations of RTs can also contemplated, including combinations of different non-mutant RTs, combinations of different mutant RTs, and combinations of one or more non-mutant RT with one or more mutant RT.

DNA-dependent DNA polymerases for use in the methods and compositions provided herein can be capable of effecting extension of a primer according to the methods provided herein. Accordingly, a DNA-dependent DNA polymerase can be one that is capable of extending a nucleic acid primer along a first strand cDNA in the presence of the RNA template or after selective removal of the RNA template. Exemplary DNA dependent DNA polymerases suitable for the methods provided herein include but are not limited to Klenow polymerase, with or without 3'-exonuclease, Bst DNA polymerase, Bca polymerase, .phi.29 DNA polymerase, Vent polymerase, Deep Vent polymerase, Taq polymerase, T4 polymerase, and E. coli DNA polymerase 1, derivatives thereof, or mixture of polymerases. In some cases, the polymerase does not comprise a 5'-exonuclease activity. In other cases, the polymerase comprises 5' exonuclease activity. In some cases, the primer extension can be performed using a polymerase comprising strong strand displacement activity such as for example Bst polymerase. In other cases, the primer extension can be performed using a polymerase comprising weak or no strand displacement activity. One skilled in the art can recognize the advantages and disadvantages of the use of strand displacement activity during the primer extension step, and which polymerases can be expected to provide strand displacement activity (see e.g., New England Biolabs Polymerases). For example, strand displacement activity can be useful in ensuring whole transcriptome coverage during the random priming and extension step. Strand displacement activity can further be useful in the generation of double stranded amplification products during the priming and extension step. Alternatively, a polymerase which comprises weak or no strand displacement activity can be useful in the generation of single stranded nucleic acid products during primer hybridization and extension that can be hybridized to the template nucleic acid.

In some cases, any double stranded product generated by the methods described herein can be end repaired to produce blunt ends for the adapter ligation applications described herein. Generation of the blunt ends on the double stranded products can be generated by the use of a single strand specific DNA exonuclease such as for example exonuclease 1, exonuclease 7 or a combination thereof to degrade overhanging single stranded ends of the double stranded products. Alternatively, any double stranded products generated by methods provided herein can be blunt ended by the use of a single stranded specific DNA endonuclease for example but not limited to mung bean endonuclease or S1 endonuclease. Alternatively, any double stranded products generated by methods provided herein can be blunt ended by the use of a polymerase that comprises single stranded exonuclease activity such as for example T4 DNA polymerase, any other polymerase comprising single stranded exonuclease activity or a combination thereof to degrade the overhanging single stranded ends of the double stranded products. In some cases, the polymerase comprising single stranded exonuclease activity can be incubated in a reaction mixture that does or does not comprise one or more dNTPs. In other cases, a combination of single stranded nucleic acid specific exonucleases and one or more polymerases can be used to blunt end the double stranded products of the primer extension reaction. In still other cases, the products of the extension reaction can be made blunt ended by filling in the overhanging single stranded ends of the double stranded products. For example, the fragments can be incubated with a polymerase such as T4 DNA polymerase or Klenow polymerase or a combination thereof in the presence of one or more dNTPs to fill in the single stranded portions of the double stranded products. Alternatively, any double stranded products generated by methods provided herein can be made blunt by a combination of a single stranded overhang degradation reaction using exonucleases and/or polymerases, and a fill-in reaction using one or more polymerases in the presence of one or more dNTPs.

In another embodiment, the adapter ligation applications described herein can leave a gap between a non-ligation strand of the adapters and a strand of the double stranded product. In these instances, a gap repair or fill-in reaction can be used to append the double stranded product with the sequence complementary to the ligation strand of the adapter. Gap repair can be performed with any number of DNA dependent DNA polymerase described herein. In some cases, gap repair can be performed with a DNA dependent DNA polymerase with strand displacement activity. In some cases, gap repair can be performed using a DNA dependent DNA polymerase with weak or no strand displacement activity. In some cases, the ligation strand of the adapter can serve as the template for the gap repair or fill-in reaction. In some cases, gap repair can be performed using Taq DNA polymerase.

Various ligation processes and reagents are known in the art and can be useful for carrying out the methods provided herein. For example, blunt ligation can be employed. Similarly, a single dA nucleotide can be added to the 3'-end of the double-stranded DNA product, by a polymerase lacking 3'-exonuclease activity and can anneal to an adapter comprising a dT overhang (or the reverse). This design allows the hybridized components to be subsequently ligated (e.g., by T4 DNA ligase). Other ligation strategies and the corresponding reagents and known in the art and kits and reagents for carrying out efficient ligation reactions are commercially available (e.g, from New England Biolabs, Roche).

The terms "joining," "appending" and "ligation" as used herein, with respect to two polynucleotides, such as a stem-loop adaptor/primer oligonucleotide and a target polynucleotide, refers to the covalent attachment of two separate polynucleotides to produce a single larger polynucleotide with a contiguous backbone. Methods for joining two polynucleotides are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, which are herein incorporated by reference. In some embodiments, an adaptor oligonucleotide is joined to a target polynucleotide by a ligase, for example a DNA ligase or RNA ligase. Multiple ligases, each having characterized reaction conditions, are known in the art, and include, without limitation $NAD^+$-dependent ligases including tRNA ligase, Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof. Ligation can be between polynucleotides having hybridizable sequences, such as complementary overhangs. Ligation can also be between two blunt ends. Generally, a 5' phosphate is utilized in a ligation reaction. The 5' phosphate can be provided by the target polynucleotide, the adaptor oligonucleotide, or both. 5' phosphates can be added to or removed from polynucleotides to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases.

IV. Methods of Amplification

The methods, compositions and kits described herein can be useful to generate amplification-ready products for downstream applications such as massively parallel sequencing (i.e. next generation sequencing methods) or hybridization platforms. Methods of amplification are well known in the art. Examples of PCR techniques that can be used include, but are not limited to, quantitative PCR, quantitative fluorescent PCR (QF-PCR), multiplex fluorescent PCR (MF-PCR), real time PCR(RT-PCR), single cell PCR, restriction fragment length polymorphism PCR(PCR-RFLP), PCR-RFLP/RT-PCR-RFLP, hot start PCR, nested PCR, in situ polony PCR, in situ rolling circle amplification (RCA), bridge PCR, picotiter PCR, digital PCR, droplet digital PCR, and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA), single primer isothermal amplification (SPIA, see e.g. U.S. Pat. No. 6,251,639), Ribo-SPIA, or a combination thereof. Other amplification methods that can be used herein include those described in U.S. Pat. Nos. 5,242,794; 5,494,810; 4,988,617; and 6,582,938. Amplification of target nucleic acids can occur on a bead. In other embodiments, amplification does not occur on a bead. Amplification can be by isothermal amplification, e.g., isothermal linear amplification. A hot start PCR can be performed wherein the reaction is heated to 95° C. for two minutes prior to addition of the polymerase or the polymerase can be kept inactive until the first heating step in cycle 1. Hot start PCR can be used to minimize nonspecific amplification. Other strategies for and aspects of amplification are described in U.S. Patent Application Publication No. 2010/0173394 A1, published Jul. 8, 2010, which is incorporated herein by reference. In some cases, the amplification methods can be performed under limiting conditions such that only a few rounds of amplification (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 etc.), such as for example as is commonly done for cDNA generation. The number of rounds of amplification can be about 1-30, 1-20, 1-15, 1-10, 5-30, 10-30, 15-30, 20-30, 10-30, 15-30, 20-30, or 25-30.

Techniques for amplification of target and reference sequences are known in the art and include the methods described in U.S. Pat. No. 7,048,481. Briefly, the techniques can include methods and compositions that separate samples into small droplets, in some instances with each containing on average less than about 5, 4, 3, 2, or one target nucleic acid molecule (polynucleotide) per droplet, amplifying the nucleic acid sequence in each droplet and detecting the presence of a target nucleic acid sequence. In some cases, the sequence that is amplified is present on a probe to the genomic DNA, rather than the genomic DNA itself. In some cases, at least 200, 175, 150, 125, 100, 90, 80, 70, 60, 50, 40, 30, 20, 10, or 0 droplets have zero copies of a target nucleic acid.

PCR can involve in vitro amplification based on repeated cycles of denaturation, oligonucleotide primer annealing, and primer extension by thermophilic template dependent polynucleotide polymerase, which can result in the exponential increase in copies of the desired sequence of the polynucleotide analyte flanked by the primers. In some cases, two different PCR primers, which anneal to opposite strands of the DNA, can be positioned so that the polymerase catalyzed extension product of one primer can serve as a template strand for the other, leading to the accumulation of a discrete double stranded fragment whose length is defined by the distance between the 5' ends of the oligonucleotide primers.

LCR uses a ligase enzyme to join pairs of preformed nucleic acid probes. The probes can hybridize with each complementary strand of the nucleic acid analyte, if present, and ligase can be employed to bind each pair of probes together resulting in two templates that can serve in the next cycle to reiterate the particular nucleic acid sequence.

SDA (Westin et al 2000, Nature Biotechnology, 18, 199-202; Walker et al 1992, Nucleic Acids Research, 20, 7, 1691-1696), can involve isothermal amplification based upon the ability of a restriction endonuclease such as HincII or BsoBI to nick the unmodified strand of a hemiphosphorothioate form of its recognition site, and the ability of an exonuclease deficient DNA polymerase such as Klenow exo minus polymerase, or Bst polymerase, to extend the 3'-end at the nick and displace the downstream DNA strand. Exponential amplification results from coupling sense and antisense reactions in which strands displaced from a sense reaction serve as targets for an antisense reaction and vice versa.

In some cases, the amplification is exponential, e.g. in the enzymatic amplification of specific double stranded sequences of DNA by a polymerase chain reaction (PCR).

V. Oligonucleotide Arrays

In some cases, a surface for use in the methods provided herein comprises an oligonucleotides. In some cases, the surfaces are arrays. In some cases, the arrays comprise aptamers. In some cases, the arrays comprise oligonucleotides such that they are oligonucleotide arrays. In some cases, the oligonucleotide or oligo arrays are generated on surfaces comprising polymer coatings as provided herein. The oligo arrays can be high density oligonucleotide arrays. The oligo array can comprise at least 10, 20, 50, 100, 200, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 oligos coupled to a surface as provided herein. The oligo array can comprise at most 10, 20, 50, 100, 200, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 oligos coupled to a surface as provided herein. The oligo array can comprise about 10, 20, 50, 100, 200, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 oligos coupled to a surface as provided herein. An oligo array as provided herein can have oligos arranged on it at a density of at least 10, 20, 50, 100, 200, 500, 1,000, 2,000, 5,000, 10,000, 20,000, 50,000, 100,000, 200,000, 500,000, 1,000,000, 2,000,000, 5,000,000, 10,000,000, 20,000,000, 100,000,000, 200,000,000, 500,000,000 or 1,000,000,000 oligos per square micrometer. The oligos on an oligo array as provided herein can be organized into spots (features), regions, or pixels. Oligos in each spot (feature) or region can be identical to each other or related to each other (e.g., all or substantially all include a consensus or common sequence). Oligos in each spot or region can be greater than 55, 60, 65, 70, 75, 80, 85, 90, 95, 99, or 99.9% identical to each other. An oligo array as provided herein can comprise at least 1, 2, 3, 4, 5, 6, 7, 8, 9, 10, 100, 1000, 10,000, 50,000, 100,000, 200,000, 500,000, 1,000,000, 2,000,000, 5,000,000, 10,000,000, 20,000,000, 100,000,000, 200,000,000, 500,000,000 or 1,000,000,000 spots (features) or regions. Each spot or region can have a size of at most about 1 cm, 1 mm, 500 µm, 200 µm, 100 µm, 10 µm, 9 µm, 8 µm, 7 µm, 6 µm, 5 µm, 4 µm, 3 µm, 2 µm, 1 µm, 800 nm, 500 nm, 300 nm, 100 nm, 50 nm, or 10 nm. In some cases, the oligos are coupled to the polymer coating as provided herein on the surface. The polymer coating can be a polyacrylamide coating as provided herein. In some cases, a composition as provided herein comprises a surface, a polyacrylamide coating covalently bound to said surface; and at least one oligonucleotide coupled to said polyacrylamide coating.

Oligonucleotides (oligos) can be arranged on the array (template and/or recipient array) surface in 5' to 3' orientation or in 3' to 5' orientation. Individual array spots or regions can have dimensions of up to about 15 µm, up to about 14 µm, up to about 13 µm, up to about 12 µm, up to about 11 µm, up to about 10 µm, up to about 5 µm, up to about 3 µm, up to about 1 µm, up to about 0.3 µm, or up to about 0.1 µm. The primer regions can be arranged on the substrate at a density of at least 100, 1,000, 10,000, 100,000, 500,000, 1,000,000, 2,000,000, 5,000,000, 10,000,000, 20,000,000, 50,000,000, 100,000,000, 200,000,000, or 500,000,000 regions per $cm^2$.

In some cases, the oligos are incorporated into the polymer coatings (e.g., polyacrylamide coating) during the polymerization process. For example, 5'-acrydite-modified oligonucleotides chains can be added during the acrylamide polymerization process to allow the incorporation of the oligonucleotides into the polymerizing polyacrylamide structure. In some cases, the oligonucleotides are coupled to the polymer coating (e.g., polyacrylamide coating) at the 5' end. In some cases, the oligonucleotides are coupled to the polymer coating (e.g., polyacrylamide coating) at the 3' end. In some cases, some oligonucleotides are coupled to the polymer coating (e.g., polyacrylamide coating) at the 3' end and some oligonucleotides are coupled to the polymer coating (e.g., polyacrylamide coating) at the 5' end.

In some cases, the oligos are incorporated into the polymer coatings (e.g., polyacrylamide coating) after the polymerization process. For example, reactive sites can be added to the polymer (e.g., polyacrylamide) structure during the polymerization process. Oligos can then be incorporated at the reactive sites subsequent to the polymerization of the polymer (e.g., polyacrylamide). The reactive sites can comprise bromoacetyl site, azide sites, or sites that are compatible with azide-alkyne Huisgen cycloaddition. In some cases, the reactive sites comprise bromoacetyl sites. In some cases, the reactive sites comprise azides. In some cases, the reactive sites comprise sites compatible with azide-alkyne Huisgen cycloaddition.

In some cases, the oligos are incorporated into the polymer coatings (e.g., polyacrylamide coating) in a controlled manner, with particular oligos located at particular regions of the polymer coatings (e.g., polyacrylamide coating). Oligos can be incorporated into the polymer coatings (e.g., polyacrylamide coating) at random, with particular oligos randomly distributed throughout the polymer coatings (e.g., polyacrylamide coating).

The oligo array for use as a template array for the methods provided herein can be fabricated by any appropriate method, including but, not limited to, spotting and in situ synthesis. The methods can include, but are not limited to, in situ synthesis (e.g., photo-directed synthesis), printing (e.g., ink jet printing), spotting, transfer, bridge amplification, or recombinase polymerase amplification. The substrate of the template array and of the transfer array can be any appropriate material, including but not limited to glass, silicon, and polymers such as polyacrylamide, polystyrene, polymethylmethacrylate (PMMA), and polydimethylsiloxane (PDMS). The substrate of the template array and of the transfer array can be the same or can be different.

In some cases, oligo arrays (i.e., template arrays) for use in the methods provided herein are synthesized by spotting. Spotting can be as described in Gao et al., 2004, *Biopolymers*, 73(5):579-596, the disclosure of which is herein incorporated by reference in its entirety. Noncontact or contact printing methods (e.g., robotic pins, piezoelectric ink jet printers) can be used to deposit pre-synthesized oligos onto oligo or primer regions of the array. Oligos can then be linked or immobilized to the surface, for example by chemical attachment via a functional group. In some cases, the functional group can be bound to the 5' end of the oligo, resulting in oligos with 3' ends away from the surface.

In some cases, oligo arrays (i.e., template arrays) are generated using bridge amplification or recombinase polymerase amplification, for example as described herein as well as in U.S. Provisional Application No. 61/979,448 or 62/012,238, the disclosure of each of which is herein incorporated by reference in its entirety. A substrate for the oligo array (i.e., template array) can comprise bound adaptors or oligos capable of binding to a region on a separate oligo, permitting bridge amplification or recombinase polymerase amplification of the separate oligo on the substrate. The substrate can be seeded with oligos (i.e., primers) with known barcode sequences, followed by amplification to generate oligo regions. Alternatively, the oligo substrate (i.e., template array substrate) can be seeded with oligos with random or unknown barcode sequences, followed by amplification to generate oligo regions and sequencing of oligos from each oligo region to determine the barcode sequence corresponding to each oligo region. The substrate can be prepared for the generation of oligo arrays as provided herein.

VI. Transfer Techniques

The present disclosure provides methods and compositions for transfer of template polymers. Transfer of the template polymer array to a second surface can occur via an array transfer step.

Figure 4:
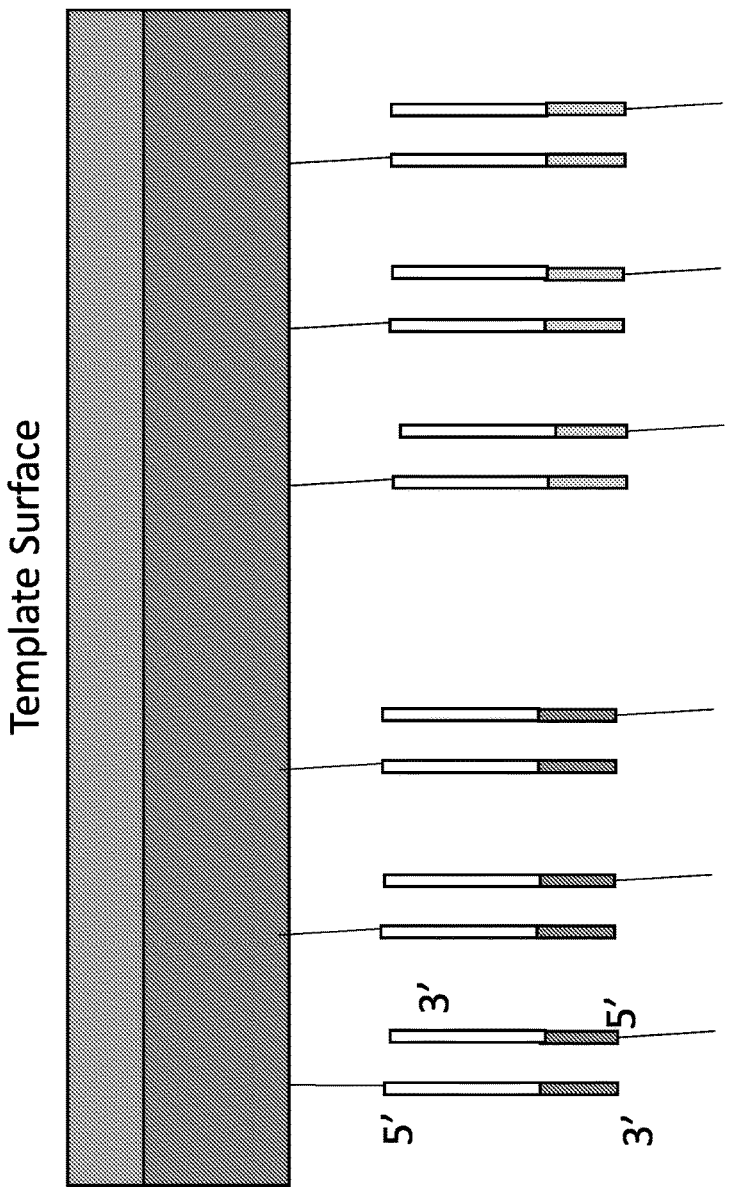
FIG. 4 illustrates a schematic of a first stage of oligonucleotide immobilization transfer (OIT).
Figure 5:
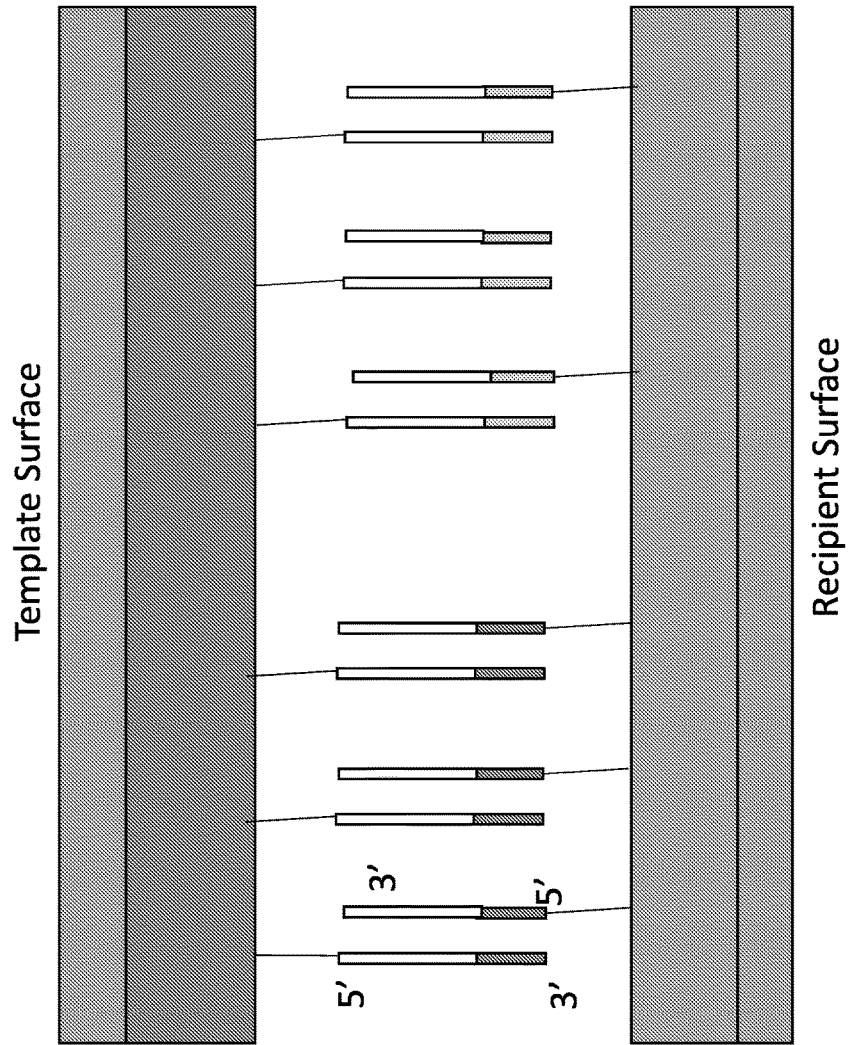
FIG. 5 illustrates a schematic of a second stage of oligonucleotide immobilization transfer (OIT).

The methods herein can also be used to generate oligo arrays with a desired orientation. In some cases, the methods for generating oligo arrays as provided herein on surfaces as provided herein are used to generate oligo arrays that are used as templates (i.e., template arrays) for the generation of one or more oligo arrays comprising oligos coupled thereto that are complementary to oligos on the template array. The oligo arrays comprising oligos coupled thereto that are complementary to a template array can be referred to as a recipient array (or alternatively, transfer array). The transfer or recipient oligo arrays can comprise oligos with a desired orientation. The transfer or recipient arrays can be generated from the template array using an array transfer process. In some cases, template oligo arrays with a desired feature ("spot") density (e.g., feature or spot size of about 1 µm) are subjected to an array transfer process as provided herein in order to generate transfer or recipient oligo arrays with a desired orientation. The desired orientation can be a transfer or recipientoligo array that comprises oligos with the 5' end of each oligo of the array attached to the array substrate. A template oligo array for generating the transfer or recipient oligo array with oligos in a desired orientation (i.e., 5' end of each oligo of the array attached to the array substrate) can have the 3' end of each oligo of the template array attached to the substrate. The array transfer process can be a face-to-face transfer process. In some cases, the face-to-face transfer process occurs by enzymatic transfer or enzymatic transfer by synthesis (ETS). ETS is generally depicted in FIGS. 2A-C and 3. In some cases, the face-to-face transfer process occurs by a non-enzymatic transfer process. The non-enzymatic transfer process can be oligonucleotide immobilization transfer (OIT). OIT is generally depicted in FIGS. 4 and 5.

The face-to-face gel transfer process (e.g., ETS or OIT) can significantly reduce the unit cost of fabrication while simultaneously flipping the oligo orientation (5' immobilized) which can have assay advantages such as allowing for the enzymatic extension of the 3' ends of the array bound oligos. Moreover, ETS or OIT can result in the transfer of a greater number or higher percentage of oligos of a desired or defined length (i.e., full-length oligo) from the template array to the recipient array. Subsequent amplification (e.g., amplification feature regeneration or AFR as provided herein) of the transferred full length product oligos on the recipient oligo arrays can allow the recipient oligo arrays to contain oligos comprising greater than 50 nucleotide bases without suffering from low yield or partial length products.

In some cases, a template and/or recipient array comprises polymers. The polymers can be aptamers or oligos. In some cases, a template or recipient array comprises oligos. A template or recipient array can have coupled to it at least 10, 20, 50, 100, 200, 500, 1,000, 2,000, 5,000, 10,000, 20,000, 50,000 or 100,000, 200,000, 500,000, 1,000,000, 2,000,000, 5,000,000, 10,000,000, 20,000,000, 100,000,000, 200,000,000, 500,000,000, or 1 billion template polymers (e.g., oligos). A template array can have template polymers arranged on it at a density of at least 10, 20, 50, 100, 200, 500, 1,000, 2,000, 5,000, 10,000, 20,000, 50,000 or 100,000 polymers (e.g., oligos) per square millimeter. The polymers (e.g., oligos) on a template or recipient array can be organized into spots, regions, or pixels. Polymers (e.g., oligos) in each spot or region can be identical to each other or related to each other (e.g., all or substantially all include a consensus or common sequence). Polymers (e.g., oligos) in each spot or region can be greater than 55, 60, 65, 70, 75, 80, 85, 90, 95, 99, or 99.9% identical to each other. The template or recipient array can comprise at least 1, 2, 3, 4, 5, 6, 7, 8, 9, 10, 100, 1000, 10,000, 100,000, 1,000,000, or 10,000,000 spots or regions. Each spot or region can have a size of at most about 1 cm, 1 mm, 500 µm, 200 µm, 100 µm, 10 µm, 9 µm, 8 µm, 7 µm, 6 µm, 5 µm, 4 µm, 3 µm, 2 µm, 1 µm, 800 nm, 500 nm, 300 nm, 100 nm, 50 nm, or 10 nm.

A recipient or transfer array generated as provided herein can comprise oligos that are either fully complementary, fully identical, partially complementary, or partially identical in their sequence and/or number to oligos on the template array from which the recipient array was transferred. Partially complementary can refer to recipient arrays that have at least 40%, 45%, 50%, 55%, 60%, 65%, 70%, 75%, 80%, 85%, 90%, 95%, 96%, 97%, 98%, 99%, or 99.9% sequence complementarity. Partially identical can refer to recipient arrays that have at least 40%, 45%, 50%, 55%, 60%, 65%, 70%, 75%, 80%, 85%, 90%, 95%, 96%, 97%, 98%, 99%, or 99.9% sequence identity. A recipient array can have the same number of oligonucleotides as a template array and/or at least 40%, 45%, 50%, 55%, 60%, 65%, 70%, 75%, 80%, 85%, 90%, 95%, 96%, 97%, 98%, 99%, or 99.9% of the number of oligos as the template array from which the recipient array was transferred.

Array fabrication methods as provided herein can result in arrays having polymers (e.g. oligos) of the designed, desired, or intended length, which can be called full-length products. For example, a fabrication method intended to generate oligos with 10 bases can generate full-length oligos with 10 bases coupled to an array. Array fabrication processes can result in polymers (e.g. oligos) of less than the designed, desired, or intended length, which can be called partial-length products. The presence of partial-length oligos can be within a given feature (spot) or between features (spots). For example, a fabrication method intended to generate oligos with 10 bases can generate partial-length oligos with only 8 bases coupled to an array. That is, a synthesized oligo array can comprise many nucleic acids which are homologous or nearly homologous along their length, but which may vary in length from each other. Of these homologous or nearly homologous nucleic acids, those with the longest length can be considered full-length products. Nucleic acids with length shorter than the longest length can be considered partial-length products. Array fabrication methods provided herein can result in some full-length products (e.g., oligos) and some partial-length products (e.g., oligos) coupled to an array in a given feature (spot). Partial-length products coupled to a particular array or within a given feature can vary in length. Complementary nucleic acids generated from full-length products can also be considered full-length products. Complementary nucleic acids generated from partial-length products can also be considered partial-length products.

A transfer method as provided herein (e.g., ETS or OIT) can be used to increase or enrich the amount or percentage of full-length products (e.g., oligo) coupled to a recipient array surface. Array transfer (e.g., ETS or OIT) can result in a transfer or recipient array comprising at least, at most, more than, less than, or about 30%, 40%, 50%, 55%, 60%, 65%, 70%, 75%, 80%, 85%, 90%, 95%, 96%, 97%, 98%, 99%, or 99.9% transferred oligonucleotides that are 100% of the length of the respective oligonucleotide on a template array used to generate the transfer or recipient array. A transferred oligonucleotide that is 100% of the length (i.e., the same or identical length) of a template oligonucleotide can be referred to as full-length product (e.g., full-length product oligo). A template array fabricated by methods known in that art (e.g. spotting or in situ synthesis) can comprise about 20% oligonucleotides that are a desired length (i.e., full-length oligonucleotides) and about 80% oligonucleotides that are not a desired length (i.e., partial-length oligonucleotides). Transfer of the array generated by methods known in the art comprising about 20% full-length oligonucleotides and about 80% partial-length oligonucleotides using array transfer methods as provided herein can result in the generation of transfer or recipient arrays comprising at most about 20% full-length product oligos. In some cases, an array fabricated according to the methods herein has a greater percentage of oligonucleotides of a desired length (i.e., full length oligos) such that transfer of an array fabricated according to the methods herein using array transfer methods provided herein results in the generation of transfer or recipient arrays with a higher percentage of full-length product oligos as compared to fabrication and transfer methods known in the art.

In some cases, a transfer method provided herein (e.g., ETS or OIT) comprises generation of nucleic acid (e.g., oligo) sequences complementary to the template sequences. The transfer can occur by enzymatic replication (e.g., ETS) or by non-enzymatic physical transfer (e.g., OIT) of array components between array surfaces. The array surfaces can be any array surface as provided herein. The substrate of the template array and of the recipient array can be the same or can be different. The transfer can comprise fabrication of complementary sequences which are already attached to a recipient array; for example, primers bound to a recipient array, and are complementary to adaptors on the template array, can be extended using the template array sequences as templates to thereby generate a full length or partial length recipient array. Transfer can comprise fabrication of complementary sequences from a template array followed by attachment of the complementary sequences to a recipient array.

A transfer method as provided herein (e.g., ETS or OIT) can generate a recipient array such that the orientation of a template nucleic acid (e.g., oligo) relative to its coupled recipient array surface is preserved (e.g., the 3' end of the template nucleic acid (e.g., oligo) is bound to the template array and the 3' end of the transferred nucleic acid (e.g., oligo) complement is bound to the recipient array). Transfer can reverse the orientation of a nucleic acid relative to its coupled array surface (e.g., the 3' end of the template nucleic acid is bound to the template array and the 5' end of the transferred nucleic acid complement is bound to the recipient array).

Array transfer can be performed multiple times. Array transfer can be performed multiple times using the same template array. A template array of template polymers bound to a template substrate can be used for the production of at least 1, 2, 3, 4, 5, 6, 7, 8, 9, 10, 20, 30, 40, 50, 60, 70, 80, 90, 100, 500, 1,000, 5,000, 10,000, 50,000, or 100,000 recipient arrays. Array transfer can be performed multiple times in a series of transfers, using the transfer array from one array transfer as the template array for a subsequent transfer. For example, a first transfer can be performed from a template array with oligonucleotides bound to the array at their 3' ends to a first transfer array with complementary oligonucleotides bound to the array at their 5' ends, and a second transfer can be performed from the first transfer array (now serving as a template array) to a second transfer array with a higher percentage of full-length products and sequences matching the original template array than in recipient arrays generated using transfer techniques commonly used in the art while preserving the 5'-surface bound orientation. In some cases, the full-length product oligos on a recipient array generated using the array transfer methods provided herein (e.g., ETS or OIT) are further enriched through amplification of the full-length product oligos on the recipient array. Amplification can be conducted using the methods provided herein. The array transfer method can be a face-to-face enzymatic transfer method (e.g., ETS) or non-enzymatic (e.g., OIT) as provided herein.

In some cases, array transfer by ETS or OIT can be aided by the use of adaptor sequences on the template polymers (e.g., oligos). Polymers (e.g., oligos) can comprise a desired final sequence with the addition of one or more adaptor sequences. For example, a template oligonucleotide can comprise, in order, a 3' end with a first adaptor sequence, a 5' end with a second adaptor sequence, and a desired final sequence in the middle. The first and second adaptor sequences can be the same or can be different. In some cases, oligonucleotides in the same array spot comprise identical first and second adaptor sequences and final sequences, and oligonucleotides in different array spots comprise identical first and second adaptor sequences but different final sequences. Primers on a transfer/recipient array can be complementary to adaptor sequences, allowing hybridization between the primers and the template polymers (e.g., oligos). Such hybridization can aid in the transfer from one array to another.

Figure 6:
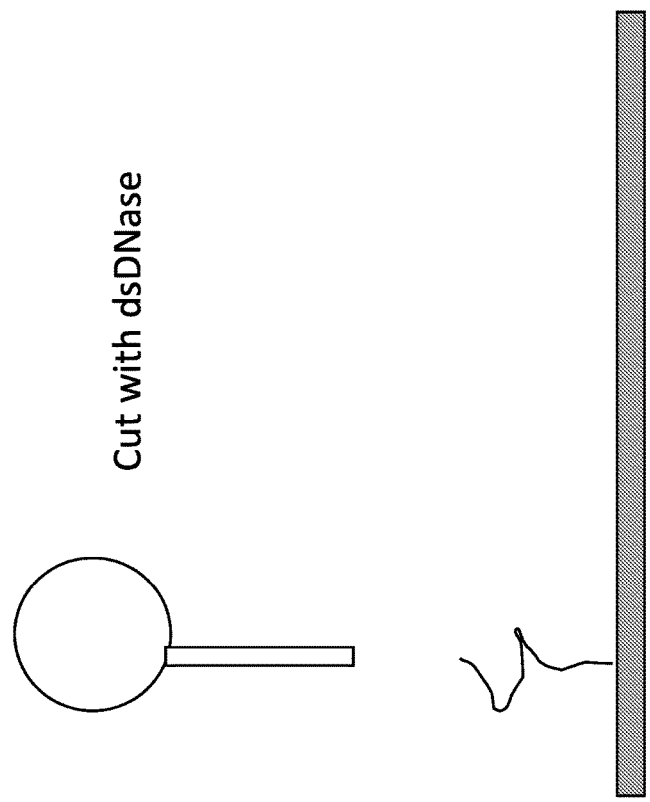
FIG. 6 illustrates a schematic of probe end clipping (PEC) to remove an adapter sequence.
Figure 7:
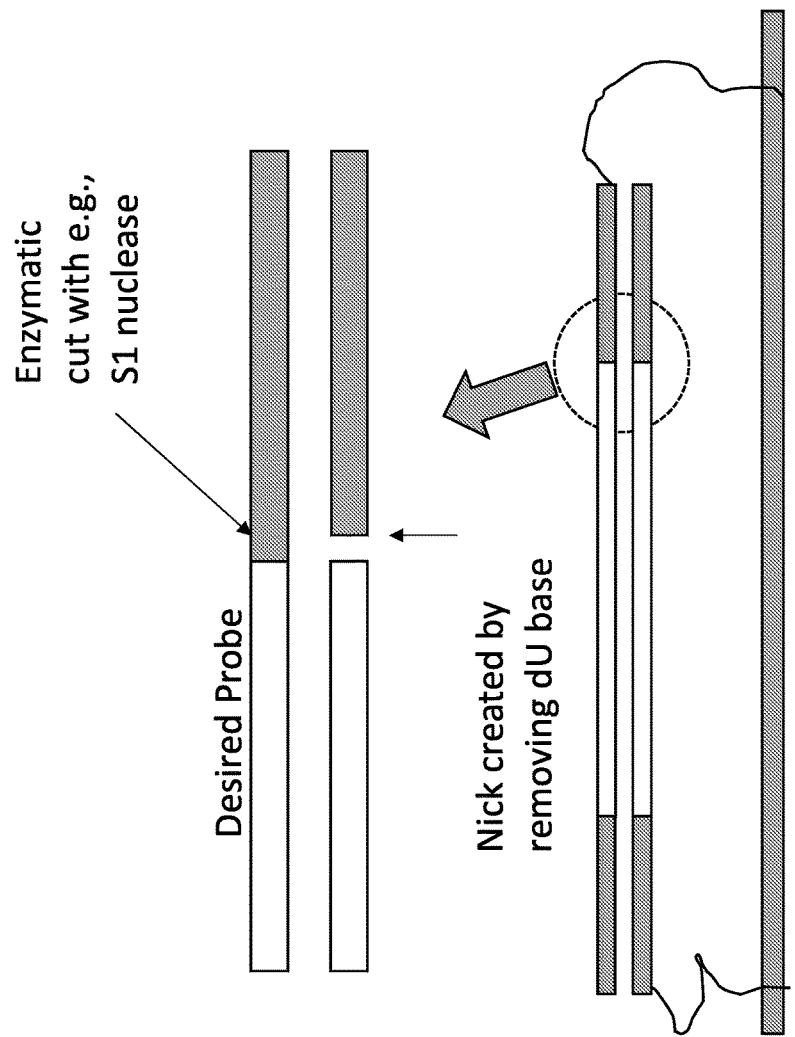
FIG. 7 illustrates a schematic of probe end clipping (PEC) at a nick site.

Some or all adaptor sequences can be removed from transfer/recipient array polymers (e.g. transferred oligonucleotides) after transfer, for example by enzymatic cleavage, digestion, or restriction. Some or all adaptor sequences can be removed from transfer/recipient array polymers (e.g. transferred oligonucleotides) after transfer, for example by enzymatic cleavage, digestion, or restriction. For example, oligonucleotide array components can have adaptors removed via probe end clipping (PEC) by double-strand DNAse. Oligonucleotides complementary to the adaptor sequence can be added and hybridized to the array components. DNAse specific to double-stranded DNA can then be used to digest the oligonucleotides (see FIG. 6). Alternatively, one or more cleavable base, such as a dU, can be incorporated into the primer of the strand to be removed. The primer can then be nicked at the position next to the 3'-most base of the probe, and the nick site can be cut by an appropriate enzyme, such as Mung bean S1 or P1 nuclease (see FIG. 7). Many restriction enzymes and their associated restriction sites can also be used, including but not limited to EcoRI, EcoRII, BamHI, HindIII, TaqI, NotI, HinFI, Sau3AI, PvuII, SmaI, HaeIII, HgaI, AluI, EcoRV, EcoP15I, KpnI, PstI, SacI, SalI, ScaI, SpeI, SphI, StuI, and XbaI. In some cases, the transfer process described above is repeated from the second surface (recipient surface) to a new, third surface containing primers (e.g., oligo) complementary to the top adaptor. Because only the full length oligos can have a complete top adaptor, only these can be copied onto the third array surface (i.e., new or third recipient or transfer array). The process can purify or enrich the full length oligos from the partial products, thus creating a high feature density, high quality full length oligo array. Purification or enrichment can mean the generation of a recipient array such that said recipient array has a greater percentage or number of oligos of a desired length (i.e. full-length) than the array used as a template for the generation of said recipient array. The full-length oligos can be oligos that contain all the desired features (e.g., adaptor(s), barcode(s), target nucleic acid or complement thereof, and/or universal sequence(s), etc.).

In some instances, transfer occurs by an enzymatic transfer or an enzymatic transfer by synthesis (ETS). A transfer array, or a recipient array, surface can comprise surface immobilized oligomers, nucleotides, or primers that are complementary, at least in part, to template nucleic acids or oligonucleotides. In some instances, a transfer array, or recipient array, comprises oligomers that selectively hybridize or bind to aptamers on a template array. Immobilized oligomers, nucleotides, or primers can be complementary to adaptor regions on template polymers.

In some cases, array transfer can be aided by the flexibility or deformability of the array (e.g., template array) or of a surface coating on the array (e.g., template array). For example, an array (e.g., template array) comprising a polyacrylamide gel coating with coupled oligonucleotides can be used in array transfer (e.g., ETS, OIT). The deformability of the gel coating can allow for array components (oligos, reagents (e.g., enzymes)) to contact each other despite surface roughness. Surface roughness can be variability in the topography of the surface.

Array components can be amplified or regenerated by enzymatic reactions termed as amplification feature regeneration (AFR). AFR can be performed on template arrays and/or recipient arrays. AFR can be used to regenerate full-length oligos on an array (e.g., template and/or recipient) in order to ensure that each oligo in a feature (spot) on an array (e.g., template and/or recipient array) comprises desired components (e.g., adaptor(s), barcode(s), target nucleic acid or complement thereof, and/or universal sequence(s), etc.). AFR can be conducted on oligos comprising adaptor and/or primer binding sites (PBS) such that the oligos each comprise a first adaptor (or first PBS), probe sequence, and second adaptor (or second PBS). Preferably, the oligos in each feature on an array (e.g., template and/or recipient array) comprise two or more primer binding sites (or adaptor sequence). AFR can be performed used nucleic amplification techniques known in the art. The amplification techniques can include, but are not limited to, isothermal bridge amplification or PCR. For example, bridge amplification can be conducted on array (e.g., template and/or recipient array) component oligonucleotides via hybridization between adaptor sequences on the array (e.g., template and/or recipient array) components and surface-bound oligonucleotide primers, followed by enzymatic extension or amplification. Amplification can be used to recover lost array (e.g., template and/or recipient array) component density or to increase density of array (e.g., template and/or recipient array) components beyond their original density.

Immobilized oligos, nucleotides, or primers on an array as provided herein (e.g., template and/or recipient array) can be equal in length to each other or can have varying lengths. Immobilized oligos, nucleotides, or primers can comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, or 200 bases. In some cases, immobilized oligos, nucleotides, or primers are 71 bases long (71-mer).

The recipient surface of the transfer array can be brought into close proximity or contact with the template surface of the template array. In some cases, contact between the template array and the transfer array can be aided by the presence of a deformable coating, such as a polymer gel (e.g., polyacrylamide). The deformability of the coating can allow coupled polymers (e.g. oligonucleotides or primers) to come into close enough contact for hybridization to occur. The deformability of the coating can help overcome gaps due to surface roughness (e.g., surface topography variability) or other features that would otherwise prevent close enough contact for hybridization. One or both of the arrays can comprise a substrate with a gel coating with polymer molecules coupled to it. For example, the transfer array can comprise a substrate coupled to a polyacrylamide gel with oligonucleotide primers coupled to the gel. Surfaces and coatings are further discussed elsewhere in this disclosure.

Enzymatic Transfer by Synthesis (ETS)

ETS can comprise a face-to-face polymerase extension reaction as depicted in FIGS. 2A-C and 3 to copy one or more template oligos (e.g., DNA oligo) from a template oligo array onto a second surface (e.g., recipient array). A second surface (e.g., recipient array) with uniform coverage of immobilized primers complimentary to sequence on an oligo in the template oligo array (e.g., the bottom adaptor sequence in oligo arrays comprising adaptor sequence) can be pressed into contact with the template oligo (e.g., DNA oligo) array. A recipient array surface can comprise surface immobilized oligomers (oligos), nucleotides, or primers that are complementary, at least in part, to template nucleic acids or oligos on the template oligo array. In some cases, a transfer or recipient array comprises oligos that selectively hybridize or bind to aptamers on a template array. Immobilized oligos, nucleotides, or primers on a transfer or recipient array can be complementary to adaptor regions on template polymers (e.g. oligos).

Figure 2A:
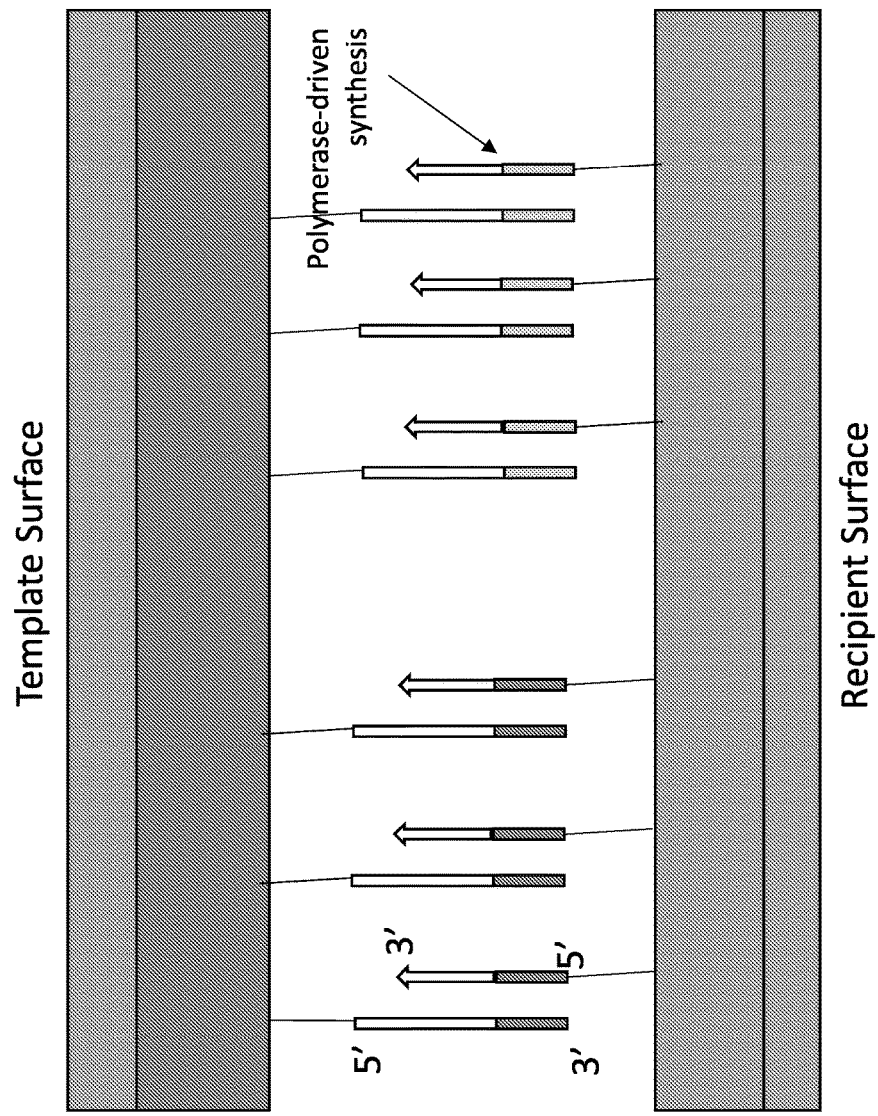
FIG. 2A illustrates a general schematic of enzymatic transfer by synthesis (ETS).
Figure 2B:
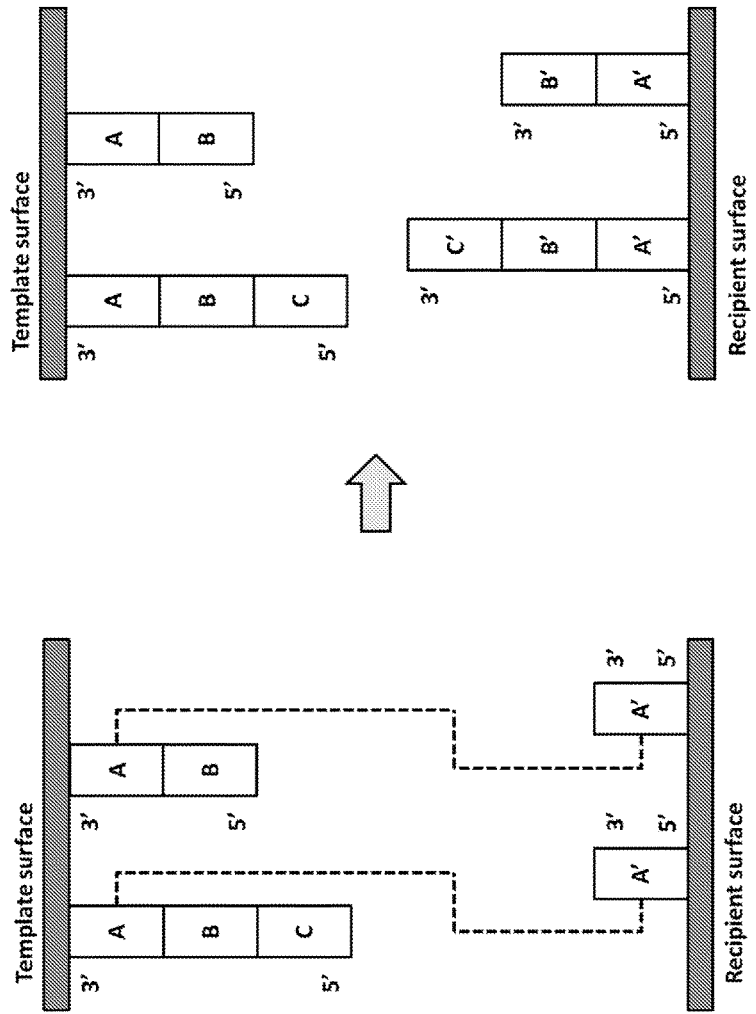
FIG. 2B illustrates a schematic of enzymatic transfer resulting in a different orientation of the nucleic acids relative to the substrate.
Figure 2C:
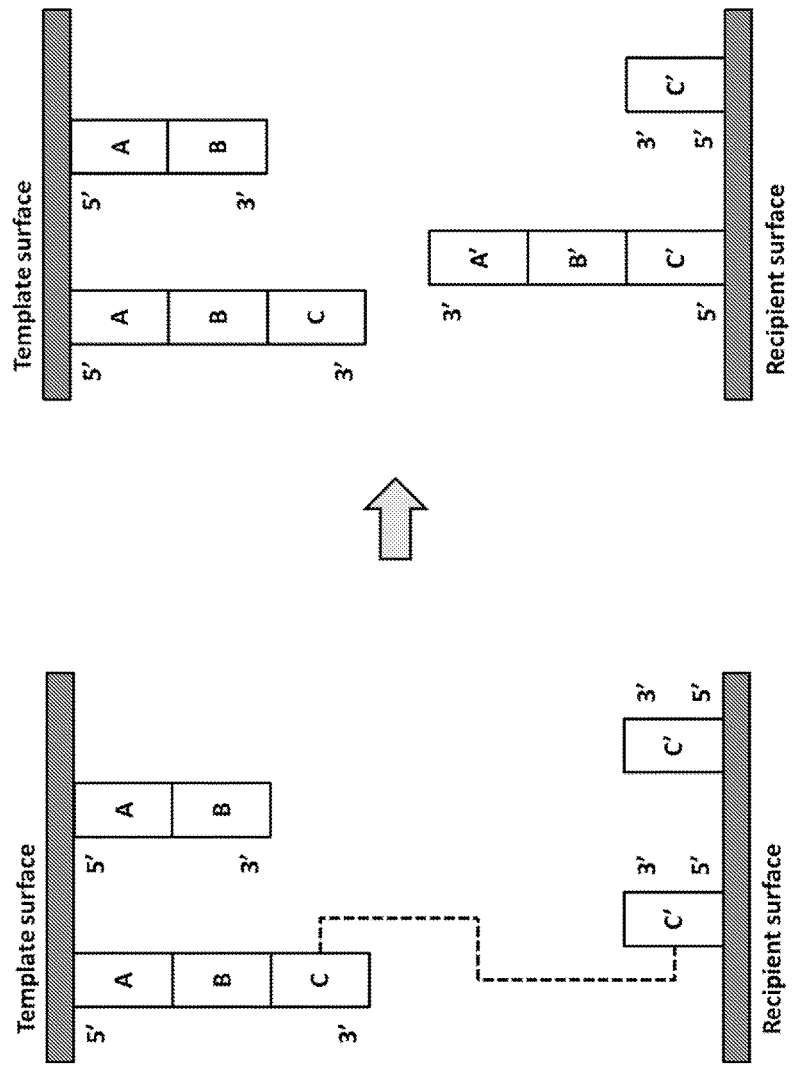
FIG. 2C illustrates a schematic of enzymatic transfer resulting in the transfer of full-length strands.

An Example of an ETS array transfer process as provided herein is illustrated in FIGS. 2A-C. The template nucleic acids (oligos) can hybridize with the immobilized primers or probes on the recipient surface, also called recipient primers or probes or transfer primers or probes. The hybridized complex (e.g., duplex) can be extended enzymatically (see FIG. 2A) such as, e.g., by DNA polymerase including but not limited to PolI, PolII, PolIII, Klenow, T4 DNA Pol, modified T7 DNA Pol, mutated modified T7 DNA Pol, TdT, Bst, Taq, Tth, Pfu, Pow, Vent, Pab, pyrophage.

The transfer process can preserve the orientation of the oligonucleotides, i.e. if the 5' end is bound to the template surface, the 5' end of the synthesized oligonucleotide will be bound to the recipient surface, or vice versa. As shown in FIG. 2A, transfer primers bound at their 5' ends can bind to the template nucleic acids at their 3' ends, followed by enzymatic extension to produce nucleic acids complementary to the template oligos and bound to the recipient array surface at their 5' ends.

Figure 8:
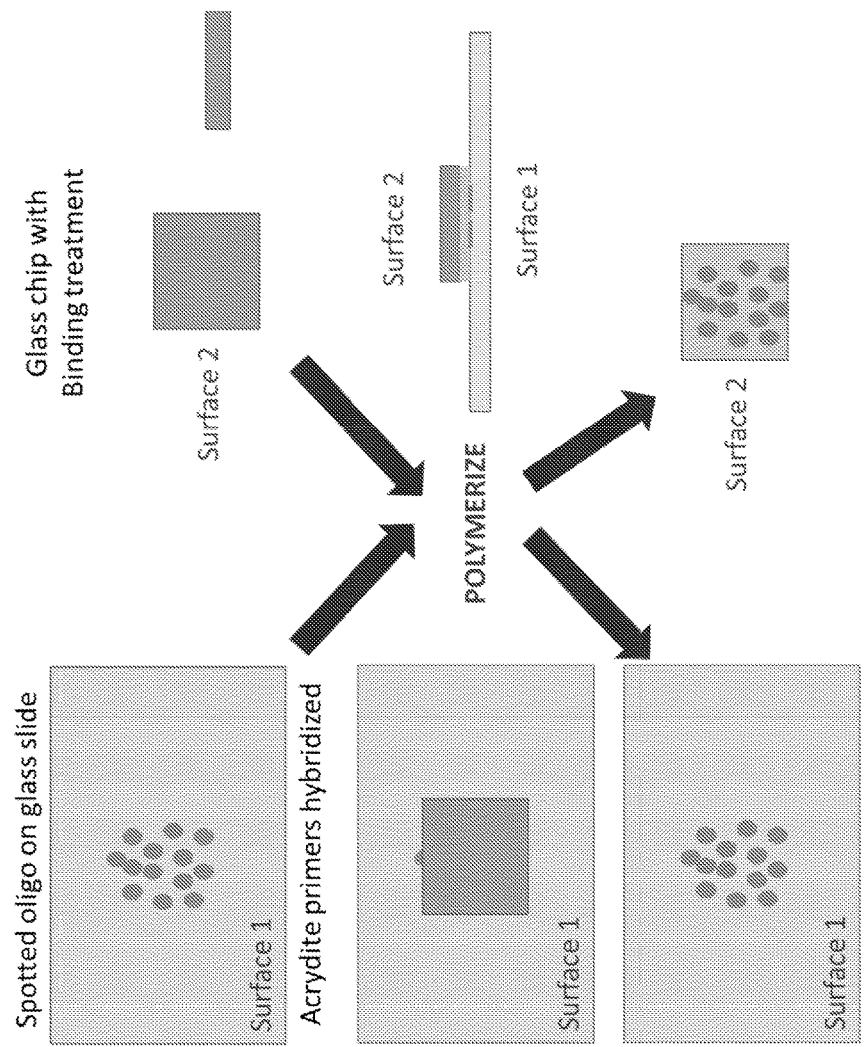
FIG. 8 illustrates a schematic of non-enzymatic gel transfer.

In some cases, only full-length template nucleic acid products are used to generate complements on the recipient array. FIG. 2C shows an example of enzymatic transfer (i.e., ETS) using only full-length template nucleic acid products, which comprise a first adaptor region A, a middle region B, and a second adaptor region C. In FIG. 2C, the recipient array surface comprises primers that are complementary to the second adaptor sequence C at the end of the template nucleic acid. Full-length products on the template array comprise the whole sequence (i.e., first adaptor A-middle region B-second adaptor C) and partial-length products do not (i.e., first adaptor A-middle region B). In FIG. 8C, partial-length products on the template array are not transferred because they lack the second adaptor C and thus cannot be bound by the primer (oligo) on the recipient array that comprises sequence complementary to second adaptor C. In some cases, at least 30%, 40%, 50%, 60%, 70%, 80%, 90%, 95%, 96%, 97%, 98%, 99%, 99.9% or 100% of template nucleic acid oligos on the template array are full-length products (oligos). In some cases, at least 30%, 40%, 50%, 60%, 70%, 80%, 90%, 95%, 96%, 97%, 98%, 99%, 99.9% or 100% of transfer or recipient nucleic acid products (oligos) generated on the recipient array are full-length products. The generation of partial-length products on the recipient array during ETS can be due to incomplete extension of full-length template oligos during polymerase-driven synthesis. The generation of full-length products on the recipient arrays can be accomplished using AFR as provided herein.

In some cases, the recipient array includes on it primers that hybridize a portion of the template polymers (e.g., oligos) such that extension reactions occur until all of the template polymers (e.g., oligos) are used as templates for synthesis of a complementary recipient oligos on a complementary array (or recipient array). In some instances, synthesis of the recipient array occurs such that on average at least 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, or 50% of the template polymers (e.g., oligos) are used to generate complementary sequences on the recipient array. Stated differently, a recipient array, post-transfer, can comprise recipient nucleotides (e.g., oligos) synthesized using at least 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, or 50% of the template oligonucleotides as templates.

Figure 3:
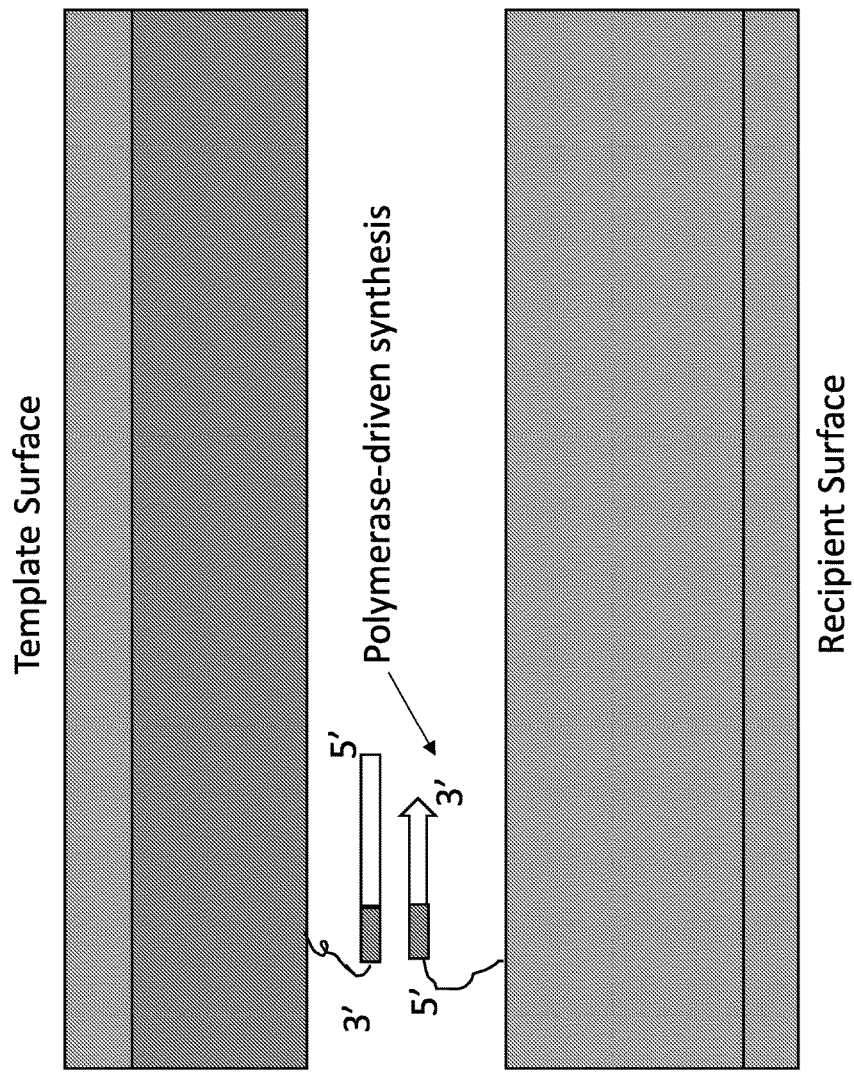
FIG. 3 illustrates a schematic of synthesis on the recipient surface from the template surface.

The array transfer process (e.g., ETS) can invert the orientation of the template nucleic acids (see FIG. 2B, FIG. 3). That is, if the 5' end is bound to the template surface, the 3' end of the synthesized oligonucleotide will be bound to the recipient surface, or vice versa. For example, FIG. 2B shows an enzymatic transfer (i.e., ETS) of template nucleic acids (e.g., oligos) on the surface of a template array which can comprise some or all of a first adaptor region A, a middle region B, and a second adaptor region C. In FIG. 2B recipient surface primers (A') that are complementary to an adaptor sequence located at the substrate end of the template nucleic acids and is designated A are used to conduct enzymatic transfer. In this case, both partial-length and full-length complementary products (oligos) are transferred, and their orientation relative to the substrate surface of the template array is reversed.

As shown in FIG. 3, template nucleic acids (e.g., oligos) bound to the template array surface (template surface) at their 3' ends can hybridize to transfer primers on the recipient array bound to the recipient array surface at their 5' ends. Enzymatic extension of the transfer primers produces nucleic acids (e.g., oligos) complementary to the template nucleic acids (e.g., oligos) and bound to the recipient array surface at their 5' ends. The same process can be conducted for template nucleic acids bound to the template surface at their 5' ends when transfer primers are bound to the recipient array surface at their 3' ends. Extension of these transfer primers results in nucleic acids (e.g., oligos) complementary to the template nucleic acids (e.g., oligos) and bound to the recipient array surface at their 3' ends. In some cases, partial-length oligos in a feature (spot) of the template array) are utilized to generate complementary partial length oligos on a recipient array. In some cases, full-length oligos in a feature (spot) of the template array are utilized to generate complementary full-length oligos on a recipient array.

The template and recipient surfaces can be biocompatible, such as polyacrylamide gels, modified polyacrylamide gels, PDMS, or any other biocompatible surfaces (e.g., silica, silicon, COC, and metals such as gold or chrome). If the surface comprises a polymer gel layer, the thickness can affect its deformability or flexibility. The deformability or flexibility of a gel layer can make it useful in maintaining contact between surfaces despite surface roughness. Details of the surfaces are further discussed herein.

Reagents and other compounds including enzymes, buffers, and nucleotides can be placed on the surface or embedded in a compatible gel layer. The enzymes can be polymerases, nucleases, phosphatases, kinases, helicases, ligases, recombinases, transcriptases, or reverse transcriptases. In some cases, the enzymes on the surface or embedded in a compatible gel layer comprise a polymerase. Polymerases can include, but are not limited to, PolI, PolII, PolIII, Klenow, T4 DNA Pol, modified T7 DNA Pol, mutated modified T7 DNA Pol, TdT, Bst, Taq, Tth, Pfu, Pow, Vent, Pab, Phusion, pyrophage, and others. Details of the surfaces are further discussed herein. In some cases, the enzymes on the surface or embedded in a compatible gel layer comprise a ligase. Ligases can include, but are not limited to, *E. coli* ligase, T4 ligase, mammalian ligases (e.g., DNA ligase I, DNA ligase II, DNA ligase III, DNA ligase IV), thermostable ligases, and fast ligases.

Figure 12:
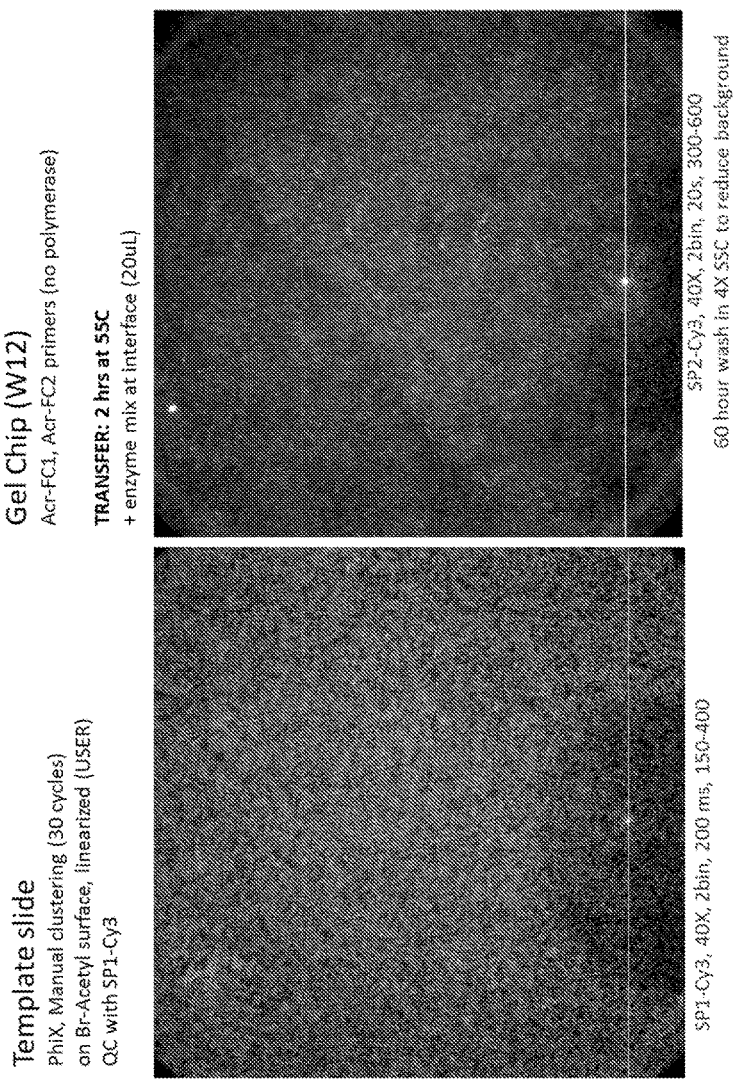
FIG. 12 illustrates template slide (left) and gel chip (right) with clusters transferred via enzymatic extension.
Figure 13:
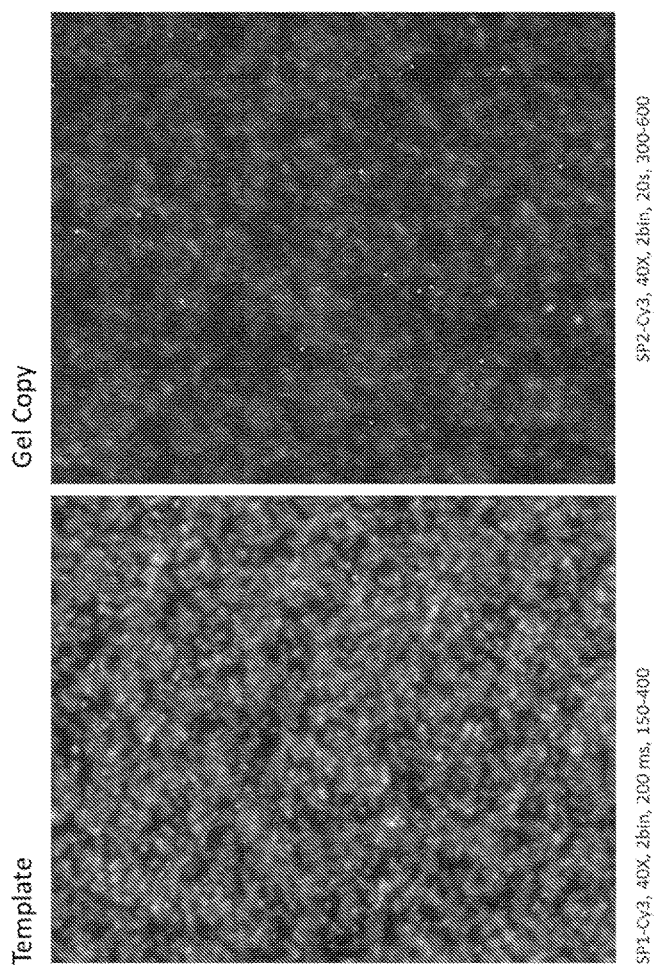
FIG. 13 illustrates zoomed in image of the template (left) and gel copy (right) from FIG. 12.
Figure 14:
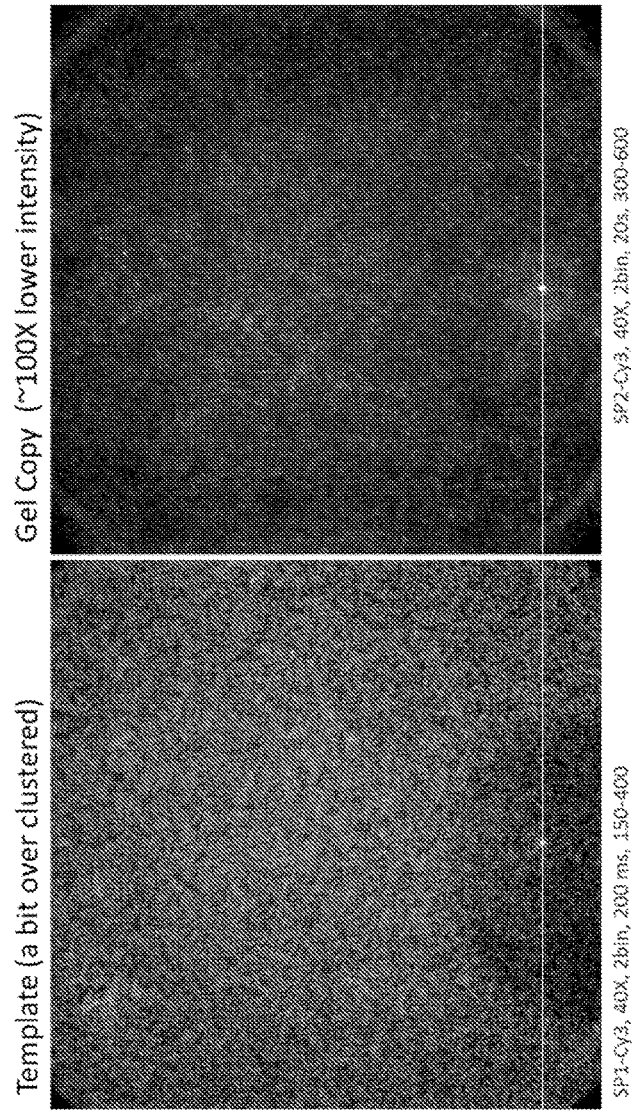
FIG. 14 illustrates a comparison in intensity of a template (left) and gel copy (right), the latter having ~100× lower intensity than the former.
Figure 15:
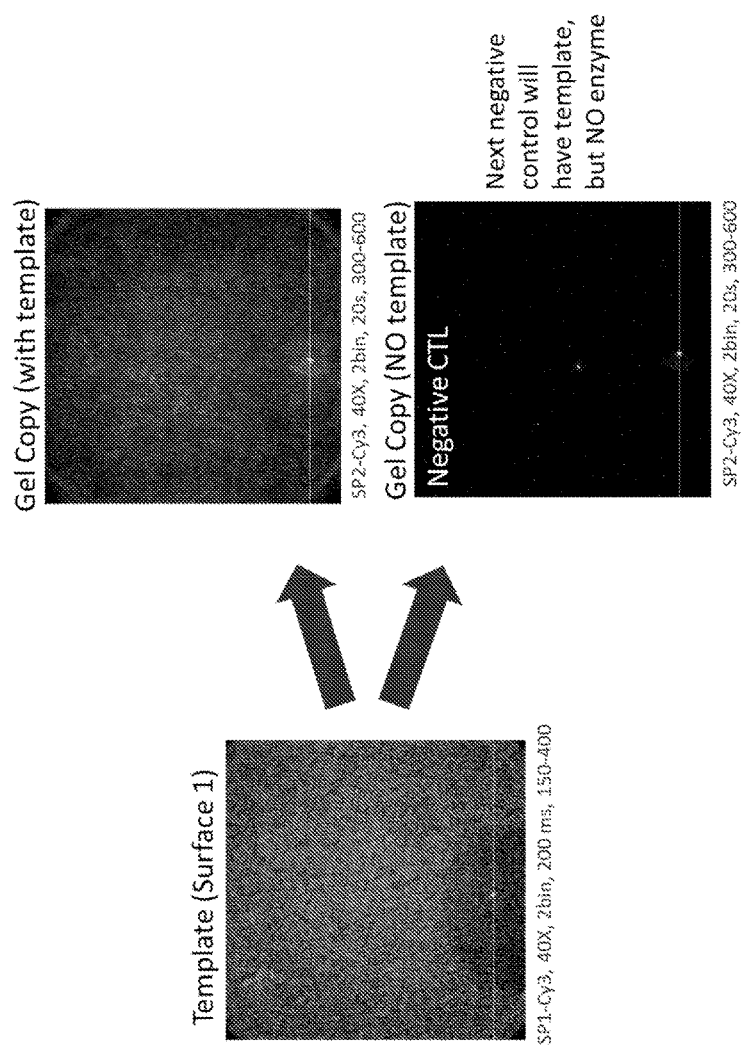
FIG. 15 illustrates enzymatic transfer to a gel copy compared to a negative control surface with no template present.
Figure 22:
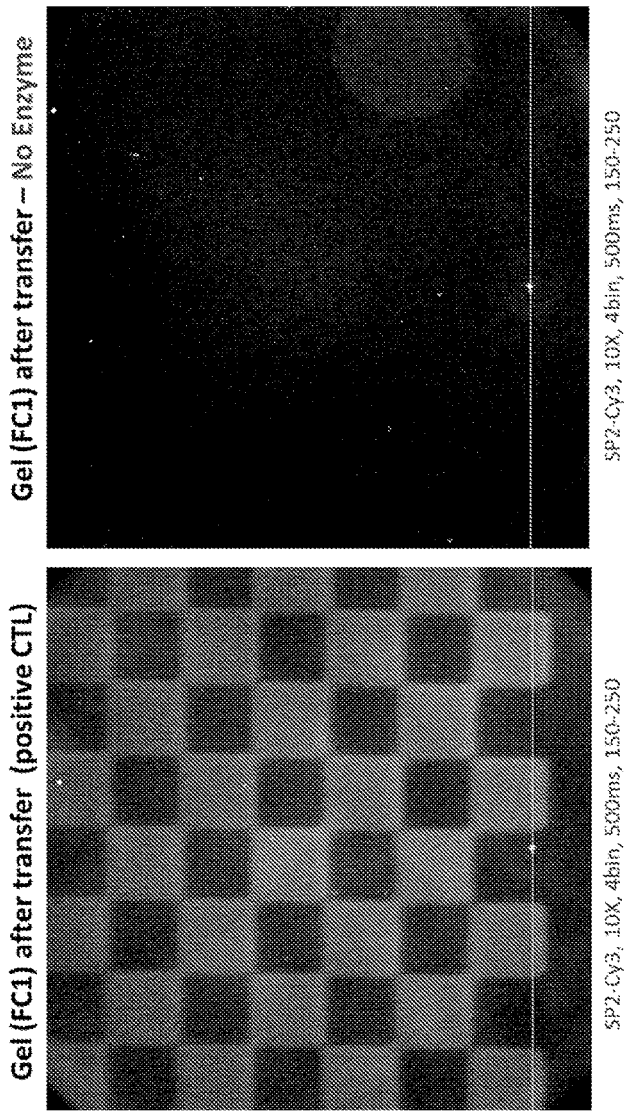
FIG. 22 illustrates enzymatic transfer to a gel copy (left) compared to a negative control surface with no enzyme present (right).

A template surface and a post-transfer recipient surface generated by enzymatic extension are shown in FIGS. 12, 13, and 14. The surface of the recipient array can be a gel formed on top of the template array. FIG. 15 shows an example of an enzymatic extension reaction as described herein from a template array surface to a recipient surface (i.e., Gel Copy (with template)) in the presence of a reaction mixture (e.g., primers, enzymes, buffers as outlined herein) and template as well as a negative control where a template array is subjected to an enzymatic extension reaction as described herein to a recipient surface (Gel Copy (NO template)) in the presence of a reaction mixture (e.g., primers, enzymes, buffers as outlined herein) but no template nucleic acids. The lack of fluorescence in the negative control (i.e., Gel Copy (NO template)) demonstrates a lack of product generated in the absence of template nucleic acids. FIG. 22 shows results from an additional control experiment, wherein a template array surface (left) was contacted with a recipient transfer surface in the presence of a reaction mixture (i.e., primers, buffers) (right) but in the absence of enzyme. The lack of fluorescence on the recipient array (right) in FIG. 22 demonstrates a lack of transfer. The reaction mixture can be placed on the surface of the recipient array or embedded in a recipient surface. In some cases, the reaction mixture is placed on the surface of the recipient array. In some cases, the reaction mixture is embedded in the recipient surface. The recipient surface can be a compatible gel layer. The reaction mixture can comprise any reagent necessary to conduct enzymatic transfer by synthesis (ETS). The reagents can comprise Enzymatic transfer of a template array by ETS can be conducted as follows: 1.) enzyme mix is prepared (e.g., 37 µL H$_2$O, 5 µL 10× Thermopol buffer, 5 µl of 10 mg/mL BSA, 1 µl of 10 mM dNTPs, and 2 µl of 8 U/µL Bst enzyme); 2.) enzyme mix is applied to a recipient array (e.g., an acrylamide gel coated glass slide with coupled oligonucleotide primers prepared as described elsewhere in this disclosure); 3.) a template array is placed face-to-face with the and allowed to react (e.g., clamped together in a humidity chamber for 2 hours at 55° C.); 4.) the template and recipient arrays are separated (e.g., loosened by application of 4×SSC buffer and pulled apart with the aid of a razor blade); 5.) the template array is rinsed (e.g., in DI water) and dried (e.g., with N$_2$); and 6.) the recipient array is rinsed (e.g., with 4×SSC buffer and 2×SSC buffer). In some cases, the oligos on the template array comprise adaptors, such that a bottom adaptor is located proximal to the template array surface, while a top adaptor is located distal from the template array surface. While the sandwich is heated to 55° C., Bst polymerase in Thermopol PCR buffer can extend the primers from the recipient array hybridized to the bottom adaptor of the template array, which can create a dsDNA molecular bridge between the template and recipient array surfaces. Upon physical separation, the second surface (i.e., recipient array) can contain the complementary ssDNA barcode array with the 5' end of the oligos attached to the surface and the 3' end available for polymerase extension. Since both the uniformly dispersed primer on the template array and the barcode oligos on the recipient array can be tethered to their respective surfaces, the relative locations of the transferred features can be maintained (in mirror image). To achieve intimate contact and thus uniform transfer over the full chip area, a broad range of surface materials (PDMS, Polyacrylamide), thicknesses, and process conditions can be used.

Oligonucleotide Immobilization Transfer (OIT)

In some instances, the generation of a recipient array is performed by non-enzymatic transfer. One form of non-enzymatic transfer is oligonucleotide immobilization transfer (OIT). In OIT, the template nucleic acids (e.g., oligo) on a template array can be single-stranded. Primers comprising sequence complementary to a portion of the template oligos can hybridize to the template oligos and be extended by primer extension in order to generate and can be made double-stranded template oligos on the template array. The primers used for primer extension can be in solution. Many polymerases can be used for OIT, including PolI, PolII, PolIII, Klenow, T4 DNA Pol, modified T7 DNA Pol, mutated modified T7 DNA Pol, TdT, Bst, Taq, Tth, Pfu, Pow, Vent, Pab, Phusion and others. In some cases, the primers used for primer extension comprise linkers that are used to immobilize or bind strand of the double-stranded template oligo generated by primer extension (see FIG. 4) on a surface of a recipient array. The recipient arrray surface can be a planar surface, a bead, or a gel as provided herein. In some cases, the recipient array surface is a polyacrylamide gel formed during OIT (as shown in FIG. 5). In some cases, subsequent to extension, the linkers can be bound to a recipient array surface. The recipient array surface can be any array surface as provided herein such as a polymer gel or modified glass surface. In OIT, the template and recipient array surfaces can be then be separated. The DNA (i.e., double-stranded template oligos) can be melted prior to separation.

Figure 9:
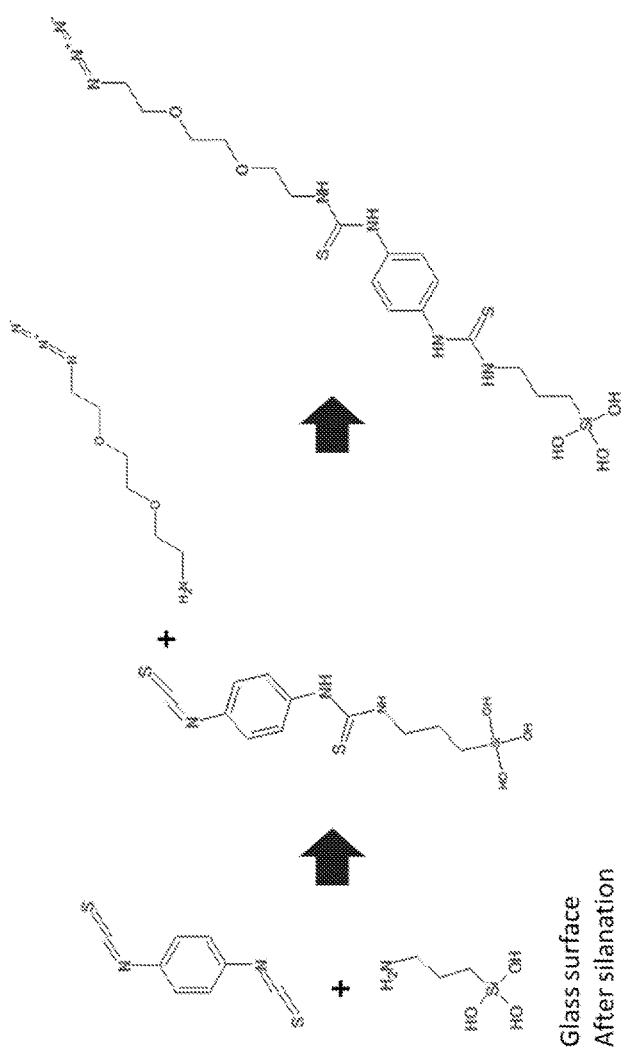
FIG. 9 illustrates a schematic of a schematic of the first stage of the attachment of oligonucleotides to a glass surface after silanation using the cross-linker 1,4-Phenylene Diisothiocyanate (PDITC).
Figure 10:
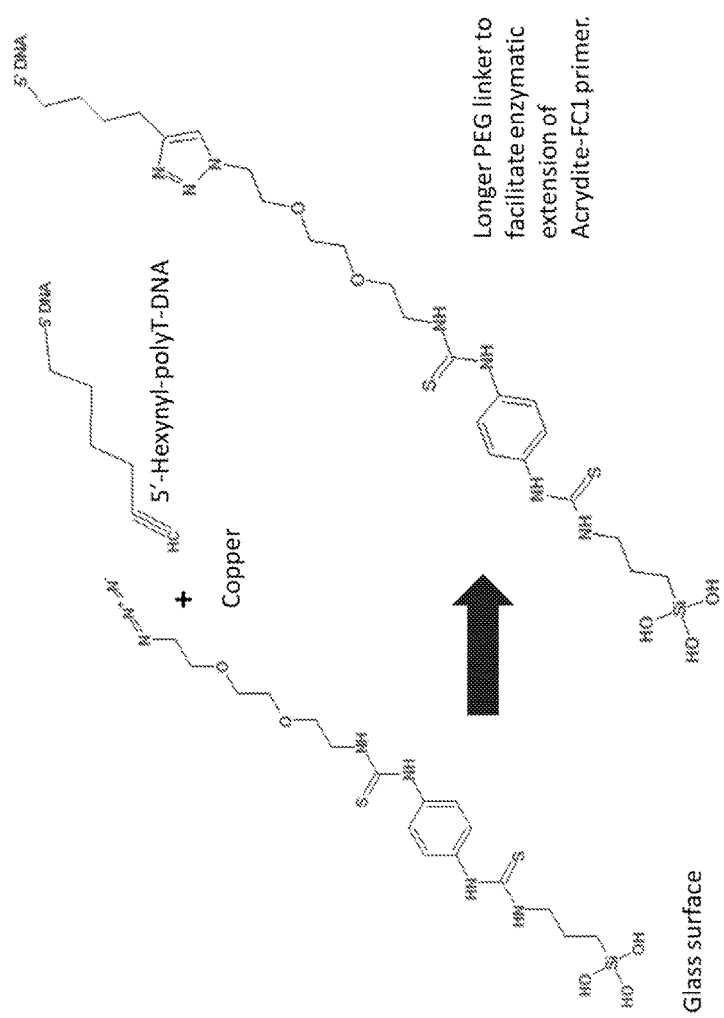
FIG. 10 illustrates a schematic of the second stage of the attachment of oligonucleotides to a glass surface after silanation using PDITC.
Figure 11:
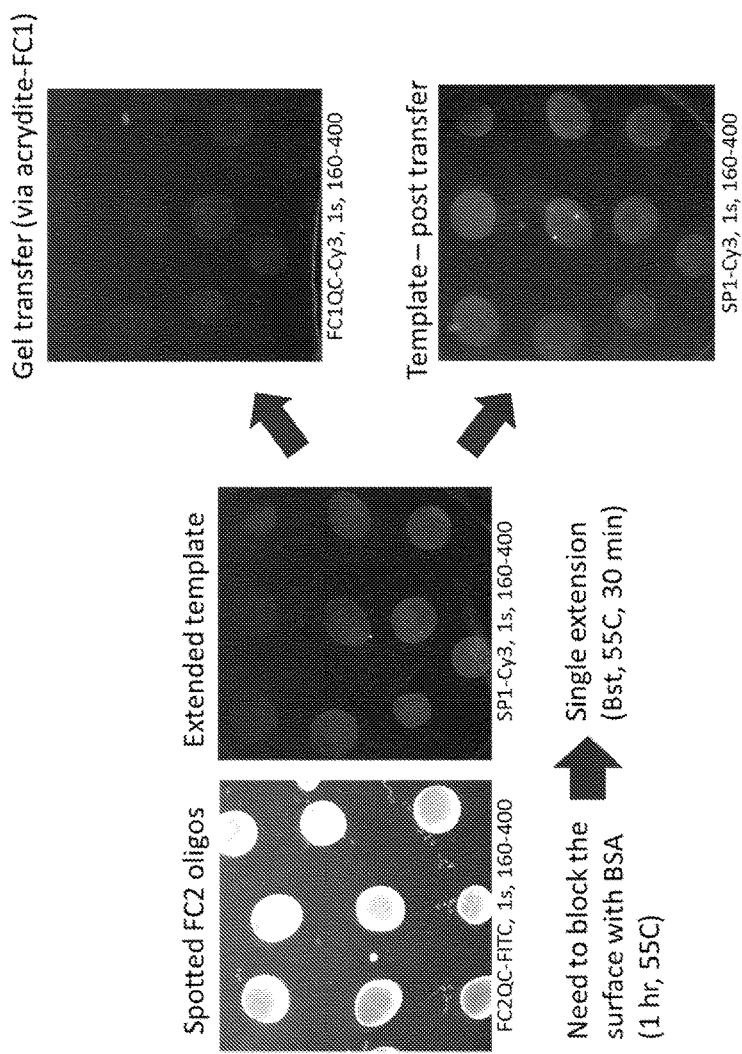
FIG. 11 illustrates gel transfer of oligonucleotides attached to a silanated glass surface using PDITC as illustrated in FIGS. 9-10.

In some cases, the primers used in OIT are 5'-acrydite modified primers. The 5'-acrydite modified primers can be capable of incorporation into a polymer gel (e.g., polyacrylamide) during polymerization as provided herein. Extension products from the template nucleic acids (e.g., oligos) can then be generated with the acrydite primers, contacted with a substrate with a binding treatment (e.g., unpolymerized polyacrylamide coating precursor), incorporated during polymerization, and separated (see FIG. 8 for an illustration). The primers can be 5'-hexynyl-polyT-DNA. In some cases, primer extension products from the template nucleic acids are generated via binding and extension of complementary 5'-hexynyl-polyT-DNA primers. Following extension, the 5'hexynyl-polyT-DNA primers can be: 1.) contacted with a substrate with a binding treatment (such as glass treated with silane), 2.) linked to a cross-linker such as, for example, a homobifunctional linker such as 1,4-Phenylene Diisothiocyanate (PDITC), 3.) linked to an N3 bonding group with a PEG linker, (e.g., FIG. 9), 4.) bonded to the substrate at the N3 group (e.g., FIG. 10), and 5.) separated during a second stage of OIT (FIG. 11). Examples of PDITC-N3 attachment of nucleic acids are shown in FIGS. 9 and 10. The surfaces can be any of the surfaces as discussed herein. Other cross-linkers that can be used in place of PDITC can include dimethyl suberimidate (DMS), disuccimidyl carbonate (DSC) and/or disuccimidyl oxylate (DSO). This process can preserve the orientation of the oligonucleotides, i.e. if the 5' end is bound to the template array surface, the 5' end of the synthesized oligonucleotide will be bound to the recipient array surface, or vice versa. While enzymatic extension can be used prior to the transfer, the transfer itself can be conducted without enzymatic reactions.

Figure 16:
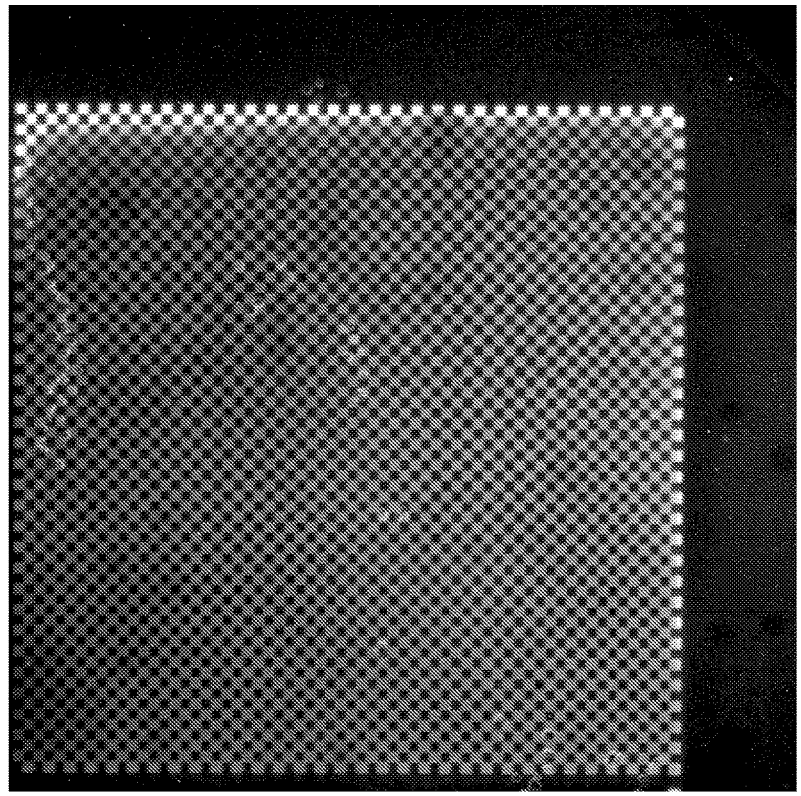
FIG. 16 illustrates a template array comprising fluorescently labeled oligos attached to the surface in a checkerboard pattern.
Figure 17:
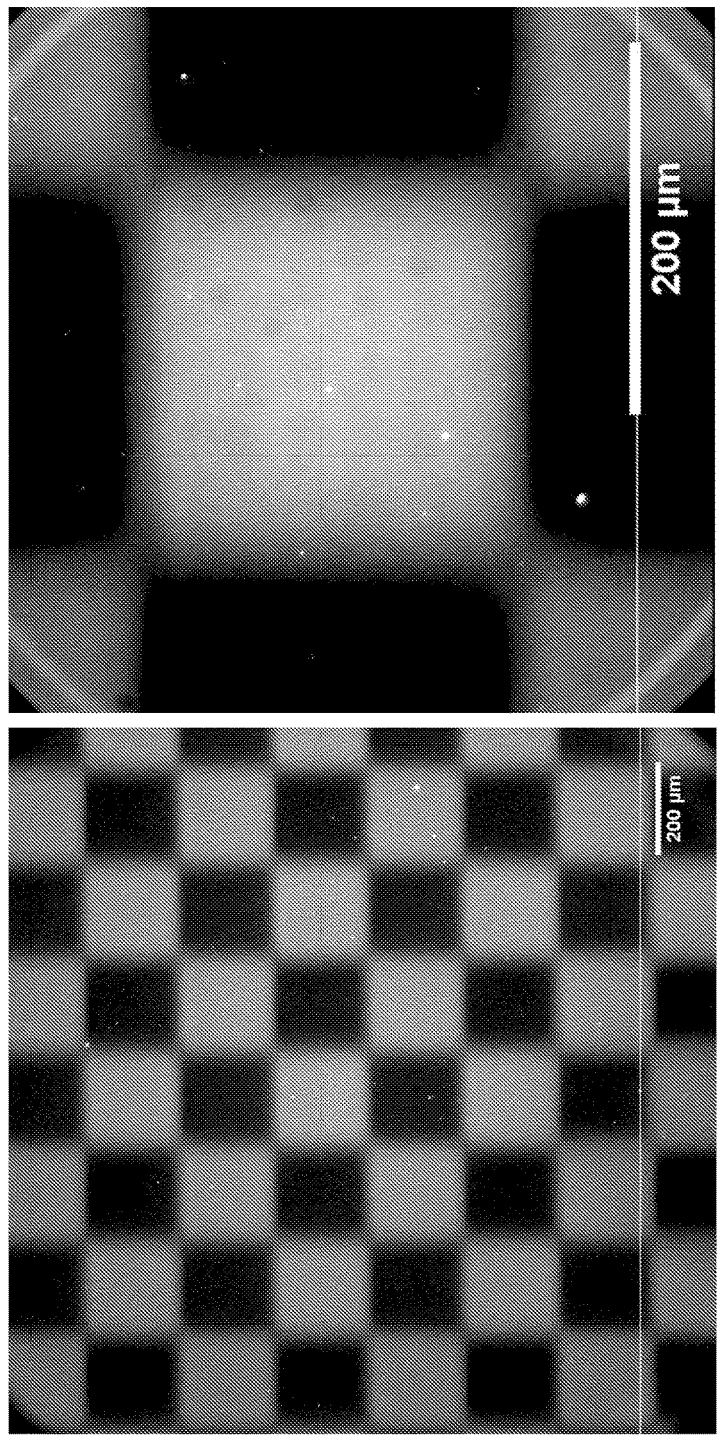
FIG. 17 illustrates zoomed in views of the surface in FIG. 16.
Figure 18:
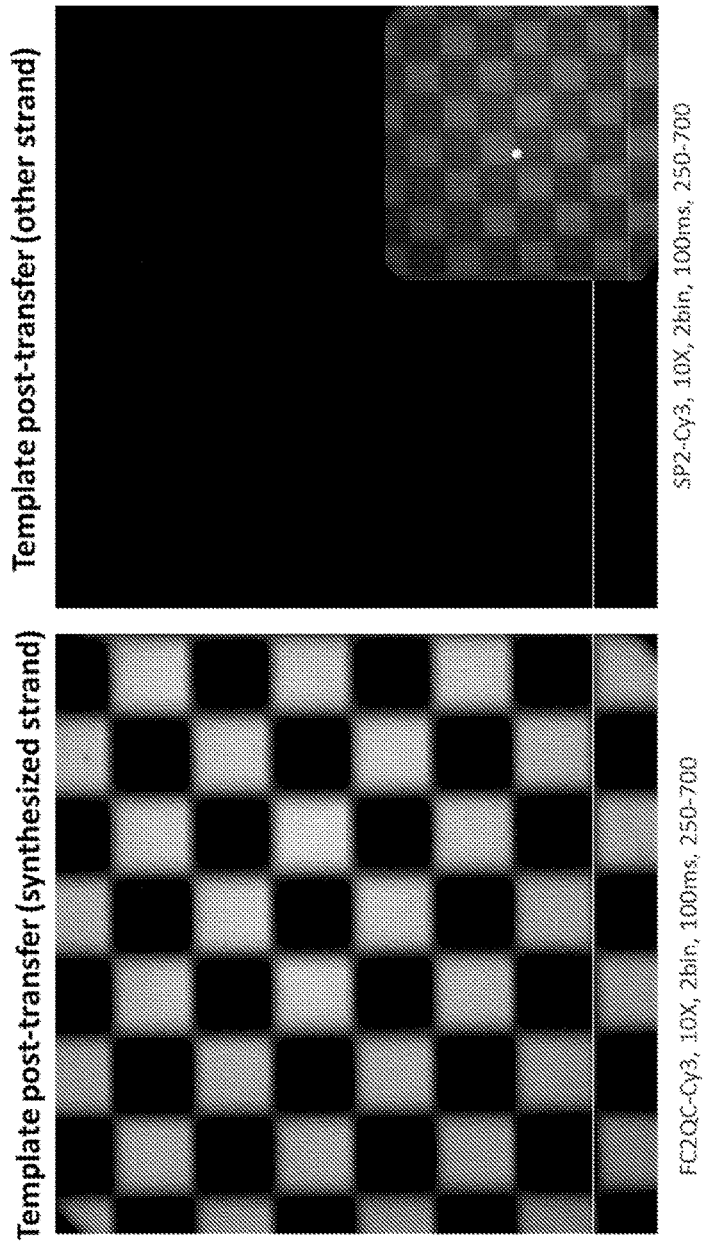
FIG. 18 illustrates a template after non-enzymatic gel transfer, with signal from the synthesized strand (left) and the other strand (right).
Figure 19:
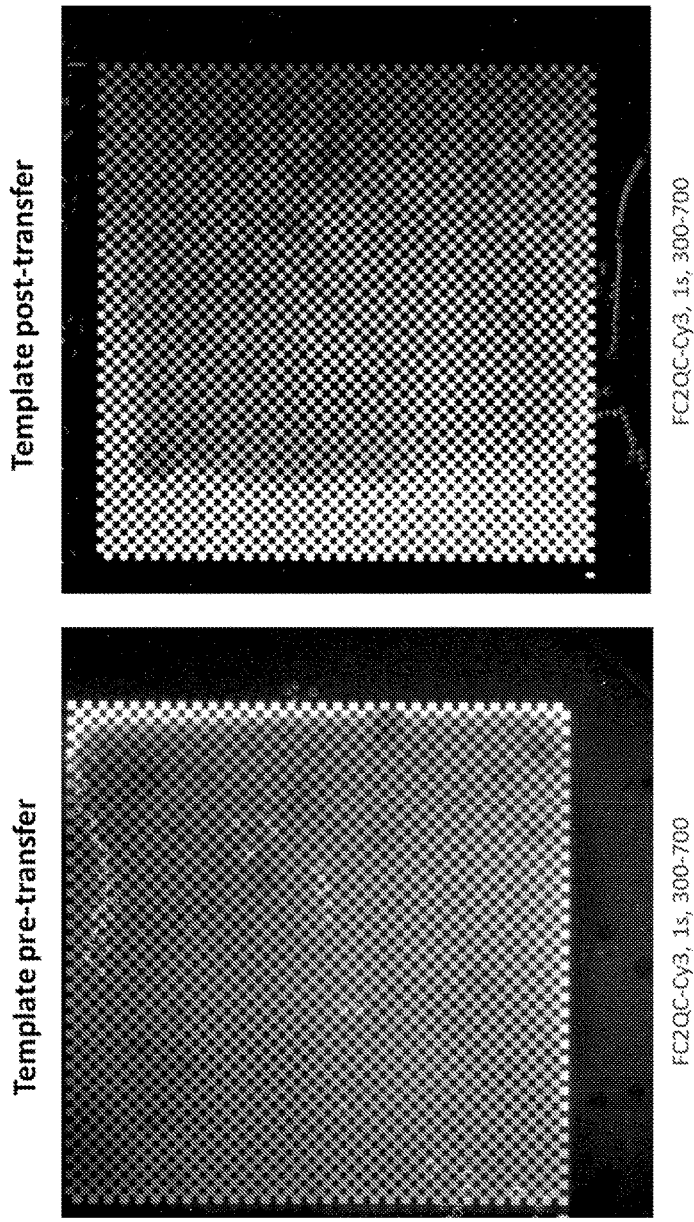
FIG. 19 illustrates a template pre- (left) and post- (right) non-enzymatic gel transfer.
Figure 20:
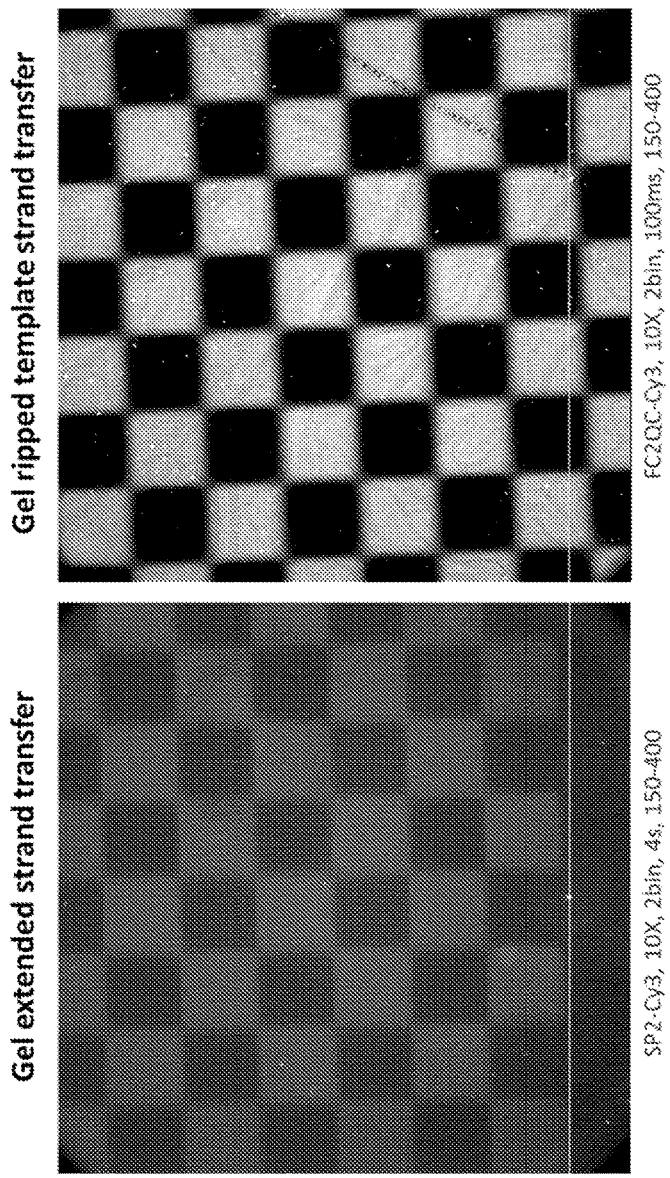
FIG. 20 illustrates copies from gel extended strand transfer (left) and gel ripped template strand transfer (right).

FIG. 16 shows a picture of a fluorescently labeled template array, with template molecules having the structure 5' CAGAAGACGGCATACGAGAT_GACTGGAGTTCA-GACGTGTGCTCTTCC_GTGTAGATCTCGGTG-GTCGCCGTA-3'T*-(HEG)$_2$-(substrate surface) Prior to imaging, the array was allowed to hybridize with 500 nM of QC FC2-Cy3 in 4×SSC buffer at 55° C. for 60 minutes. FIG. 17 shows zoomed in views of regions of the same template array. FIG. 18 shows the same template array as well as a recipient transfer array after a non-enzymatic transfer. The template nucleic acids were hybridized with Acr-FC1 primers and extended with Bst polymerase, then incorporated into a polymer gel on a recipient transfer array substrate and separated from the template array. The template array shows no appreciable decrease in signal post-transfer, while the transfer array shows a small signal under 10× exposure. FIG. 19 shows a side-by-side comparison of a template array pre- and post-transfer. As can be seen, the template array shows no appreciable decrease in signal post-transfer. FIG. 20 shows a comparison between non-enzymatic transfer with gel extension strand transfer and non-enzymatic transfer with gel ripped template strand transfer FIG. 21 shows a comparison in exposure settings between gel images, one with 10× 2 S 2 bin and one with 10× 0.5 s 10 bin.

In some cases, an oligo array with 5' to 3' orientation can be generated without enzymatic transfer. For example, the unbound end of the synthesized nucleic acid sequences on a template oligo array can comprise a linker sequence complementary to a sequence at or near the array-bound end of the oligo, allowing the oligo to circularize. The oligo can further comprise a restriction sequence at the same end. Digestion of the restriction sequence on circularized oligos serve to flip the full-length oligos containing the linker sequence and cut loose any partial-length oligo products on the array which lack the linker sequence. Many restriction enzymes and their associated restriction sites can be used, including but not limited to EcoRI, EcoRII, BamHI, HindIII, TaqI, NotI, HinFI, Sau3 AI, PvuII, SmaI, HaeIII, HgaI, AluI, EcoRV, EcoP15I, KpnI, PstI, SacI, SalI, ScaI, SpeI, SphI, StuI, and XbaI.

VII. Surfaces

The surfaces used for the transfer methods as provided herein (e.g., template surface and/or the recipient surface) can comprise a range of possible materials. In some cases, the surface comprises a polymer gel or coating on a substrate, such as a polyacrylamide gel or a PDMS gel. In some cases, the surface comprises a gel without a substrate support. In some cases, the surface comprises a thin coating on a substrate, such as sub-200 nm coatings of polymer. In some cases, the surface comprises an uncoated substrate, such as glass or silicon. The polymer coatings can form polymer brush thin-films. The polymer coatings can include some cross-linking. The polymer coatings can form a graft structure. The polymer coatings can form a network structure. The polymer coatings can form a branched structure. The polymers can comprise homogenous polymers. The polymers can comprise block copolymers. The polymers can comprise gradient copolymers. The polymers can comprise periodic copolymers. The polymers can comprise statistical copolymers.

The polymer coating can have a range of thicknesses or widths. The polymer coating can have a thickness or width of about 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The polymer coating can have a thickness or width of less than 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The polymer coating can have a thickness or width of more than 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The polymer coating can have a thickness or width of at least 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The polymer coating can have a thickness or width of at most 0.0001, 0.00025, 0.0005, 0.001, 0.005, 0.01, 0.025, 0.05, 0.1, 0.2, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, or 200 mm. The polymer coating can have a thickness or width of between 0.0001 and 200 mm, between 0.01 and 20 mm, between 0.1 and 2 mm, or between 1 and 10 mm. The polymer coating can have a thickness or width of from about 0.0001 to about 200 mm, about 0.01 to about 20 mm, about 0.1 to about 2 mm, or about 1 to about 10 mm. In some cases, the polymer coating comprises a width or thickness of about 10 microns. The polymer coating can be at least 1 μm, 2 μm, 3 μm, 4 μm, 5 μm, 7 μm, 8 μm, 9 μm, 10 μm, 15 μm, 20 μm, 25 μm, 30 μm, 40 μm thick. The polymer coating may be at least 50 μm thick. The polymer coating may be at least 75 µm thick. The polymer coating may be at least 100 µm thick. The polymer coating may be at least 150 µm thick. The polymer coating may be at least 200 µm thick. The polymer coating may be at least 300 µm thick. The polymer coating may be at least 400 µm thick. The polymer coating may be at least 500 µm thick. The polymer coating may be between about 1 µm and about 10 µm thick. The polymer coating may be between about 5 µm and about 15 µm thick. The polymer coating may be between about 10 µm and about 20 µm thick. The polymer coating may be between about 30 µm and about 50 µm thick. The polymer coating may be between about 10 µm and about 50 µm thick. The polymer coating may be between about 10 µm and about 100 µm thick. The polymer coating may be between about 50 µm and about 100 µm thick. The polymer coating may be between about 50 µm and about 200 µm thick. The polymer coating may be between about 100 µm and about 30 µm thick. The polymer coating may be between about 100 µm and about 500 µm thick.

Gels and coatings can additionally comprise components to modify their physicochemical properties, for example, hydrophobicity. For example, a polyacrylamide gel or coating can comprise modified acrylamide monomers in its polymer structure such as ethoxylated acrylamide monomers, phosphorylcholine acrylamide monomers, and/or betaine acrylamide monomers. The coating can be hydrophobic or hydrophilic. The coating can comprise a polymer coating or polymer brush, such as polyacrylamide or modified polyacrylamide. The coating can comprise a gel, such as a polyacrylamide gel or modified polyacrylamide gel. The coating can comprise metal, such as patterned electrodes or circuitry. The coating or functionalization can comprise a binding agent, such as streptavidin, avidin, antibodies, antibody fragments, or aptamers. The coating or functionalization can comprise multiple elements, for example a polymer or gel coating and a binding agent.

Gels and coatings can additionally comprise markers or reactive sites to allow incorporation of markers. Markers can comprise oligonucleotides. For example, 5'-acrydite-modified oligonucleotides can be added during the polymerization process of a polyacrylamide gel or coating. Reactive sites for incorporation of markers can comprise bromoacetyl sites, azides, sites compatible with azide-alkyne Huisgen cycloaddition, or other reactive sites. Markers can be incorporated into the polymer coatings in a controlled manner, with particular markers located at particular regions of the polymer coatings. Markers can be incorporated into the polymer coatings at random, whereby particular markers can be randomly distributed throughout the polymer coatings.

In some cases, physiochemical properties of the polymer coatings herein are modified. The modification can be achieved by incorporating modified acrylamide monomers during the polymerization process. In some cases, ethoxylated acrylamide monomers are incorporated during the polymerization process. The ethoxylated acrylamide monomers can comprise monomers of the form $CH_2=CH-CO-NH(-CH_2-CH2-O-)_nH$. The ethoxylated acrylamide monomers can comprise hydroxyethyl acrylamide monomers. The ethoxylated acrylamide monomers can comprise ethylene glycol acrylamide monomers. The ethoxylated acrylamide monomers can comprise hydroxyethylmethacrylate (HEMA). The incorporation of ethoxylated acrylamide monomers can result in a more hydrophobic polyacrylamide surface coating. In some cases, phosphorylcholine acrylamide monomers are incorporated during the polymerization process. The phosphorylcholine acrylamide monomers can comprise other phosphorylcholine acrylamide monomers. In some cases, betaine acrylamide monomers are incorporated during the polymerization process. The betaine acrylamide monomers can comprise other betaine acrylamide monomers.

In some cases, a surface with a gel coating can be prepared as follows: glass slides are cleaned (e.g., with NanoStrip solution), rinsed (e.g. with DI water), and dried (e.g. with $N_2$); the glass slide surface is functionalized with acrylamide monomers; a silanation solution is prepared (e.g., 5% by volume (3-acrylamidopropyl)trimethoxysilane in ethanol and water); the glass slide is submerged in the silanation solution (e.g. for 5 hours at room temperature), rinsed (e.g., with DI water), and dried (e.g. with $N_2$); a 12% acrylamide gel mix is prepared (e.g., 5 mL $H_2O$, 1 mg gelatin, 600 mg acrylamide, 32 mg bis-acrylamide); a 6% acrylamide gel mix is prepared (e.g., 50 µL 12% acrylamide gel mix, 45 µL DI water, 5 µL 5'-acrydite modified oligonucleotide primers (1 mM) vortexed to mix); 6% acrylamide gel mix is activated (e.g., 1.3 µL of 5% ammonium persulfate and 1.3 µL of 5% TEMED are each added per 100 µL of gel mix and vortexed); gel mix is applied to a surface (e.g. silanized functionalized glass slide surface), evenly spread (e.g. by pressing with a cover slip or by spin coating), and allowed to polymerize (e.g., 20 minutes at room temperature).

VIII. Array Amplification and Regeneration

Figure 24:
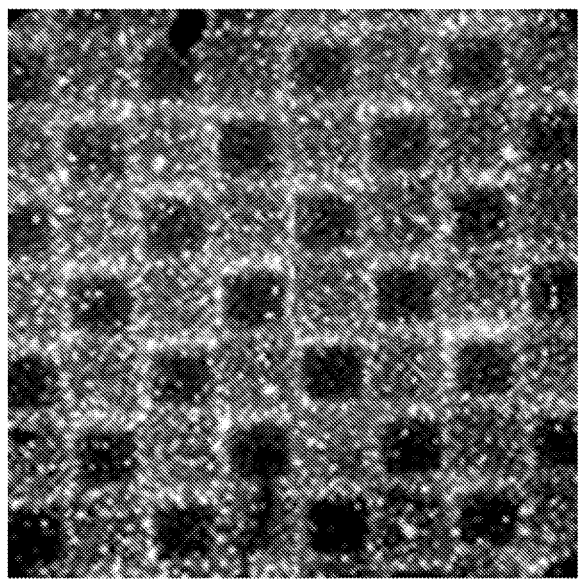
FIG. 24 illustrates cluster amplification after enzymatic transfer.

The number of array components (e.g., nucleic acids, oligomers) in each array section can be amplified or regenerated. Amplification can be desirable for the template array if the array components on the template array have become depleted, for example from loss during transfers. Amplification can be desirable for the transfer array if the number of array components on the transfer array is low, for example due to a transfer from a template array with low density or a low number of array components. For example, FIG. 24 shows a template array used in enzymatic transfer and subsequently amplified with 50-70 cycles of amplification.

Amplification can be aided by the use of adaptor sequences on the template polymers. Polymers can comprise a desired final sequence in addition to one or more adaptor sequences. For example, a template oligonucleotide can comprise, in order, a 3' end with a first adaptor sequence, a 5' end with a second adaptor sequence, and a desired final sequence in the middle. The first and second adaptor sequences can be the same or can be different. In some cases, oligonucleotides in the same array spot comprise identical first and second adaptor sequences and final sequences, and oligonucleotides in different array spots comprise identical first and second adaptor sequences but different final sequences. Primers on a transfer array can be complementary to adaptor sequences, which can allow hybridization between the primers and the template polymers. Such hybridization can aid in amplification or regeneration of the array. Primers coupled to an array can be generic e.g., universal or random primers, or target-specific primers.

Amplification of array components can occur enzymatically (e.g., bridge amplification or RPA). For example, if the array components comprise oligonucleotides, amplification can occur by nucleic acid amplification reactions such as polymerase chain reaction (PCR), bridge amplification, bridge PCR, isothermal PCR, isothermal bridge amplification, isothermal bridge PCR, continuous flow PCR, recombinase polymerization amplification (RPA), or other reactions. The enzymes used can comprise a variety of enzymes, such as PolI, PolII, PolIII, Klenow, T4 DNA Pol, modified T7 DNA Pol, mutated modified T7 DNA Pol, TdT, Bst, Taq, Tth, Pfu, Pow, Vent, Pab or other polymerase enzymes; helicase; recombinase; or other enzymes.

The intensity or density of coupled polymers (e.g., nucleic acids) on an array can be recovered by amplification. The intensity or density of coupled polymers (e.g., nucleic acids) on an array can be increased beyond its initial value by amplification. Array spots can grow during amplification. For example, bridge amplification or bridge PCR can lead to growth or walking of nucleic acid molecules by 50-100 nm during 28 cycles of amplification.

Array surfaces can comprise barriers to prevent amplification of array components beyond their individual feature borders. Barriers can comprise physical borders, reaction borders, or other borders. Borders can be fabricated by laser ablation of surface-coupled features (e.g. nucleic acids or other polymers). Borders can be fabricated by light-activated protective groups; for example, light-activated protective groups can be coupled to nucleic acids across an entire array, and then only desired areas can be deprotected.

IX. Applications and Advantages

Figure 23:
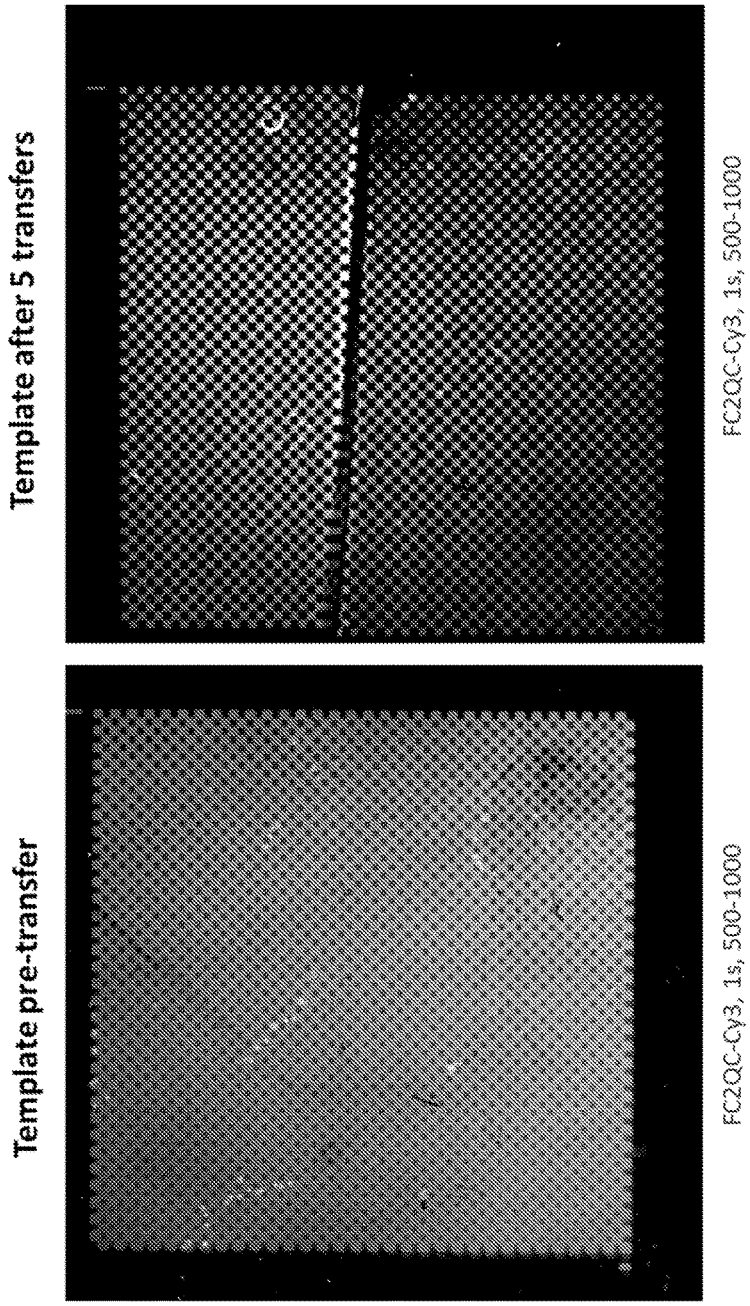
FIG. 23 illustrates a template array before (left) and after (right) 5 enzymatic transfers using the face-to-face enzymatic gel transfer process (e.g., enzymatic transfer by synthesis or ETS) described herein.

The compositions and methods described in this disclosure can be used for a range of applications. For example, a template array can be generated by standard means, and a plurality of recipient transfer arrays can be generated as complement or recipient arrays from the template. This can result in reduced fabrication costs. In some instances, at least 5, 10, 20, 50, 100, 200, 500, 1,000, 2,000, 5,000, 10,000, 20,000, 100,000, 200,000, 500,000 complement arrays or recipient arrays can be generated from each template array. For example, FIG. 23 shows images of a template array pre-transfer (left) and after five transfers (right). Each of the complement arrays can result in oligonucleotide probes that are complementary to at least 50, 60, 70, 80, 90, 91, 92, 93, 94, 95, 96, 97, 98, 99, or 99.5% of the template molecules on the template array.

Recipient transfer arrays can comprise more enzymatically-favorable environments than arrays fabricated by standard means, thus allowing a wider range of reactions to be conducted on or near the array surface. For example, a recipient transfer array can comprise a polymer gel or coating, such as polyacrylamide, which is more favorable to enzyme activity than an uncoated surface such as glass or silicon.

Recipient transfer arrays can be fabricated comprising oligonucleotides with 3' ends up. This can provide reduced steric hindrance for hybridization. This can also provide oligonucleotides in a configuration useful for further extension, including sequencing by synthesis or genotyping (e.g. SNP detection).

Recipient transfer arrays can be generated with very long oligonucleotides. While synthesis of very long oligonucleotides can result in very few full-length oligonucleotide products, the compositions and methods described in this disclosure can generate recipient transfer arrays comprising mostly or only full-length oligonucleotides.

In some cases, the compositions and methods described in this disclosure can provide arrays with fine resolution, defined (i.e. not random) sequences in 5' to 3' orientation, and on an enzymatically compatible surface.

For enzymatic transfer methods, the immobilization of the oligonucleotides can reduce cross-contamination between array features. Furthermore, for a single-strand template the need to make a complementary strand before transfer can be eliminated.

EXAMPLES

Example 1—Enzymatic Transfer of Template Via Single Extension Silanation of Gel-Chip Surfaces Glass slides were cleaned overnight in NanoStrip solution, rinsed with deionized (DI) water, and dried with $N_2$. The surface was then functionalized with acrylamide monomers which will bind a polyacrylamide gel to the surface. A silanation solution was prepared with 475 mL ethanol, 25 mL deionized water, and 26 mL (3-acrylamidopropyl)trimethoxysilane, for a 5% v/v final concentration of silane. A rack of cleaned and dried glass slides were submerged in the silanation solution and agitated gently at room temperature for 5 hours. Slides were subsequently placed in a fresh ethanol bath, repeated five times. Slides were then rinsed in a deionized water bath and dried with $N_2$. Slides were stored in a desiccated chamber until further use.

Preparation of Acrylamide Gel Mix

A 12% acrylamide gel mix was prepared with 5.00 mL of $H_2O$, 1.00 mg gelatin, 600.00 mg acrylamide, and 32.00 mg bis-acrylamide. The components were dissolved and mixed together for a final concentration of 12% acrylamide gel mix. For a 6% gel chip, 50 μL of 12% acrylamide gel mix, 45 μL of deionized water, and μL of 5'-acrydite-FC1 (1 mM concentration) functionalized oligonucleotides were combined for a total volume of 50 μL and vortexed.

Polymerization of Thin Gels

To the mix for a 6% gel chip prepared above, 1.3 μL of 5% ammonium persulfate per 100 μL reaction mix and 1.3 μL of 5% TEMED per 100 μL reaction mix were added as activators, for a final activator concentration of 0.065% each. The mixture was then vortexed. 15 μL of the gel mix was pipetted onto a clean flat surface, for example a glass slide or a silicon wafer. The gel mix on the surface was covered with a gel-chip glass slide surface as prepared in above, face down. The glass chip was pressed down to achieve a more uniform spread of the gel mix. The gel was allowed to polymerize at room temperature for 20 minutes. The gel was bound to the chips and the gel-chip substrates were removed from the clean flat surface, with the aid of a razor blade or other implement if necessary. Gel chips were rinsed in deionized water and excess gel from the chip edges was removed. Gel chips can be used immediately or stored in 4× saline-sodium citrate (SSC) buffer.

Preparation of Enzyme Mix

Enzyme mix was prepared with 37 μL of $H_2O$, 5 μL of 10× Thermopol buffer, 5 μL of BSA (10 mg/mL), 1 μL of dNTPs (10 mM), and 2 μL Bst DNA polymerase enzyme (8 U/μL).

Enzymatic Transfer of Template Via Single Extension

18 μL of enzyme mix as prepared above was placed on top of the prepared gel chip. The enzyme mix solution was allowed to permeate into the gel for 30 seconds. The gel chip was then placed face down onto a template chip. A piece of PDMS was placed on top of the two chips as a compliant layer, and the chip stack was placed into a clamp, such as an aluminum clamp. The chip stack was incubated at 55° C. for 2 hours in a humidity chamber. Then, extra 4× saline-sodium citrate (SSC) buffer was added around the edges of the chip stack and allowed to soak in to loosen the gel chip. The gel chip surface and template chip surface were then pulled apart, with the aid of a razor blade or other implement if necessary. The gel remained bound to the gel chip, with transferred oligonucleotides. The template chip was washed in deionized water and dried with $N_2$. The gel chip was washed three times with 4×SSC buffer and three times with 2×SSC buffer.

Imaging of the Transferred Pattern

FC2QC-Cy3 oligonucleotides were hybridized for 35 minutes at 55° C. to a template chip as used in above. After hybridization, the template chip was rinsed and imaged. SP2-Cy3 oligonucleotides were hybridized for 30 minutes at 55° C. to a gel chip with transferred oligonucleotides as prepared in above. The gel chip was then rinsed twice with 4×SSC buffer and twice with 2×SSC buffer, and let to soak in 4×SSC buffer for 3 hours to reduce background signal. Rather than soaking for 3 hours, the gel chip could alternatively have been shaken for 20 minutes in 4×SSC buffer. The gel chip was then imaged under an epi-fluorescence microscope at desired magnifications, such as 10× and 40×. The gel chip was then stripped and hybridized with FC2QC-Cy3 oligonucleotides as for the template chip. The gel chip was then reimaged, and signal indicating physical transfer of template molecules was observed.

Preparation of Reaction Buffer for Template Amplification by Ingredient Volume

Reaction buffer was prepared with 1.5 mL of 10× Taq buffer, 750 µL of 100% DMSO, 3 mL of 5 M Betaine, 120 µL of 25 mM dNTPs, 75 µL of 5000 U/mL Taq polymerase, and 9.555 mL nuclease-free H$_2$O.

Preparation of Reaction Buffer for Template Amplification by Final Concentration Reaction buffer was prepared with a final concentration of 1× Taq buffer, 5% DMSO, 1 M Betaine, 0.2 mM dNTPs, 25 U/mL Taq polymerase, in nuclease-free H$_2$O.

Template Amplification Via Thermal Cycling

A gel chip with oligonucleotides was washed with 0.3× SSC buffer with 0.1% Tween-20 added. The gel chip then underwent 50 cycles of immersion into solution baths as follows: a) 45 seconds in 0.3×SSC buffer with 0.1% Tween-20 at 94° C., b) 2 minutes in 5×SSC buffer with 0.1% Tween-20 at 60° C., and c) 1 minute in reaction buffer, prepared as per above, at 72° C. The template on the gel chip was amplified.

Probe Hybridization on a Chip

A chip to be imaged with double stranded DNA (dsDNA) was placed in 0.1 N NaOH solution for 3 minutes to denature the DNA. After washing, the chip was washed with 4×SSC buffer. The chip was then incubated for 40 minutes at 55° C. with 20 mL of 100 nM fluorescently-labeled hybridizing probe solution on a nutator. After the incubation, the chip was washed twice with 4×SSC buffer and twice with 2×SSC buffer for 20 minutes per wash step. The chip was then imaged.

Example 2—From Photo-Directed 3'-5' Array to 5'-3' Full Length Array

Via standard photo-directed synthesis, a template microarray is fabricated with 3'-5' oligonucleotide features, with the oligonucleotides containing an adaptor 1 sequence, a probe sequence that varies between features, and an adaptor 2 sequence. The oligonucleotides are hybridized with a primer complementary to adaptor 1 which also contains an immobilizable linker. Primer extension reactions are conducted with polymerase. A first recipient array surface is brought into contact with the template array and the linkers are bound to its surface. The two surfaces are separated, and the recipient array contains both partial length and full length products in 5'-3' orientation. The oligonucleotides are hybridized with a primer complementary to adaptor 2 which also contains an immobilizable linker. Primer extension reactions are conducted with polymerase. A second recipient array surface is brought into contact with the template array and the linkers are bound to its surface. The two surfaces are separated, and the second recipient array contains mostly full length products in 5'-3' orientation.

Example 3—Array Transfer Protocol (Bio3D)

Polyacrylamide Gel Casting (2$^{nd}$ Surface)
Preparation and Filtration of the Following Solutions:
a. 6% acrylamide gel mix with 50 µM Acryd-FC2 (2$^{nd}$ surface)

TABLE 1

| Acrylamide Mix | |
| --- | --- |
| | Bulk solution (6% gel mix with 50 µM Acryd-FC2) |
| Milli-Q H$_2$O | 160 µL |
| 1 mM Acrydite-FC2 | 10 µL |
| 40% Acrylamide & Bis-acrylamide (29:1) | 30 µL |
| Total | 200 µL | b. 2.6% ammonium persulfate (APS, w/v): 13 mg of APS into 500 µL Milli-Q water.
c. 2.6% TEMED (v/v): 7.8 µL of TEMED into 292.2 µL of Milli-Q water.

Activation of Acrylamide Gel (Final Concentration 0.13%), and Cast onto Acryl-Silanized Solid Surfaces Such as Glass and Fused Silica.
a. Take out a pre-diced 1×1 inches silanzied fused-silica, blow the surface with nitrogen gas.
b. Take a fresh 1.5 mL Eppendorf tube, add the solutions in the following order: 9 µL of 6% gel mix, 0.5 µL of 2.6% APS, and 0.5 µL of 2.6% TEMED. Vortex thoroughly and quick spin the solution to the bottom.
c. Add 9 µL of activated gel mix solution onto the silanized glass surface in one drop, immediately take out a new coverslip (circle, 18 mm diameter), blow the surfaces of coverslip with nitrogen gas, and carefully lay down the coverslip on top of the gel mix. The gel mix will spread and fill the whole area between coverslip and silanized glass surface.
d. After 30 minutes of acrylamide gel polymerization, add Milli-Q water to rinse the edges of coverslip. Use razor blade to carefully lift up the coverslip from one side. Rinse the gel with Milli-Q water. Now the gel is ready for printing.

Gel Print (1$^{st}$→2$^{nd}$ Surface)
Preparation of Print Solution (100 µL Per Printing):

TABLE 2

| Print Solution Formulation | |
| --- | --- |
| Bst (8 U/uL): final 0.32 U/µL | 4 µL |
| dNTPs (10 mM): final 0.2 mM | 2 µL |
| 10× Thermopol | 10 µL |
| Nuclease-free H$_2$O | 84 µL |
| Total | 100 µL |

Bst, dNTPs, BSA, and 10× Thermopol are all prepared in small aliquots kept at −20 C.

Presoak the Gel with 50 µL of Print Solution for 10 Minutes.

Setup of the Print Cassette:
From bottom to top: 1×1 inches acrylic, 1×1 inches PDMS, acrylamide gel on 1×1 inches silanzied fused-silica, print solution (addition of 500 µL print solution onto the gel), template chip (glued to 1×1 inches acrylic through double-stick tape).

Incubation for 4 Hrs in a Humidity Chamber at 55 C.
Heat Denaturation:
Dissociate the print cassette and leave the template and gel (still together) in low salt solution (0.3×SSC with 0.1% Tween-20, heated in an 80 C water bath) for 10 minutes. Carefully detach the gel from the template afterwards. Leave the gel in 4×SSC.

Gel Print ($2^{nd} \rightarrow 3^{rd}$ Surface)
Dideoxynucleotide Capping of 3' End of Oligos on the $2^{nd}$ Surface
Treat the $2^{nd}$ surface with Terminal transferase (TdT): 0.5 µL TdT, 0.4 µL of 25 mM ddCTP (or any ddNTP), 5 uL of 10× TdT buffer, 44 uL of water. 37 C for 30 minutes. Afterwards, TdT will be inactivated at 70 C for 10 minutes.
Preparation of Print Solution (100 µL Per Printing):

TABLE 3

| Print Solution Formulation | |
|---|---|
| Bst (8 U/uL): final 0.32 U/µL | 4 µL |
| dNTPs (10 mM): final 0.2 mM | 2 µL |
| 10x Thermopol | 10 µL |
| Nuclease-free H$_2$O | 84 µL |
| Total | 100 µL |

Bst, dNTPs, BSA, and 10× Thermopol are all prepared in small aliquots kept at −20 C.

Presoak the $2^{nd}$ Surface with 50 µL of Print Solution for 10 Minutes.

Setup of the Print Cassette
From bottom to top: 1×1 inches acrylic, 1×1 inches PDMS, acrylamide gel on 1×1 inches silanzied fused-silica, print solution (addition of 50 µL print solution onto the gel), $3^{rd}$ surface (1×1 cm² glued to 1×1 inches acrylic through double-stick tape).

Note: $3^{rd}$ surface is currently prepared by Meng. Basically, fused-silica in size of 1×1 cm² is used for acrylamide gel casting (acrylamide: Bromoacetyl-acrylamide=40:1). 200 µM of Phosphothiorate-CompSP2 is seeded onto gel surface overnight at room temperature.

Incubation for 4 Hrs in a Humidity Chamber at 55 C.
(the exact optimal for $2^{nd}$-$3^{rd}$ surface print is to be determined)

Heat Denaturation.
Dissociate the print cassette and leave the template and gel (still together) in low salt solution (0.3×SSC with 0.1% Tween-20, heated in an 80 C water bath) for 10 minutes. Carefully detach the gel from the template afterwards. Leave the gels in 4×SSC.

Example 4—Printing from Synthesized Chip onto Polyacrylamide $2^{nd}$ Surface

PyroPhage-based linear PCR printing can effectively increase the print signal: 10× signal increase with 30 cycles of PCR, compared with 1 hr Bst-print. A stamping hold through the printing process is critical in maintaining the printing resolution.

Figure 25:
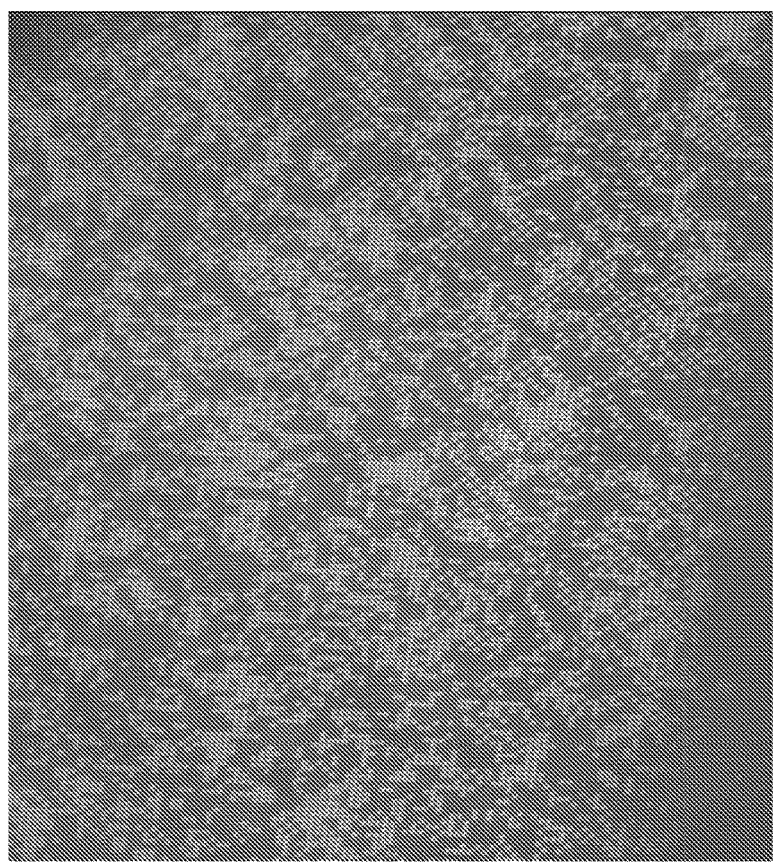
FIG. 25 illustrates an image of print (i.e., array) generated without using PyroPhage-based linear PCR printing taken at 20 s exposure, 10×, 1 bin, 100-600, hybridized with Cy3-CompSP2.
Figure 26:
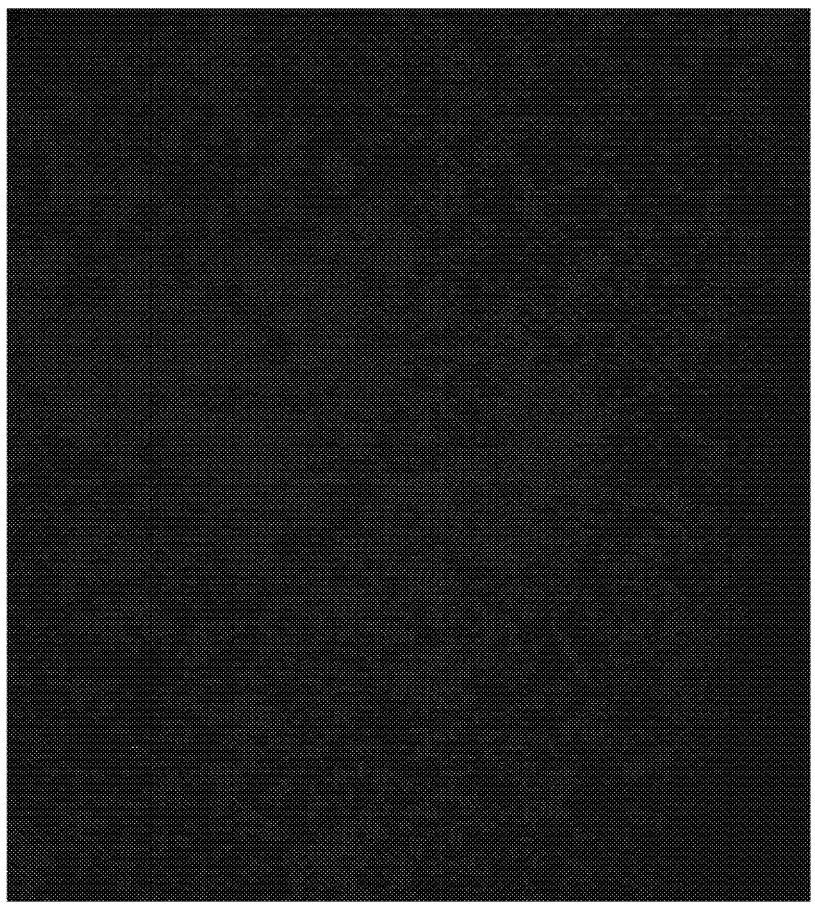
FIG. 26 illustrates an image of print (i.e., array) generated without using PyroPhage-based linear PCR printing taken at 20 s exposure, 10×, 1 bin, 100-4095, hybridized with Cy3-CompSP2.
Figure 27:
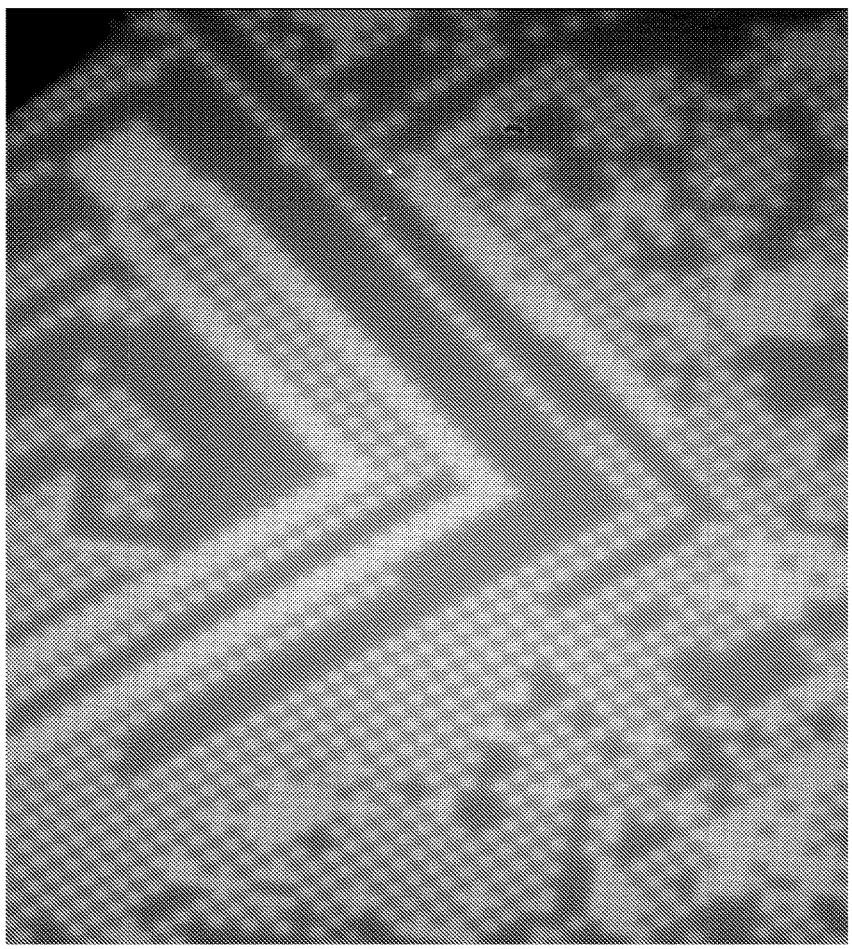
FIG. 27 illustrates an image of print (i.e., array) generated using PyroPhage-based linear PCR printing with 1 hr printing at 55 C taken at 20 s exposure, 10×, 1 bin, 1400-4095, hybridized with Cy3-CompSP2.
Figure 28:
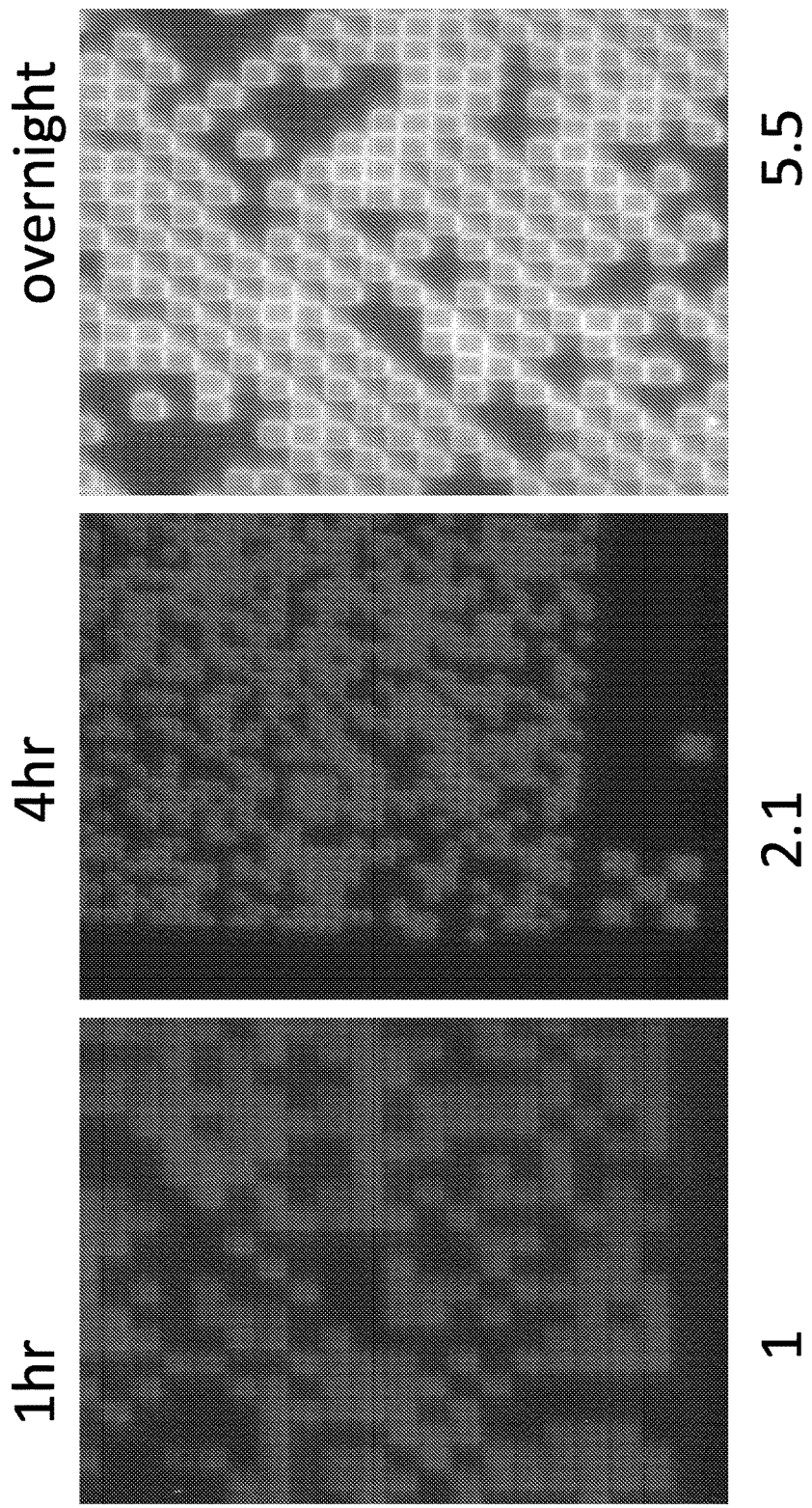
FIG. 28 illustrates a comparison of images of prints (arrays) generated using PyroPhage-based linear PCR printing from $1^{st} \rightarrow 2^{nd}$ surface for 1 hr, 4 hrs, or overnight. All images taken at all images were taken with 10 s exposure, 100-2000.
Figure 29:
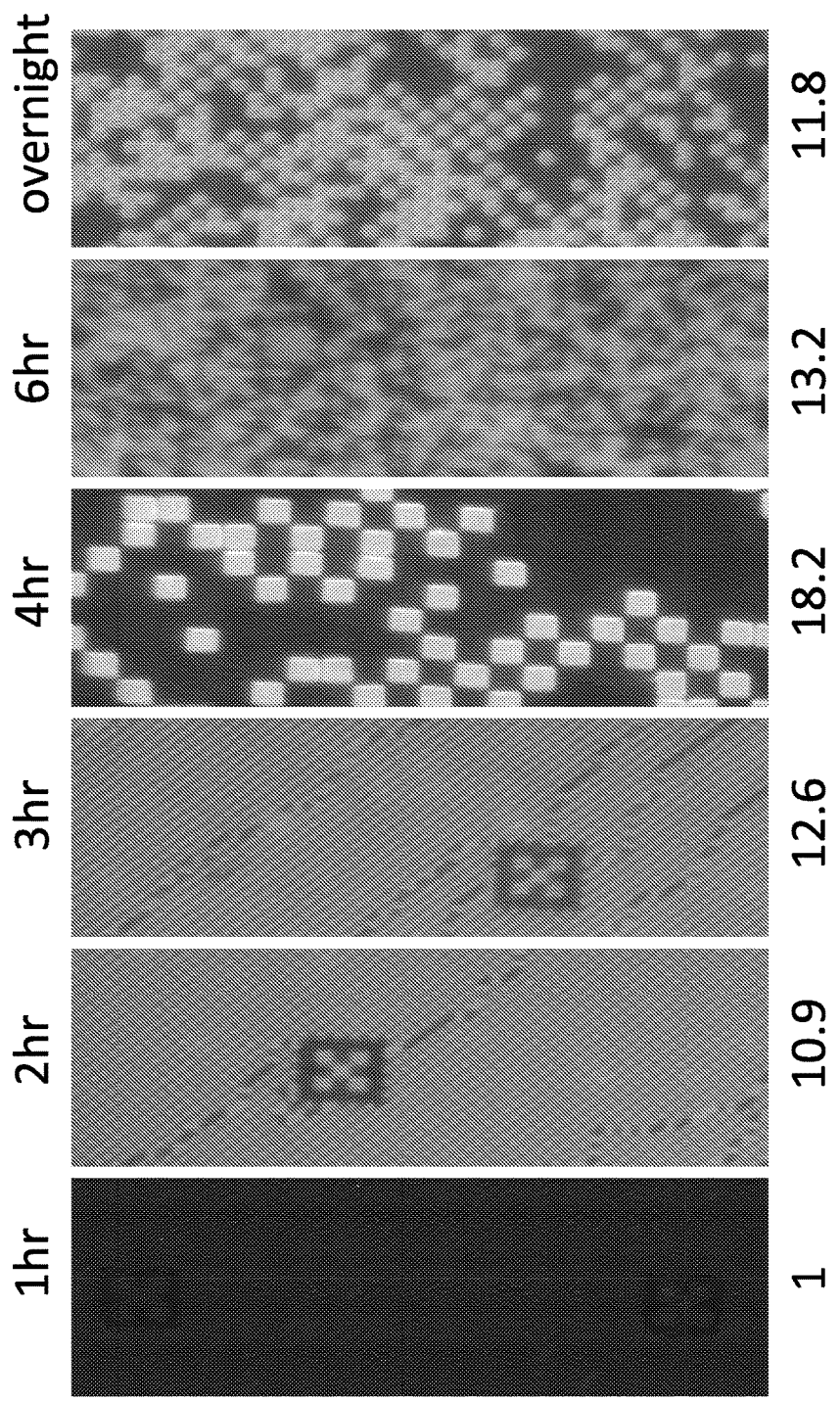
FIG. 29 illustrates a comparison of images of prints generated by Bst-based printing for 1 hr at 55 C from $1^{st} \rightarrow 2^{nd}$ surface for 1 hr, 2 hr, 3 hr, 4 hr, 6 hr and overnight. 4 hr Bst-based printing from $1^{st} \rightarrow 2^{nd}$ surface gave optimal print signal at 55 C. All images taken at all images were taken with 10 s exposure, 100-2000.

Longer printing time greatly improve the print signal (up to 18 fold), either using Bst or Pyrophage, either with 3'→5' or 5'→3' synthesized chip. 4 hr is optimal for Bst-based printing. FIG. 25 illustrates an image of print generated without using PyroPhage-based linear PCR printing taken at 20 s exposure, 10×, 1 bin, 100-600, hybridized with Cy3-CompSP2) and shows some signal, while FIG. 26 illustrates an image of print generated without using PyroPhage-based linear PCR printing taken at 20 s exposure, 10×, 1 bin, 100-4095, hybridized with Cy3-CompSP2 and shows virtually no signal. In contrast, FIG. 27 illustrates an image of print generated using PyroPhage-based linear PCR printing with 1 hr printing at 55 C taken at 20 s exposure, 10×, 1 bin, 1400-4095, hybridized with Cy3-CompSP2. FIG. 28 illustrates a comparison of images of prints (arrays) generated using PyroPhage-based linear PCR printing from $1^{st} \rightarrow 2^{nd}$ surface for 1 hr, 4 hrs, or overnight. All images taken at all images were taken with 10 s exposure, 100-2000. FIG. 28 shows that longer Pyrophage-based printing from $1^{st} \rightarrow 2^{nd}$ surface also greatly improve the signal at a constant exposure time. FIG. 29 illustrates a comparison of images from Bst-based printing generated at 55 C from $1^{st} \rightarrow 2^{nd}$ surface for 1 hr, 2 hr, 3 hr, 4 hr, 6 hr and overnight. 4 hr Bst-based printing from $1^{st} \rightarrow 2^{nd}$ surface gave optimal print signal at 55 C. All images taken at all images were taken with 10 s exposure, 100-2000. FIG. 30 illustrates images of Bst-based printing from $1^{st} \rightarrow 2^{nd}$ surface (synthesized 5'→3') synthesized for 1 hr at 55 C. FIG. 30 shows that longer Bst-based printing from $1^{st} \rightarrow 2^{nd}$ surface (synthesized 5'→3') also greatly improve the print signal compared with 1 hr printing at 55 C. All images were taken with 10 s exposure, 200-2000

In conclusion, print signal compared with 1 hr printing at 55 C and print signal was also greatly improved the print signal compared with 1 hr printing at 55 C taken at 20 s exposure, 10×, 1 bin, 1400-4095, hybridized with Cy3-CompSP2.

Figure 31:
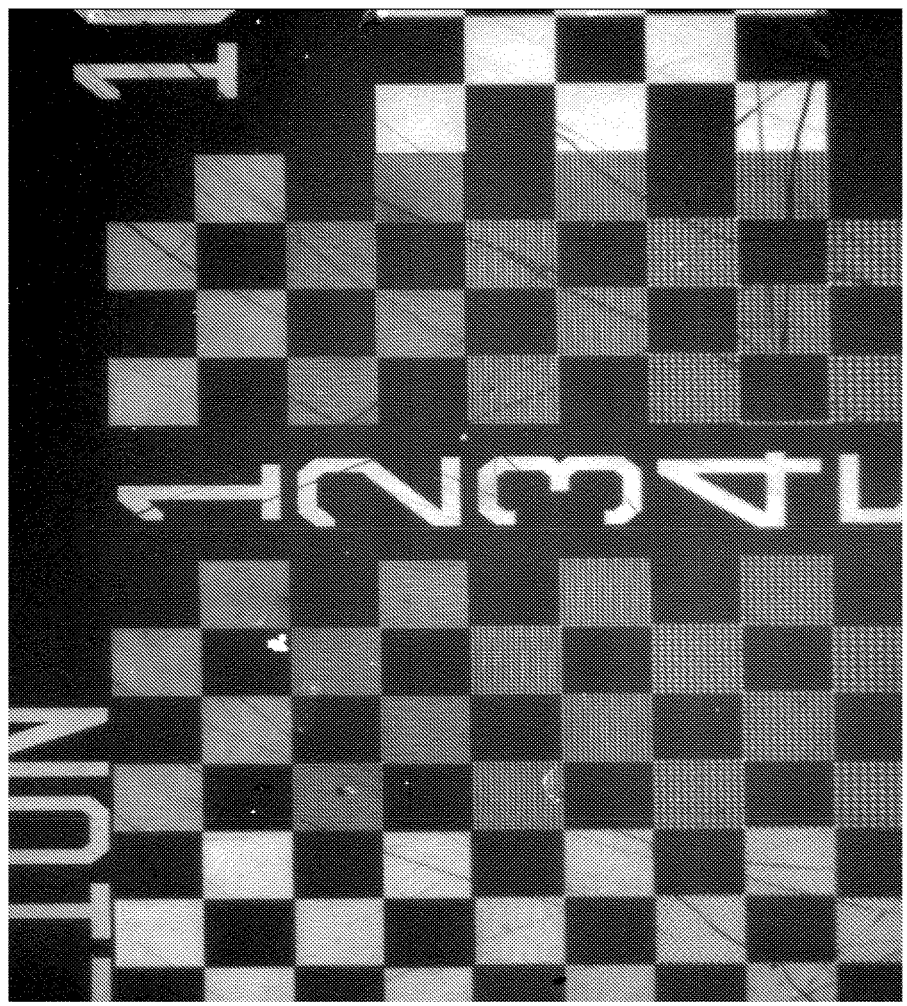
FIG. 31. illustrates Bst-based printing resolved at 1 micron.

The intensity of full-length features on the $2^{nd}$ surface (4 hr-printed) is ~10% of that on the $1^{st}$ surface. By comparing the hybridization signals between crosslinked primers in the gel and the full-length extended oligos, it was estimated that 14.3% of primers were used in 4 hr prints to generate full-length product. If the full-length product is 35.8% of total synthesized oligos (given the efficiency of each step of photosynthesis is ~95%, 20 bases in total) and there are equal chances for full length and partial length oligos to anneal to the primers, then 40.1% of total primers were used/extended during the 4 hr period. 1 micron feature can be reliably resolved on the printed $2^{nd}$ surface as shown in FIG. 31.

Figure 32:
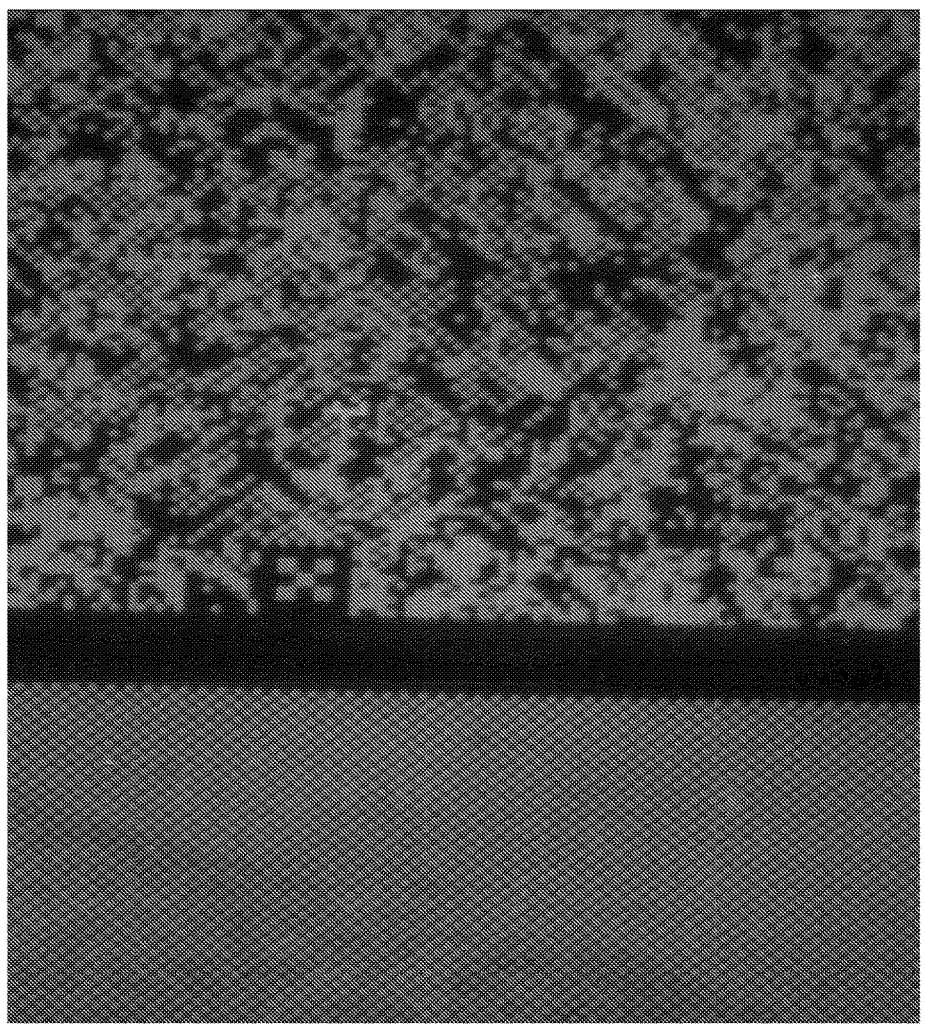
FIG. 32 illustrates a Bst overnight-printed $2^{nd}$ surface used as template to do another Bst overnight printing onto Br—Ac $3^{rd}$ surface a 10 s exposure, 10×, 1 bin, 100-600, Cy3-CompSP2.
Figure 33:
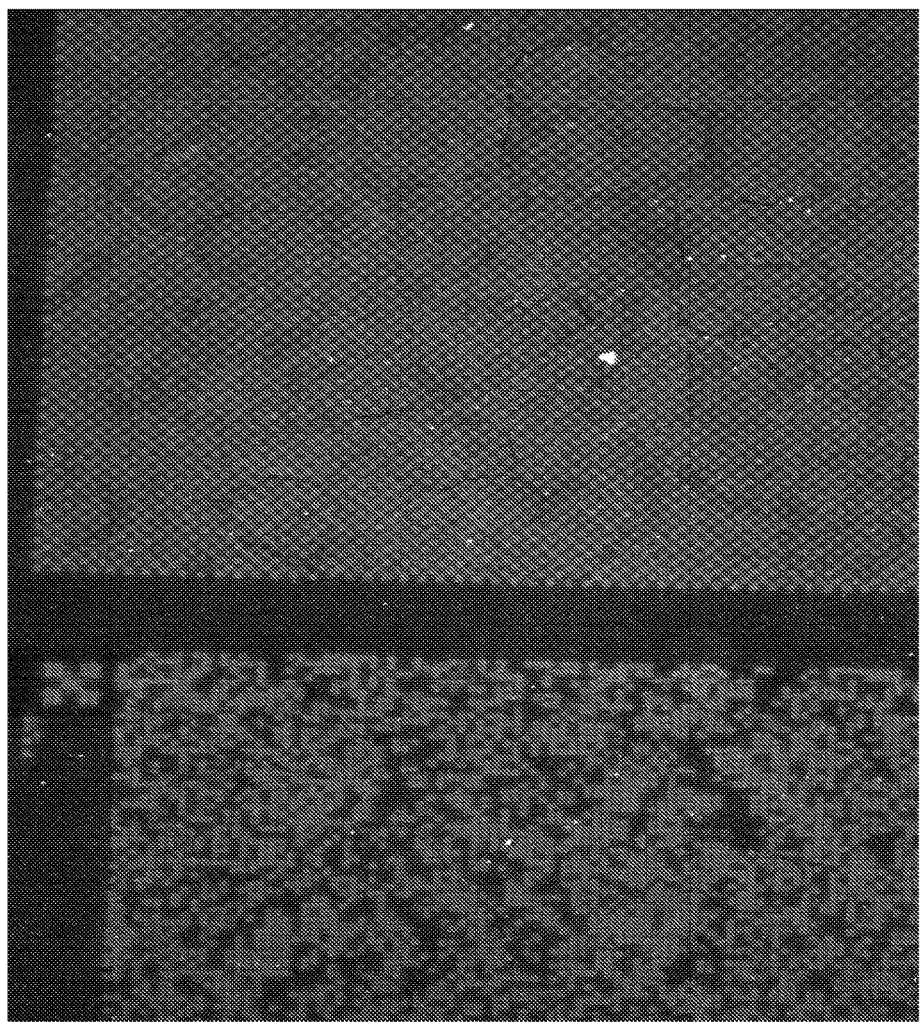
FIG. 33 illustrates Br—Ac $3^{rd}$ surface overnight-printed from overnight-printed $2^{nd}$ surface (10 s exposure, 10×, 1 bin, 200-1700, hybridized with Cy3-FC2).
Figure 34:
FIG. 34 illustrates Br—Ac $3^{rd}$ surface Pyrophage-printed and amplified from overnight-printed $2^{nd}$ surface. USER enzyme was used to cut one of the strand after PCR (10 s exposure, 10×, 1 bin, 1500-3000, Cy3-AM2).

Example 5—Printing from Polyacrylamide $2^{nd}$ Surface onto Br—Ac $3^{rd}$ Surface Bst overnight-printed $2^{nd}$ surface was used as template to do another Bst overnight printing onto Br—Ac $3^{rd}$ surface. After background signal subtraction, the intensity of full-length features on the $2^{nd}$ surface (overnight-printed, FIG. 32) and $3^{rd}$ surface are 5%-10% and 2%-3% of those on the $1^{st}$ surface, respectively. FIG. 32 shows a 10 s exposure, 10×, 1 bin, 100-600, Cy3-CompSP2. As an alternative way to do overnight printing, Br—Ac $3^{rd}$ surface was printed and amplified from overnight-printed $2^{nd}$ surface through PCR (see FIG. 33). FIG. 33 shows Br—Ac $3^{rd}$ surface overnight-printed from overnight-printed $2^{nd}$ surface (10 s exposure, 10×, 1 bin, 200-1700, hybridized with Cy3-FC2). In this method, the printed and amplified full-length oligos have a density 5%-7% of those on the $1^{st}$ surface. Uneven printed signal was seen in some cases of the two $2^{nd} \rightarrow 3^{rd}$ printing methods, which could be from uneven primer seeding and/or damages during printing and separation. FIG. 34 illustrates Br—Ac $3^{rd}$ surface Pyrophage-printed and amplified from overnight-printed 2$^{nd}$ surface. USER enzyme was used to cut one of the strand after PCR. (10 s exposure, 10×, 1 bin, 1500-3000, Cy3-AM2).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method for generating an array comprising:
   providing a template array comprising at least 1,000 different oligonucleotides coupled thereto,
   coupling the template array to a recipient array having a plurality of oligonucleotides complementary to portions of the at least 1,000 different oligonucleotides, and
   performing an enzymatic reaction while each of the at least 1,000 different oligonucleotides of the template array hybridizes with a member of the plurality of oligonucleotides of the recipient array, thereby generating a recipient array comprising recipient oligonucleotides, wherein at least 40% of the recipient oligonucleotides are complementary to a full-length oligonucleotide from the at least 1,000 different oligonucleotides, wherein each of the at least 1,000 different oligonucleotides comprises a barcode, and wherein the barcode identifies the spatial position of each of the at least 1,000 different oligonucleotides.

2. The method of claim 1, wherein the template array comprises at least 100 spots.

3. The method of claim 1, wherein the template array comprises spots at most about 500 µm in size.

4. The method of claim 1, wherein the directionality of the recipient oligonucleotides relative to the recipient array is the same as the directionality of the template oligonucleotides relative to the template array.

5. The method of claim 1, wherein the directionality of the recipient oligonucleotides relative to the recipient array is the opposite of the directionality of the template oligonucleotides relative to the template array.

6. The method of claim 1, wherein a plurality of recipient arrays are generated.

7. The method of claim 6, wherein the plurality of recipient oligonucleotides are on average at least 99% identical between one recipient array and another.

8. The method of claim 6, wherein the recipient oligonucleotides are at least 99% identical between one recipient array and another.

9. A method for generating a complementary array comprising:
   (a) providing a plurality of template oligonucleotides coupled to a first substrate, each of the plurality of template oligonucleotides comprising an adaptor sequence and a barcode, wherein the adaptor sequence is the same for each of the plurality of template oligonucleotides, wherein the barcode identifies the spatial position of each of the plurality of template oligonucleotides;
   (b) providing a plurality of recipient oligonucleotides coupled to a second substrate, each of the plurality of recipient oligonucleotides comprising sequence complementary to the adaptor sequence;
   (c) hybridizing the adaptor sequence of the template oligonucleotides and the sequence complementary to the adaptor sequence of the recipient oligonucleotides; and
   (d) conducting extension reactions on the plurality of recipient oligonucleotides using the plurality of template oligonucleotides as templates.

10. The method of claim 9, wherein each of the adaptor sequences is located at or near the 3' end of the template oligonucleotides.

11. The method of claim 9, wherein each of the adaptor sequences is located at or near the 5' end of the template oligonucleotides.

12. The method of claim 9, wherein the conducting step results in generation of recipient oligonucleotides at least 40% of which are full-length products.

13. The method of claim 9, wherein the method is repeated to produce at least 2 recipient arrays.

14. A method for transferring an array, comprising:
   (a) providing a substrate comprising a plurality of linker sites;
   (b) providing an array comprising a plurality of template oligonucleotides, each of the plurality of template oligonucleotides comprises a barcode, and wherein the barcode identifies the spatial position of each of the plurality of template oligonucleotides;
   (c) applying reaction mix to the array, the reaction mix comprising enzyme, dNTPs, and a plurality of linker oligonucleotides comprising sequence complementary to an adaptor sequence appended to each of the plurality of template oligonucleotides and further comprising linker molecules capable of binding to the plurality of linker sites;
   (d) conducting extension reactions of the plurality of the linker oligonucleotides using the plurality of template oligonucleotides as templates, thereby generating a plurality of extension products comprising the linker molecules;
   (e) contacting the array with the substrate; and
   (f) linking the linker molecules of the plurality of extension products to the linker sites.

15. The method of claim 14, wherein the adaptor sequence is located at or near the 3' end of the template oligonucleotides.

16. The method of claim 14, wherein the adaptor sequence is located at or near the 5' end of the template oligonucleotides.

17. The method of claim 14, wherein the substrate comprises polymer.

18. The method of claim 14, wherein the substrate comprises acrylamide or polyacrylamide.

19. The method of claim 14, wherein the template array comprises at least 100 spots.

20. The method of claim 14, wherein the template array comprises spots at most about 500 µm in size.

* * * * *